United States Patent
Le Duc De Lillers et al.

(10) Patent No.: US 11,623,077 B2
(45) Date of Patent: Apr. 11, 2023

(54) IMPLANTABLE PUMP SYSTEM HAVING A RECTANGULAR MEMBRANE

(71) Applicant: CorWave SA, Clichy (FR)

(72) Inventors: Louis-Emmanuel Le Duc De Lillers, Paris (FR); Francois Cornat, Paris (FR); Jean-Baptiste Drevet, Paris (FR); Carl N. Botterbusch, Wyomissing, PA (US); Alexandra Schmidt, Paris (FR)

(73) Assignee: CorWave SA, Clichy (FR)

(*) Notice: Subject to any disclaimer, the term of this patent is extended or adjusted under 35 U.S.C. 154(b) by 238 days.

(21) Appl. No.: 17/179,961

(22) Filed: Feb. 19, 2021

(65) Prior Publication Data
US 2021/0170160 A1    Jun. 10, 2021

Related U.S. Application Data

(63) Continuation of application No. 15/940,856, filed on Mar. 29, 2018, now Pat. No. 10,933,181.
(Continued)

(51) Int. Cl.
*A61M 60/148*    (2021.01)
*A61M 60/268*    (2021.01)
(Continued)

(52) U.S. Cl.
CPC ........ *A61M 60/148* (2021.01); *A61M 60/268* (2021.01); *A61M 60/462* (2021.01);
(Continued)

(58) Field of Classification Search
None
See application file for complete search history.

(56) References Cited

U.S. PATENT DOCUMENTS

| | | |
|---|---|---|
| 2,842,067 A | 7/1958 | John et al. |
| 3,107,630 A | 10/1963 | Johnson et al. |

(Continued)

FOREIGN PATENT DOCUMENTS

| | | |
|---|---|---|
| AU | 2013203301 A1 | 5/2013 |
| AU | 2013203301 B2 | 10/2015 |

(Continued)

OTHER PUBLICATIONS

Ando, et al., Electrocardiogram-Synchronized Rotational Speed Change Mode in Rotary Pumps Could Improve Pulsatility, Artificial Organs, 35(10):941-947 (2011).
(Continued)

*Primary Examiner* — Ankit D Tejani
(74) *Attorney, Agent, or Firm* — Eversheds Sutherland US LLP; Christopher C. Bolten; Robert D. Ward

(57) ABSTRACT

An implantable pump system is provided, including an implantable blood pump suitable for use as a partial support assist device, the system further including an extracorporeal battery and a controller coupled to the implantable pump, and a programmer selectively periodically coupled to the controller to configure and adjust operating parameters of the implantable pump. The implantable pump includes a flexible membrane coupled to an electromagnetic actuator including a magnetic assembly and electromagnetic assembly, so that when the electromagnetic assembly is energized, the electromagnetic assembly causes wavelike undulations to propagate along the flexible membrane to propel blood through the implantable pump. The controller may be programmed by a programmer to operate at frequencies and duty cycles that mimic physiologic flow rates and pulsatility while operating in an efficient manner that avoids thrombus formation, hemolysis and/or platelet activation.

20 Claims, 32 Drawing Sheets

Related U.S. Application Data

(60) Provisional application No. 62/592,349, filed on Nov. 29, 2017, provisional application No. 62/505,023, filed on May 11, 2017, provisional application No. 62/480,333, filed on Mar. 31, 2017.

(51) Int. Cl.
*A61M 60/462* (2021.01)
*A61M 60/88* (2021.01)
*A61M 60/861* (2021.01)
*A61M 60/538* (2021.01)
*A61M 60/515* (2021.01)
*A61M 60/122* (2021.01)

(52) U.S. Cl.
CPC ........ *A61M 60/515* (2021.01); *A61M 60/538* (2021.01); *A61M 60/861* (2021.01); *A61M 60/88* (2021.01); *A61M 60/122* (2021.01); *A61M 2205/3303* (2013.01)

(56) References Cited

U.S. PATENT DOCUMENTS

| | | |
|---|---|---|
| 3,165,061 A | 1/1965 | Smith et al. |
| 3,608,088 A | 9/1971 | Dorman et al. |
| 3,620,651 A | 11/1971 | Peter |
| 3,743,446 A | 7/1973 | Mandroian |
| 3,765,175 A | 10/1973 | Ohnaka |
| 4,063,826 A | 12/1977 | Riepe |
| 4,277,706 A | 7/1981 | Isaacson |
| 4,384,830 A | 5/1983 | Wakelin |
| 4,484,095 A | 11/1984 | Neumann |
| 4,488,854 A | 12/1984 | Miller |
| 4,498,851 A | 2/1985 | Kolm et al. |
| 4,648,807 A | 3/1987 | Tippetts et al. |
| 4,753,221 A | 6/1988 | Kensey et al. |
| 4,906,229 A | 3/1990 | Wampler |
| 4,931,036 A | 6/1990 | Kanai et al. |
| 4,939,405 A | 7/1990 | Okuyama et al. |
| 4,955,856 A | 9/1990 | Phillips |
| 4,995,857 A | 2/1991 | Arnold |
| 5,147,388 A | 9/1992 | Yamazaki |
| 5,263,978 A | 11/1993 | Kaufmann et al. |
| 5,275,580 A | 1/1994 | Yamazaki |
| 5,360,445 A | 11/1994 | Goldowsky |
| 5,370,509 A | 12/1994 | Golding et al. |
| 5,525,041 A | 6/1996 | Deak |
| 5,588,812 A | 12/1996 | Taylor et al. |
| 5,982,801 A | 11/1999 | Deak |
| 6,058,593 A | 5/2000 | Siess |
| 6,079,214 A | 6/2000 | Bishop |
| 6,083,260 A | 7/2000 | Aboul-Hosn |
| 6,116,862 A | 9/2000 | Rau et al. |
| 6,123,725 A | 9/2000 | Aboul-Hosn |
| 6,176,822 B1 | 1/2001 | Nix et al. |
| 6,176,848 B1 | 1/2001 | Rau et al. |
| 6,346,071 B1 | 2/2002 | Mussivand |
| 6,361,284 B2 | 3/2002 | Drevet |
| 6,395,026 B1 | 5/2002 | Aboul-Hosn et al. |
| 6,530,876 B1 | 3/2003 | Spence |
| 6,532,964 B2 | 3/2003 | Aboul-Hosn et al. |
| 6,658,740 B2 | 12/2003 | Habben |
| 6,659,740 B2 | 12/2003 | Drevet |
| 6,672,847 B2 | 1/2004 | Dooley |
| 6,723,039 B2 | 4/2004 | French et al. |
| 6,726,648 B2 | 4/2004 | Kaplon et al. |
| 6,732,501 B2 | 5/2004 | Yu et al. |
| 6,811,381 B2 | 11/2004 | Dooley |
| 6,848,001 B1 | 1/2005 | Sakamoto et al. |
| 6,935,344 B1 | 8/2005 | Aboul-Hosn et al. |
| 6,976,996 B1 | 12/2005 | Aboul-Hosn |
| 7,011,620 B1 | 3/2006 | Siess |
| 7,027,875 B2 | 4/2006 | Siess et al. |
| 7,182,727 B2 | 2/2007 | Aboul-Hosn |
| 7,323,961 B2 | 1/2008 | Drevet |
| 7,520,850 B2 | 4/2009 | Brockway |
| 7,696,634 B2 | 4/2010 | Filardo |
| 7,736,296 B2 | 6/2010 | Siess et al. |
| 7,839,007 B2 | 11/2010 | Filardo |
| 7,863,768 B2 | 1/2011 | Filardo |
| 7,889,877 B2 | 2/2011 | Lutz |
| 7,988,728 B2 | 8/2011 | Ayre |
| 8,012,079 B2 | 9/2011 | Delgado, III |
| 8,152,845 B2 | 4/2012 | Bourque |
| 8,157,720 B2 | 4/2012 | Marseille et al. |
| 8,333,686 B2 | 12/2012 | Marseille et al. |
| 8,343,029 B2 | 1/2013 | Farnan et al. |
| 8,394,009 B2 | 3/2013 | Bolyard et al. |
| 8,394,010 B2 | 3/2013 | Farnan |
| 8,432,057 B2 | 4/2013 | Filardo |
| 8,449,444 B2 | 5/2013 | Poirier |
| 8,465,410 B2 | 6/2013 | Marseille et al. |
| 8,512,012 B2 | 8/2013 | Akdis et al. |
| 8,550,975 B2 | 10/2013 | Foster |
| 8,556,795 B2 | 10/2013 | Bolyard et al. |
| 8,562,508 B2 | 10/2013 | Dague et al. |
| 8,585,571 B2 | 11/2013 | Bachman et al. |
| 8,597,350 B2 | 12/2013 | Rudser et al. |
| 8,610,304 B2 | 12/2013 | Filardo |
| 8,714,944 B2 | 5/2014 | Drevet |
| 8,753,256 B2 | 6/2014 | Bolyard et al. |
| 8,784,291 B2 | 7/2014 | Farnan et al. |
| 8,821,366 B2 | 9/2014 | Farnan et al. |
| 8,821,527 B2 | 9/2014 | Farnan et al. |
| 8,827,888 B2 | 9/2014 | Bolyard et al. |
| 8,834,136 B2 | 9/2014 | Drevet |
| 8,852,072 B2 | 10/2014 | LaRose et al. |
| 8,870,739 B2 | 10/2014 | LaRose et al. |
| 8,956,275 B2 | 2/2015 | Bolyard et al. |
| 8,976,546 B2 | 3/2015 | Wang et al. |
| 9,022,916 B2 | 5/2015 | Farnan et al. |
| 9,080,564 B2 | 7/2015 | Drevet |
| 9,089,635 B2 | 7/2015 | Reichenbach et al. |
| 9,144,669 B2 | 9/2015 | Wieselthaler |
| 9,145,875 B2 | 9/2015 | Filardo |
| 9,173,984 B2 | 11/2015 | LaRose et al. |
| 9,211,367 B2 | 12/2015 | Farnan et al. |
| 9,308,304 B2 | 4/2016 | Peters et al. |
| 9,446,180 B2 | 9/2016 | Vadala, Jr. et al. |
| 9,526,819 B2 | 12/2016 | Chen |
| 9,572,915 B2 | 2/2017 | Heuring et al. |
| 9,579,437 B2 | 2/2017 | LaRose et al. |
| 9,616,158 B2 | 4/2017 | Yaghdjian |
| 9,694,123 B2 | 7/2017 | Bourque et al. |
| 9,731,057 B2 | 8/2017 | Garrigue |
| 9,744,279 B2 | 8/2017 | Tamez et al. |
| 9,786,150 B2 | 10/2017 | Kimball et al. |
| 9,861,728 B2 | 1/2018 | Farnan et al. |
| 9,956,333 B2 | 5/2018 | LaRose et al. |
| 9,968,720 B2 | 5/2018 | Botterbusch et al. |
| 10,166,319 B2 | 1/2019 | Botterbusch et al. |
| 10,188,779 B1 | 1/2019 | Polverelli et al. |
| 10,398,821 B2 | 9/2019 | Botterbusch et al. |
| 10,799,625 B2 | 10/2020 | Scheffler et al. |
| 2001/0001278 A1 | 5/2001 | Drevet |
| 2002/0095210 A1 | 7/2002 | Finnegan et al. |
| 2002/0146333 A1 | 10/2002 | Drevet |
| 2002/0165426 A1 | 11/2002 | Sporer et al. |
| 2003/0002325 A1 | 1/2003 | Alvandpour et al. |
| 2004/0002624 A1 | 1/2004 | Yu et al. |
| 2005/0261543 A1 | 11/2005 | Abe et al. |
| 2005/0288543 A1 | 12/2005 | Stenberg et al. |
| 2006/0014999 A1 | 1/2006 | Heilman et al. |
| 2006/0155158 A1 | 7/2006 | Aboul-Hosn |
| 2006/0288543 A1 | 12/2006 | Lubera et al. |
| 2007/0299297 A1 | 12/2007 | Jarvik |
| 2008/0232987 A1 | 9/2008 | Drevet |
| 2009/0082778 A1 | 3/2009 | Beane et al. |
| 2010/0234941 A1 | 9/2010 | Finocchiaro et al. |
| 2010/0241223 A1 | 9/2010 | Lee et al. |
| 2011/0124950 A1 | 5/2011 | Foster |
| 2011/0176945 A1 | 7/2011 | Drevet |
| 2011/0176946 A1 | 7/2011 | Drevet |

(56) References Cited

U.S. PATENT DOCUMENTS

| | | |
|---|---|---|
| 2011/0260449 A1 | 10/2011 | Pokorney |
| 2012/0220816 A1 | 8/2012 | Peters et al. |
| 2012/0323318 A1 | 12/2012 | Yusuf et al. |
| 2013/0078122 A1 | 3/2013 | Drevet |
| 2013/0178694 A1 | 7/2013 | Jeffery et al. |
| 2013/0314047 A1 | 11/2013 | Eagle et al. |
| 2014/0023533 A1 | 1/2014 | Ishii et al. |
| 2014/0187852 A1 | 7/2014 | Peters et al. |
| 2014/0207232 A1 | 7/2014 | Garrigue |
| 2014/0275723 A1 | 9/2014 | Fritz, IV et al. |
| 2014/0277423 A1 | 9/2014 | Alkhatib et al. |
| 2014/0316426 A1 | 10/2014 | Gollner et al. |
| 2015/0167659 A1 | 6/2015 | Sauer |
| 2015/0330383 A1 | 11/2015 | Letailleur et al. |
| 2016/0038664 A1 | 2/2016 | Callaway et al. |
| 2016/0051738 A1 | 2/2016 | Callaway et al. |
| 2016/0235899 A1 | 8/2016 | Yu et al. |
| 2016/0243294 A1 | 8/2016 | Peters et al. |
| 2017/0012491 A1 | 1/2017 | Schob et al. |
| 2017/0266358 A1 | 9/2017 | Aber |
| 2017/0290966 A1 | 10/2017 | Botterbusch et al. |
| 2017/0290967 A1 | 10/2017 | Botterbusch et al. |
| 2017/0296723 A1 | 10/2017 | Garrigue |
| 2018/0038364 A1 | 2/2018 | Dumas et al. |
| 2018/0050143 A1 | 2/2018 | Nguyen et al. |
| 2018/0256798 A1 | 9/2018 | Botterbusch et al. |
| 2018/0369469 A1 | 12/2018 | Le Duc De Lillers et al. |
| 2019/0125949 A1 | 5/2019 | Botterbusch et al. |
| 2019/0381227 A1 | 12/2019 | Botterbusch et al. |
| 2020/0368417 A1 | 11/2020 | Polverelli et al. |

FOREIGN PATENT DOCUMENTS

| | | |
|---|---|---|
| EP | 0412856 A1 | 2/1991 |
| EP | 0415949 A1 | 3/1991 |
| EP | 0445782 B1 | 8/1994 |
| EP | 0925081 B1 | 12/2003 |
| EP | 0961621 B1 | 7/2004 |
| EP | 1551500 A2 | 7/2005 |
| EP | 1233797 B1 | 7/2006 |
| EP | 1337288 B1 | 3/2008 |
| EP | 1981585 A2 | 10/2008 |
| EP | 1644639 B1 | 2/2009 |
| EP | 2152339 A1 | 2/2010 |
| EP | 2249746 A1 | 11/2010 |
| EP | 2310067 A1 | 4/2011 |
| EP | 2600918 A1 | 6/2013 |
| EP | 2517739 B1 | 12/2013 |
| EP | 2704761 A1 | 3/2014 |
| EP | 2310067 B1 | 4/2014 |
| EP | 2753389 A1 | 7/2014 |
| EP | 2152339 B1 | 5/2015 |
| EP | 2891502 A1 | 7/2015 |
| EP | 2704761 B1 | 9/2015 |
| EP | 2736552 B1 | 9/2015 |
| EP | 2891502 B1 | 7/2016 |
| EP | 2164542 B1 | 8/2016 |
| EP | 2856190 B1 | 9/2016 |
| EP | 3145558 A2 | 3/2017 |
| FR | 355700 A | 11/1905 |
| FR | 2650862 B1 | 11/1991 |
| FR | 2744769 A1 | 8/1997 |
| FR | 2744769 B1 | 2/1999 |
| FR | 2861910 B1 | 1/2006 |
| FR | 2905147 A1 | 2/2008 |
| FR | 3032917 A1 | 8/2016 |
| GB | 662047 A | 11/1951 |
| KR | 20130068373 A | 6/2013 |
| WO | WO-8910763 A1 | 11/1989 |
| WO | WO-9008260 A1 | 7/1990 |
| WO | WO-9729282 A1 | 8/1997 |
| WO | WO-9959652 A1 | 11/1999 |
| WO | WO-2007053881 A1 | 5/2007 |
| WO | WO-2011056823 A2 | 5/2011 |
| WO | WO-2017087717 A1 | 5/2017 |
| WO | WO-2017087785 A1 | 5/2017 |
| WO | WO-2019092175 A1 | 5/2019 |
| WO | WO-2020115607 A1 | 6/2020 |

OTHER PUBLICATIONS

Ando, et al., Left ventricular decompression through a patent foramen ovale in a patient with hypertrophic cardiomyopathy: A case report, Cardiovascular Ultrasound, 2: 1-7 (2004).

Bozkurt, et al., Improving Arterial Pulsatility by Feedback Control of a Continuous Flow Left Ventricular Assist Device via in silico Modeling, International Journal of Artificial Organs, 37(10):773-785 (2014).

Castellanos, et al., Generations of Left Ventricular Assist Devices: The HeartMate Family, Dept. of Bioengineering. Florida Gulf Coast University, BME 3100C, pp. 1-6. (No date available).

Crow, et al., Gastrointestinal Bleeding Rates in Recipients of Nonpulsatile and Pulsatile Left Ventricular Assist Devices, The Journal of Thoracic and Cardiovascular Surgery, 137(1):208-215 (2009).

Fatullayev, et al., Continuous-Flow Left Ventricular Assist Device Thrombosis: A Danger Foreseen is a Danger Avoided, Medical Science Monitor Basic Research, 21:141-144 (2015).

Feier, et al., A Novel, Valveless Ventricular Assist Device: The Fish Tail Pump. First Experimental in Vivo Studies, Artificial Organs, (26)12:1026-1031 (2002).

Fliess, et al., Flatness and Defect of Nonlinear Systems: Introductory Theory and Examples, International Journal of Control, 61(6):1327-1361 (1995).

Fraser et al., A Quantitative Comparison of Mechanical Blood Damage Parameters in Rotary Ventricular Assist Devices: Shear Stress, Exposure Time and Hemolysis Index, Journal of Biomechanical Engineering, 134(8):018002-1 to 018002-11 (2012).

Harris, et al., Ventricular Assist Devices, Continuing Education in Anesthesia, Critical Care & Pain, 12(3):145-151 (2012).

International Search Report & Written Opinion dated Mar. 4, 2019 in Int'l PCT Patent Appl No. PCT/IB2018/059199, 13 pages (0510).

International Search Report & Written Opinion dated Aug. 22, 2017 in Int'l PCT Patent Application Serial No. PCT/IB2017/052069 (0310).

International Search Report & Written Opinion dated Jun. 28, 2017 in Int'l PCT Patent Application Serial No. PCT/IB2017/052068 (0210).

International Search Report & Written Opinion dated Jul. 15, 2020 in Int'l PCT Patent Appl. Serial No. PCT/IB2019/060144 (0610).

International Search Report and Written Opinion dated Apr. 16, 2019 in Int'l PCT Patent Appl. Serial No. PCT/EP2018/080749 (English Translation of ISR only) (0810).

International Search Report and Written Opinion dated Jun. 25, 2020 in International PCT Patent Application Serial No. PCT/IB2020/052337 (0710 PCT).

International Search Report and Written Opinion dated Aug. 3, 2018 in Int'l PCT Patent Appl. Serial No. PCT/IB2018/052215 (0410).

Ising, M., RPM and Flow Modulation for a Continuous Flow Left Ventricular Assist Device to Increase Vascular Pulsatility: A Computer Simulation, Mock Circulation, and In-Vivo Animal Study, University of Louisville, Think IR: The University of Louisville's Institutional Repository, Electronic Theses and Dissertations (Jul. 2011).

Islam et al., Left Ventricular Assist Devices and Gastrointestinal Bleeding: A Narrative Review of Case Reports and Case Series, Clinical Cardiology, 36(4):190-200 (2013).

Jorde, et al., Identification and Management of Pump Thrombus in the HeartWare Left Ventricular Assist Device System, JACC: Heart Failure, 3(11):849-856 (2015).

Latham, et al., Parameter Estimation and a Series of Nonlinear Observers for the System Dynamics of a Linear Vapor Compressor, IEEE Transactions on Industrial Electronics, 63(11):6736-6744 (2016).

Leverett, et al., Red Blood Cell Damage by Shear Stress, Biophysical Journal, 12(3):257-273(1972).

(56) References Cited

OTHER PUBLICATIONS

Malehsa, et al., Acquired von Willebrand Syndrome After Exchange of the HeartMate XVE to the HeartMate II Ventricular Assist Device, European Journal of Cardio-Thoracic Surgery, 35(6):1091-1093 (2009).

Mancini, et al., Left Ventricular Assist Devices, A Rapidly Evolving Alternative to Transplant, Journal of the American College of Cardiology, 653:2542-2555 (2015).

Mboup, et al., Numerical Differentiation With Annihilators in Noisy Environment, Numerical Algorithms, 50(4):439-467 (2009).

Menhour, et al., An Efficient Model-Free Setting for Longitudinal and Lateral Vehicle Control: Validation Through the Interconnected Pro-SiVIC/RTMaps Prototyping Platform, IEEE Transactions on Intelligent Transportation Systems, 19(2):461-475 (2018).

Mercorelli, P., A Motion-Sensorless Control for Intake Valves in Combustion Engines, IEEE Transactions on Industrial Electronics, 64(4):3402-3412 (2017).

Mercorelli, P., An Adaptive and Optimized Switching Observer for Sensorless Control of an Electromagnetic Valve Actuator in Camless Internal Combustion Engines, Asian Journal of Control, 16(4):959-973 (2014).

Mohite, et al., Does CircuLite Synergy Assist Device as Partial Ventricular Support have a Place in Modern Management of Advanced Heart Failure?, Expert Rev. Med. Devices, published online Dec. 2, 2014 (pp. 1-12).

Najjar, et al., An Analysis of Pump Thrombus Events in Patients in HeartWare Advance Bridge to Transplant and Continued Access Protocol Trial, The Journal of Heart and Lung Transplantation, 33(1):23-34 (2014).

Pagani, Francis D., MD, PhD, Department of Cardiac Surgery, University of Michigan, "Technology 101: Review of Current Technologies, Types of Flow, Pump Parameters," American Association for Thoracic Surgery, Annual Meeting (2014), Cardiothoracic Transplant and Mechanical Circulatory Support of Heart and Lung Failure.

Perschall, et al., The Progressive Wave Pump: Numerical Multiphysics Investigation of a Novel Pump Concept With Potential to Ventricular Assist Device Application, Artificial Organs, 35(9):E179-E190 (2012).

Rahman, et al., Position Estimation in Solenoid Actuators, IEEE Transactions on Industry Applications, 32(3):552-559 (1996).

Rigatos, G., Differential Flatness Theory ad Flatness-Based Control, in Nonlinear Control and Filtering Using Differential Flatness Approaches, 25(2):47-101 (2015).

Wang, et al., Rotary Blood Pump Control Strategy for Preventing Left Ventricular Suction, ASAIO Journal, 61(1):21-30(2015).

Wang., Quadrotor Analysis and Model Free Control with Comparisons, Universite Paris Sud—Paris XI, (2013).

Weidemann, Daniel., Thesis entitled, Permanent Magnet Reluctance Actuators for Vibration Testing, Completed at the Institute of Applied Mechanics, Technische Universitat Munchen, Apr. 2013.

Yuan, et al., The Spectrum of Complications Following Left Ventricular Assist Device Placement, Journal of Cardiac Surgery, 27:630-638 (2012).

Zhang, et al., Study on Self-Sensor of Linear Moving Magnet Compressor's Piston Stroke, IEEE Sensors Journal, 9(2):154-158 (2009).

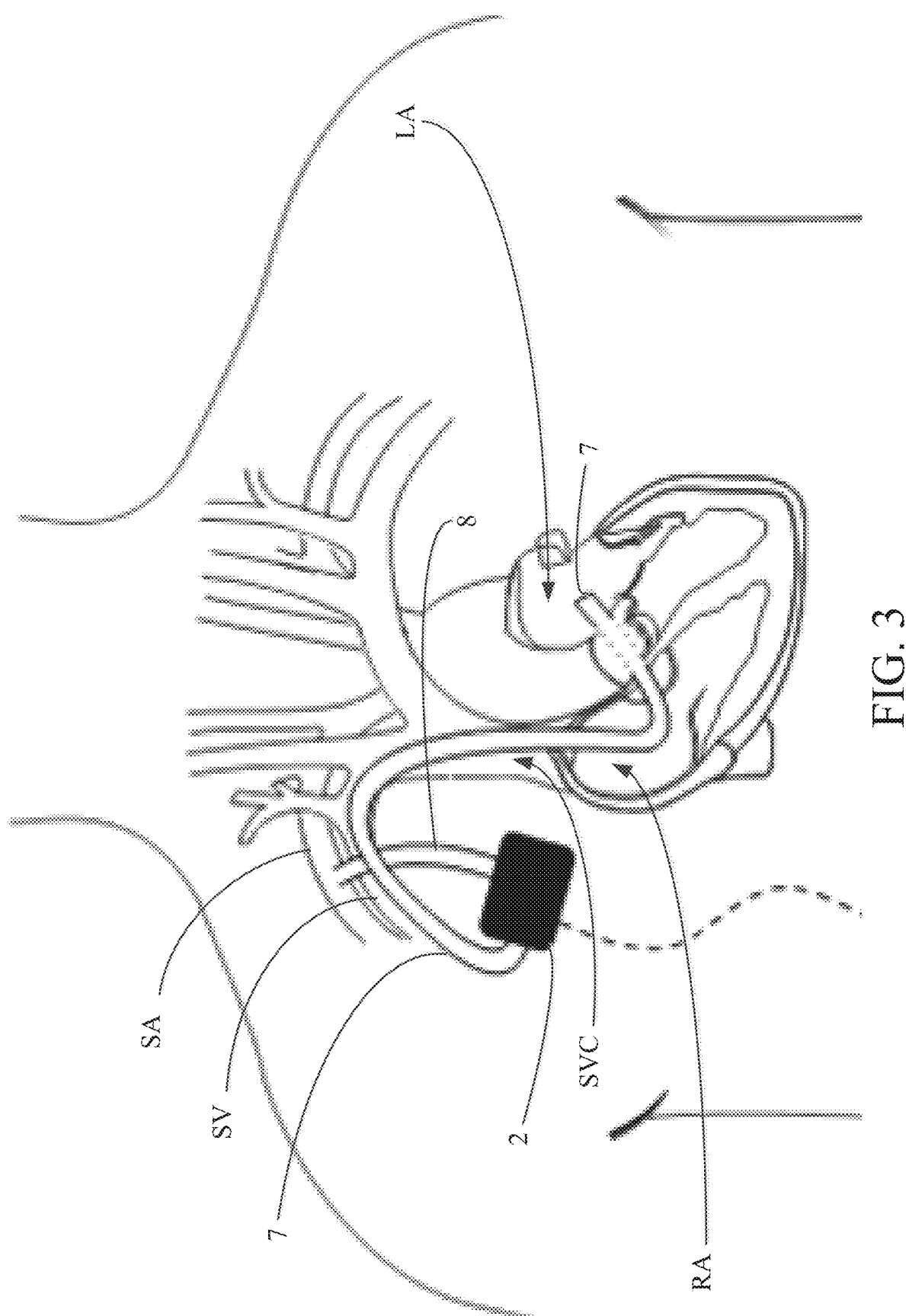

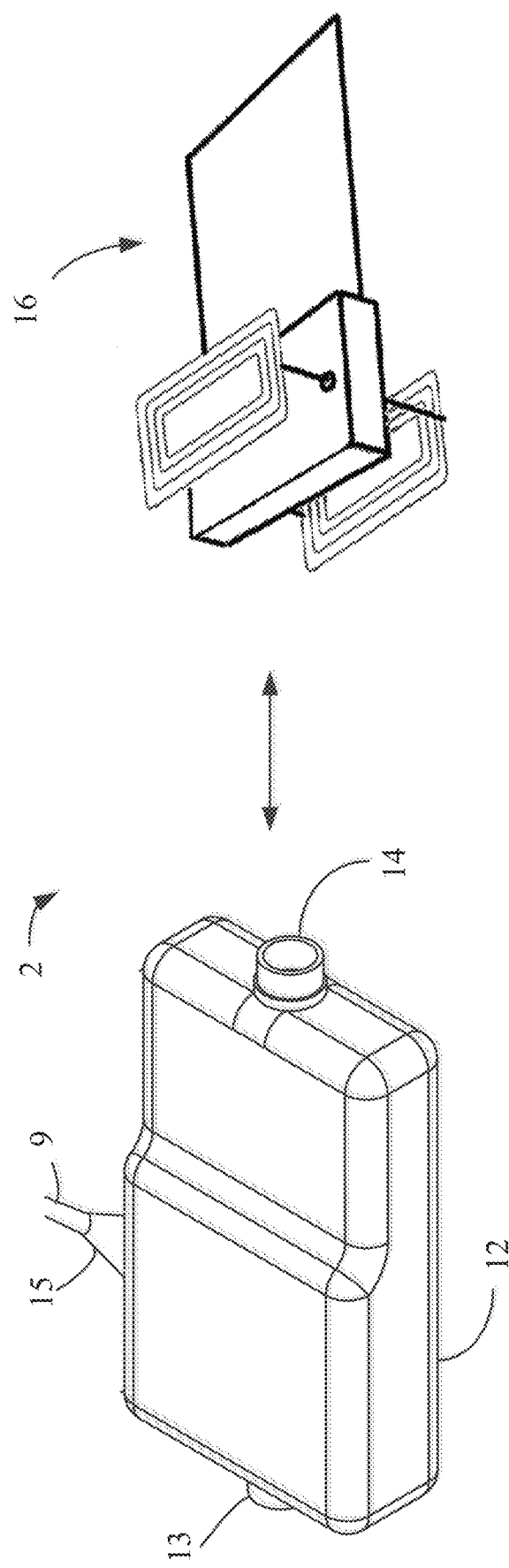

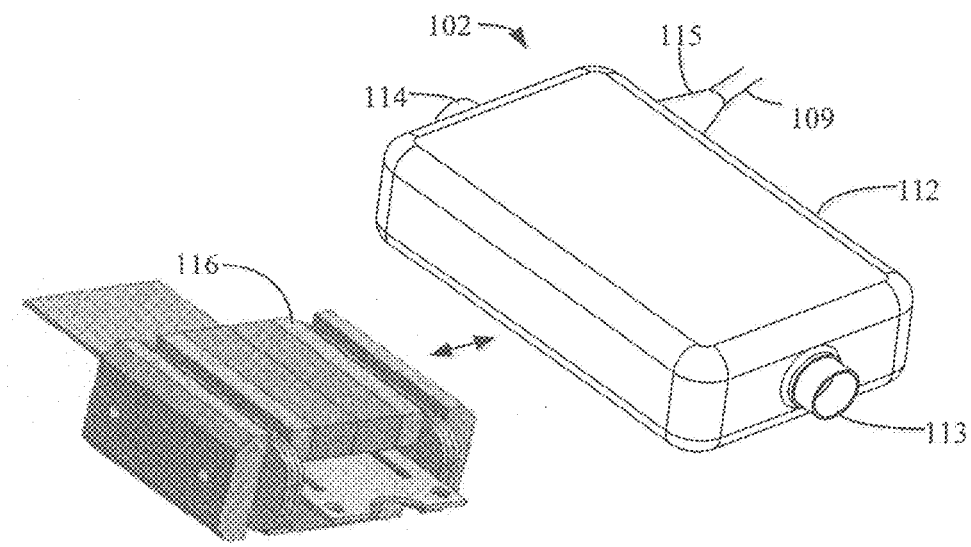
FIG. 18A
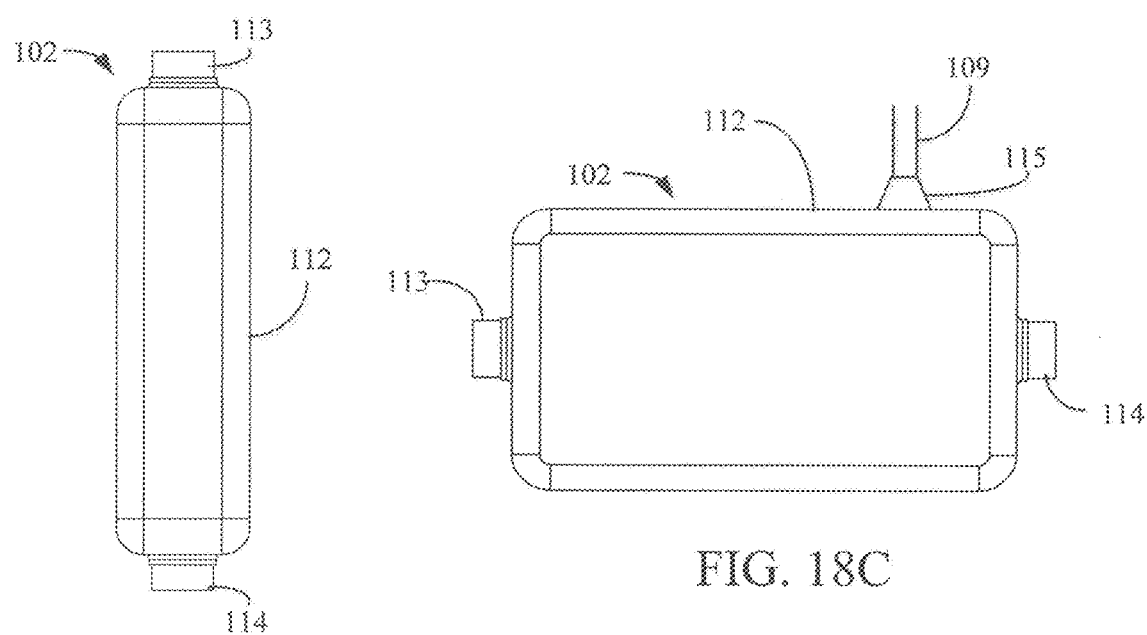
FIG. 18B
FIG. 18C

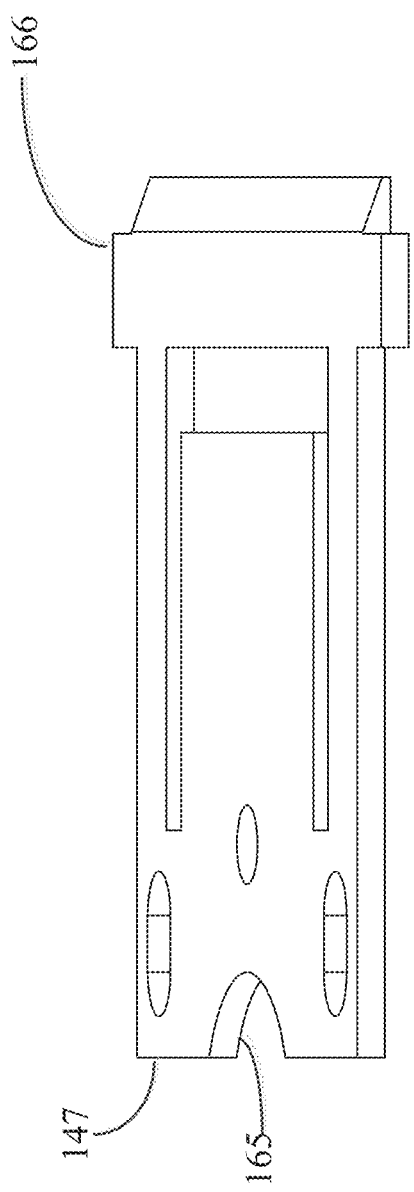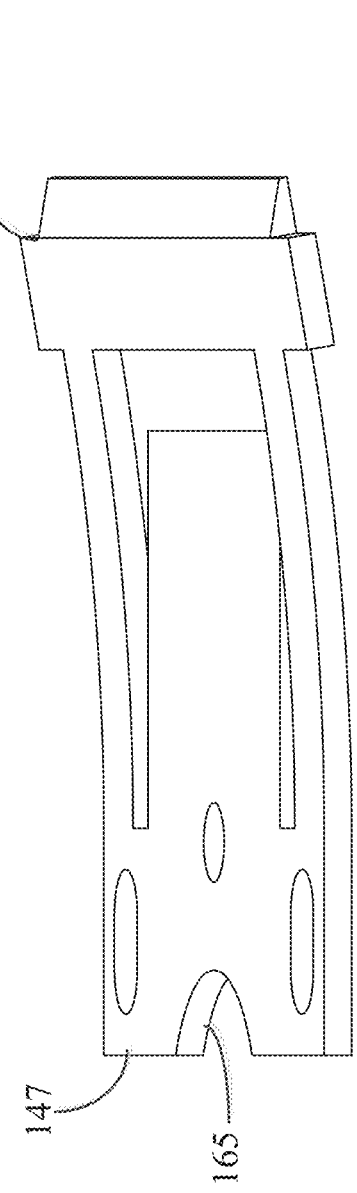

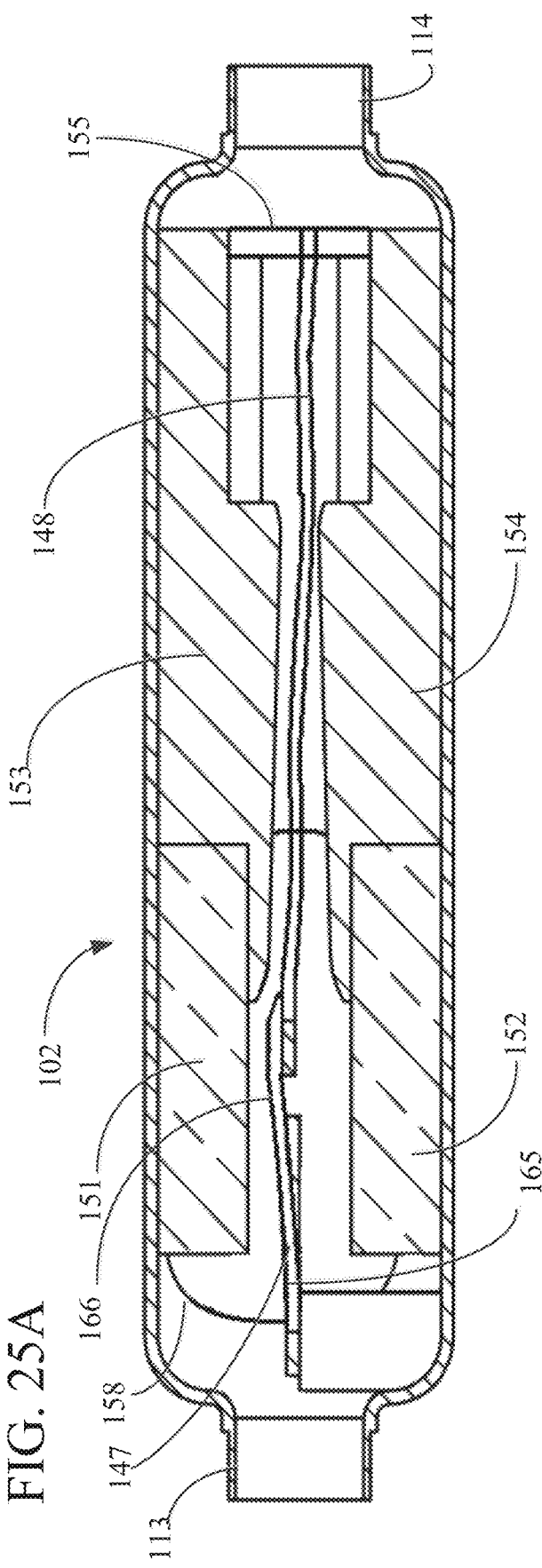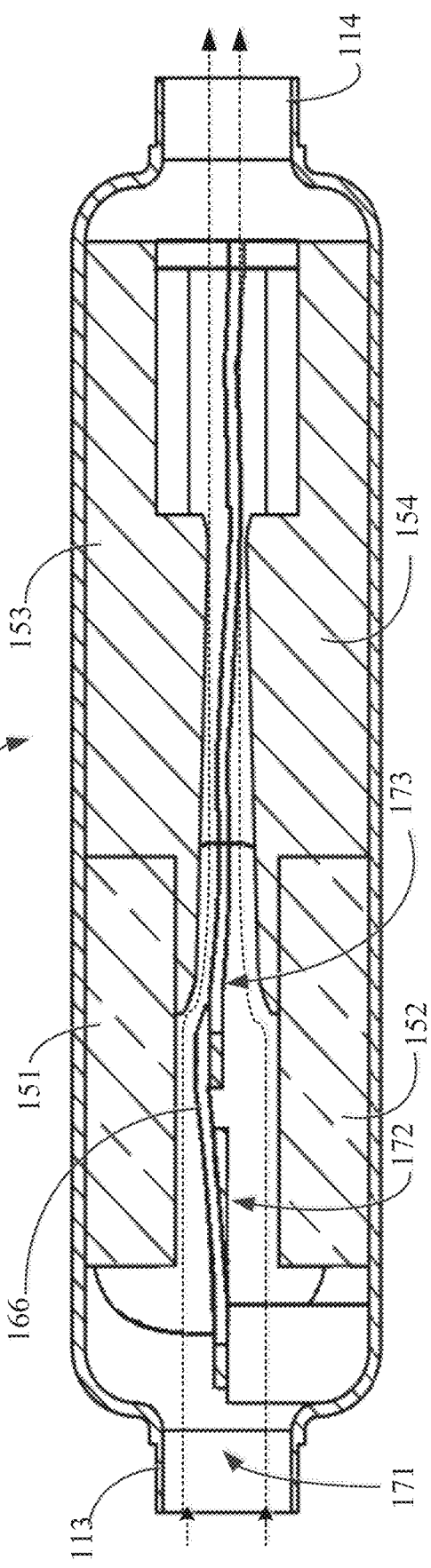

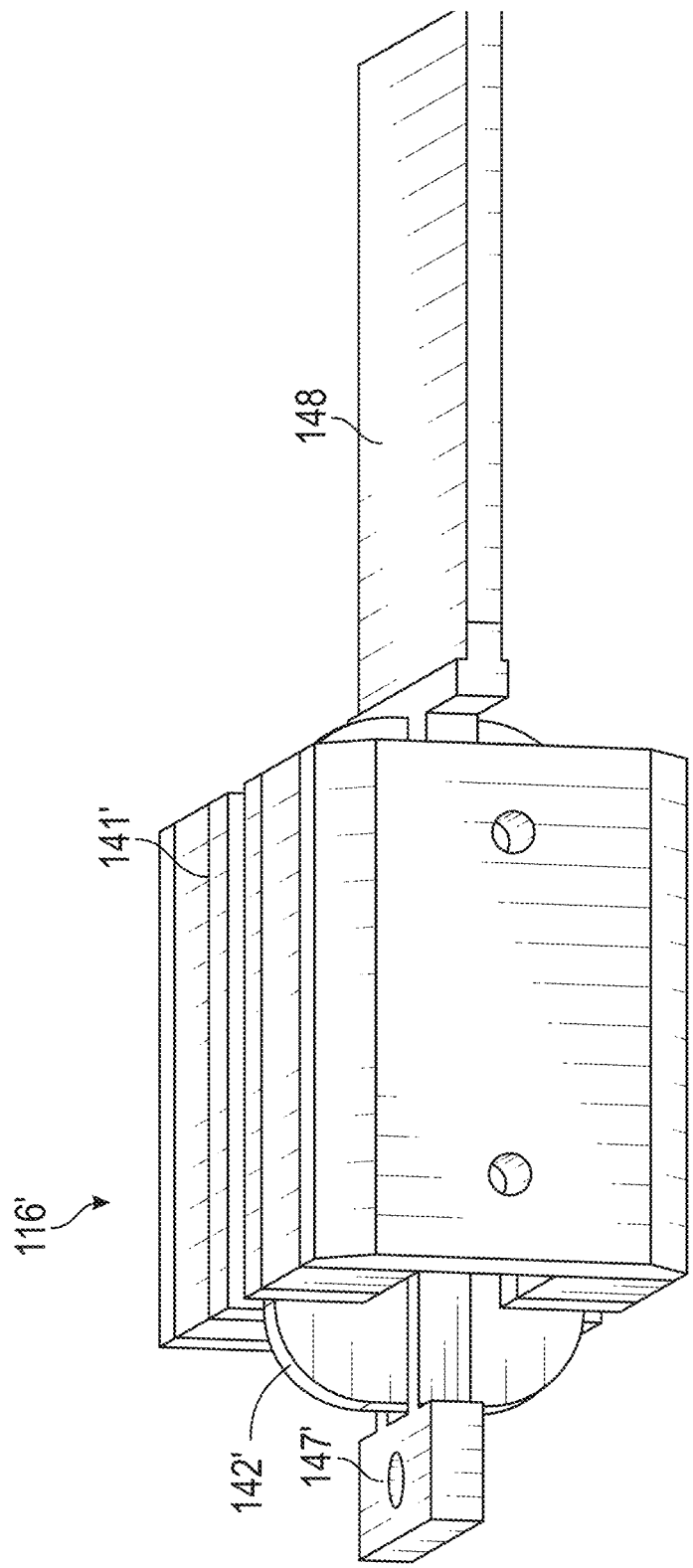

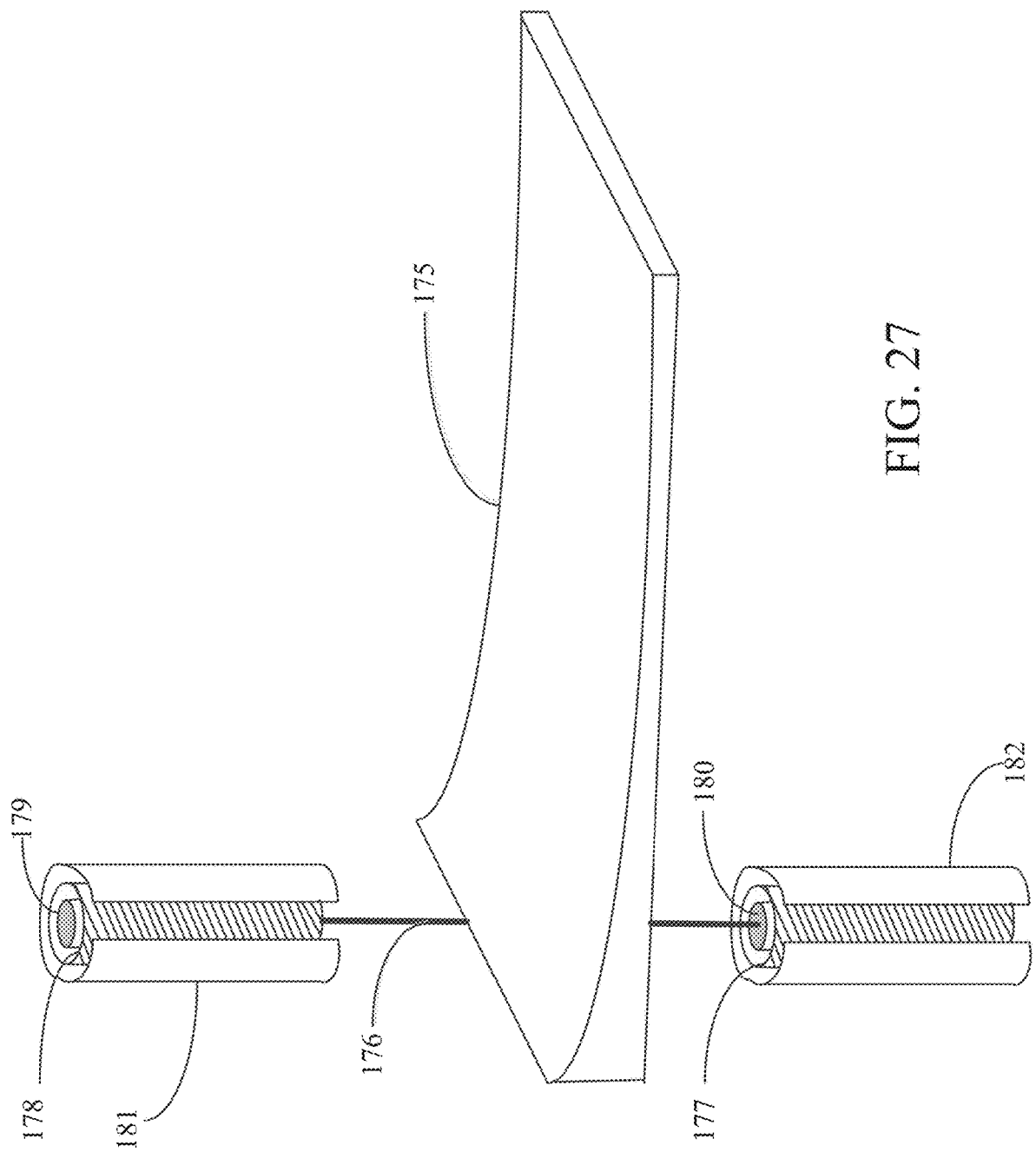

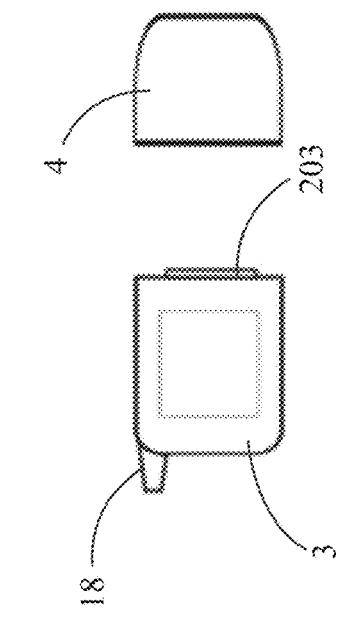
FIG. 30A
FIG. 30B
FIG. 30C
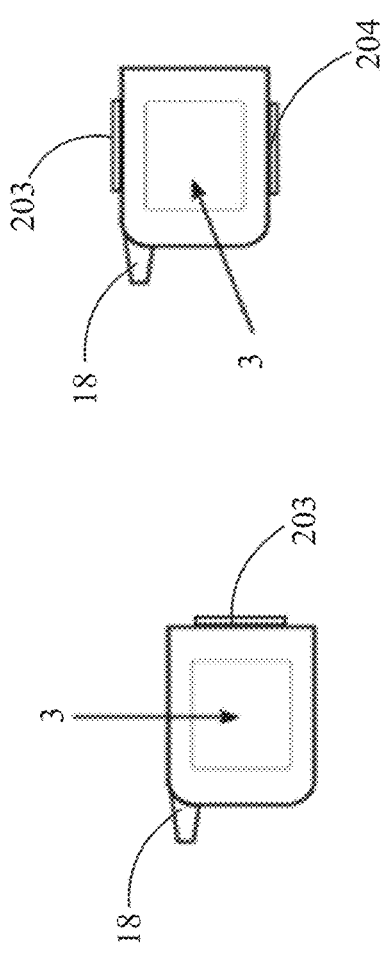
FIG. 30D
FIG. 30E
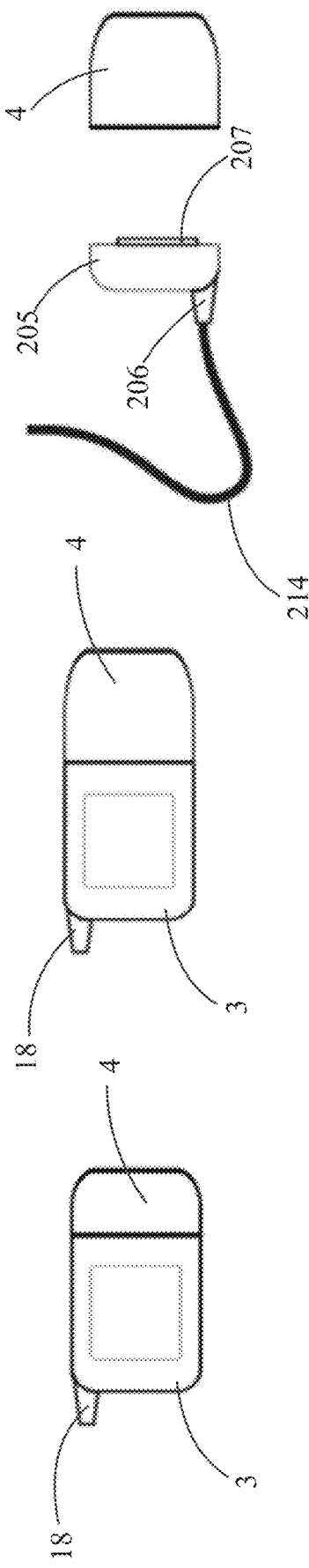
FIG. 30F

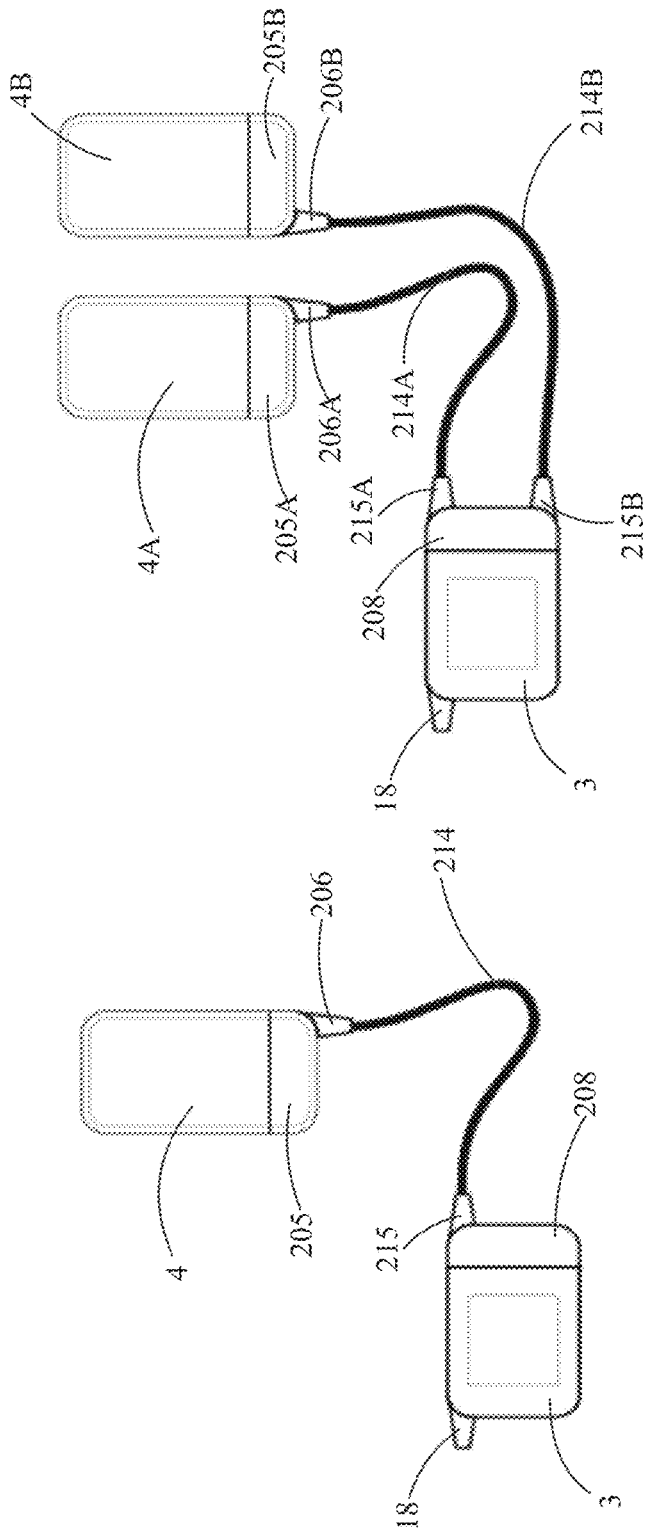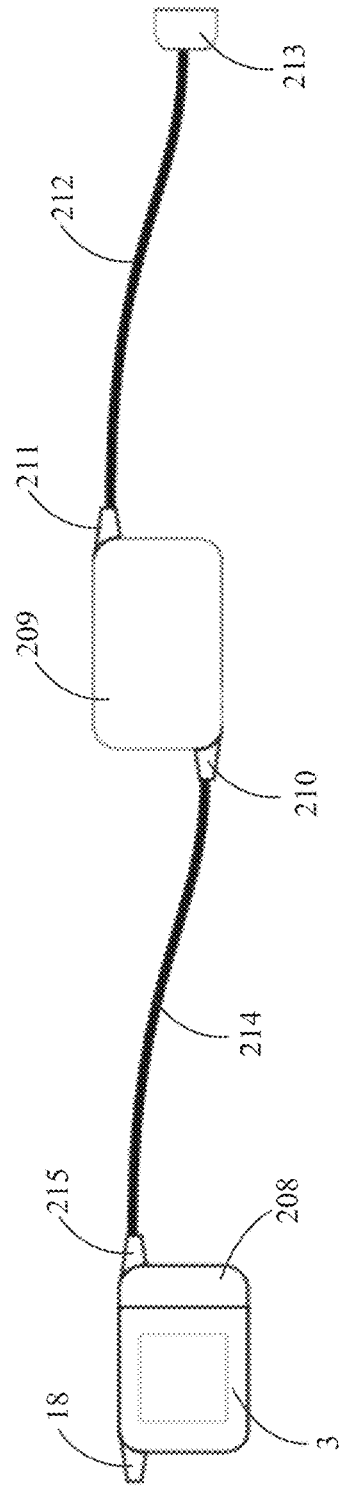
FIG. 30H
FIG. 30G
FIG. 30I

IMPLANTABLE PUMP SYSTEM HAVING A RECTANGULAR MEMBRANE

CROSS-REFERENCE TO RELATED APPLICATIONS

This application is a continuation of U.S. patent application Ser. No. 15/940,856, filed Mar. 29, 2018, now U.S. Pat. No. 10,933,181, which claims priority to U.S. Provisional Application Ser. No. 62/592,349, filed Nov. 29, 2017, U.S. Provisional Application Ser. No. 62/505,023, filed May 11, 2017, and U.S. Provisional Application Ser. No. 62/480,333, filed Mar. 31, 2017, the entire contents of each of which are incorporated herein by reference.

FIELD OF THE INVENTION

The present invention relates generally to heart pumps and more particularly to implantable pumps having an approximately rectangular profile that employ a membrane to propel blood through the pump.

BACKGROUND

The human heart is comprised of four major chambers with two ventricles and two atria. Generally, the right-side heart receives oxygen-poor blood from the body into the right atrium and pumps it via the right ventricle to the lungs. The left-side heart receives oxygen-rich blood from the lungs into the left atrium and pumps it via the left ventricle to the aorta for distribution throughout the body. Due to any of a number of illnesses, including coronary artery disease, high blood pressure (hypertension), valvular regurgitation and calcification, damage to the heart muscle as a result of infarction or ischemia, myocarditis, congenital heart defects, abnormal heart rhythms or various infectious diseases, the left ventricle may be rendered less effective and thus unable to adequately pump oxygenated blood throughout the body.

The Centers for Disease Control and Prevention (CDC) estimates that about 5.1 million people in the United States suffer from some form of heart failure. Heart failure is generally categorized into four different stages with the most severe being end stage heart failure. End stage heart failure may be diagnosed where a patient has heart failure symptoms at rest in spite of medical treatment. Patients may have systolic heart failure, characterized by decreased ejection fraction. In patients with systolic heart failure, the walls of the ventricle are weak and do not squeeze as forcefully as a healthy patient. Consequently, during systole a reduced volume of oxygenated blood is ejected into circulation, a situation that continues in a downward spiral until death. Patients may alternatively have diastolic heart failure (HFpEF) wherein the heart muscle becomes stiff or thickened making it difficult for the affected chamber to fill with blood. A patient diagnosed with end stage heart failure has a one-year mortality rate of approximately 50%.

There is a category of patients who exhibit an advanced stage of heart failure but have not yet achieved end stage heart failure. Patients in this category may have severely symptomatic heart failure but some preserved end-organ function. Typically, the condition of these patients deteriorates rapidly over a short period of time and may ultimately require a left ventricular assist device (LVAD) and/or a heart transplant. Presently, the only alternative to a heart transplant is a mechanical implant. While in recent years mechanical implants have improved in design, typically such implants will prolong a patient's life by a few years at most, and include a number of co-morbidities.

Fortunately, patients who have not yet reached end stage heart failure may avoid or prolong a full-support LVAD and/or heart transplant by implantation of a smaller pump. Patients in this category whose condition does not yet warrant a conventional full-support LVAD could be treated effectively with partial-support assist devices providing partial flow support and requiring less invasive surgery. For comparison, implantation of an LVAD device typically requires sternotomy and cardiopulmonary bypass.

One such partial-support assist device is the CircuLite Synergy Micro-pump device. The CircuLite Synergy Micro-pump device provides partial flow support and may serve as a bridge to LVAD implantation or heart transplantation. The CircuLite device, similar to the devices described in at least U.S. Pat. Nos. 6,116,862 and 8,512,012, has a cylindrical shape similar to a AA battery and incorporates a rotary pump having an impeller. The pump is designed to move up to 3 liters of blood per minute and to deliver oxygenated blood directly from the left atrium to the subclavian artery. See P. Mohite, A Sabashnikov, A. Simon, A Weymann, N. Patil, B. Unsoeld, C. Bireta and A. Popov, *Does CircuLite Synergy assist device as partial ventricular support have a place in modern management of advanced heart failure?*, Expert Rev. Med. Devices, published online 2 Dec. 2014, pages 1-12. To connect the pump to the patient's vasculature, an ePTFE graft is positioned between the pump outlet and the subclavian artery to delivery oxygenated blood thereto, while an inflow cannula is surgically connected between the pump inlet and the left atrium.

While the CircuLite device offers patients an alternative that provides clinical benefits, several problems with the device have been documented. One problem observed during clinical testing of the CircuLite device is failure due to thrombosis. Id. The CircuLite device employs an impeller and has a size comparable to that of a AA battery, roughly 14 mm×49 mm. To produce an output flow of up to 3 liters of blood per minute, the impeller—which has a diameter of roughly 14 mm—must be rotated at high RPM. However, the higher the RPMs, the greater the shear stress applied to the blood and thus the greater the risk of thrombosis.

Yet another problem with the CircuLite device is the configuration of the inflow cannula and the need to insert the inlet into the left atrium. Unlike the left ventricle, which is thick and muscular, the atrial wall is relatively thin and fragile. For this reason, an inflow cannula ring cannot be used to fix the cannula to the heart chamber. As a result, it was observed that the cannula insertion site is prone to leakage. Id. Also, with a diameter of roughly 14 mm, and a mostly circular cross-section, the CircuLite device noticeably protrudes from the chest of the patient, which some patients may find unaesthetic.

Other partial-support pump devices suffer from problems similar to the CircuLite Synergy device. HeartWare produces a device similar to the CircuLite device, but which has a diameter of 20 mm. The HeartWare product is believed to suffer from the same shortcomings as the CircuLite device.

Other partial-support pump devices have a cylindrical shape and utilize a centrifugal pump having an impeller such as the one described in U.S. Pat. No. 6,723,039 which is assigned to CircuLite and Foundry LLC. The implantable pump described in the '039 patent provides partial circulatory support much like the CircuLite Synergy device. Yet, another partial-support pump device is Abiomed's Symphony device, which employs a centrifugal pump and is also implanted in the chest region.

Other types of partial-support pump devices are known that accelerate blood axially. For example, Abiomed's Impella pump, similar to the pump described in U.S. Pat. No. 7,736,296, is cylindrical in shape and pulls blood into an inlet area at one end. As described in the '296 patent, the pump involves an axial flow pump having a number of blades extending from a hub that accelerate the blood, which is expelled from an opposing end. While Abiomed's Impella pump is intended to be implanted in the left ventricle and aorta, a similar device by Procyrion, the Aortix device, works in a similar fashion but is an intra-aortic pump that is suspended in the aorta. U.S. Pat. Nos. 8,012,079 and 9,572,915 to Procyrion describe pumps similar to the Aortix device and discuss axial flow pumps having an impeller to propel blood from one of its ends to the other.

While all the foregoing devices are partial-support pump devices that may result in clinical benefits, each of the partial-support pump devices share similar shortcomings with the CircuLite Synergy device. Specifically, each of these pumps have a relatively small blade or impeller that rotates at a high rate of speed to partially support blood circulation. For the reasons discussed above with regard to CircuLite, these pumps too are believed to present an increased risk of thrombosis caused by excessive shear stress and trauma to the blood cells, and risk of platelet activation. Furthermore pumps like the Abiomed's Symphony device generate an unpleasant noise when in use.

Accordingly, there is a need for an energy efficient implantable pump having light weight, small size, and a delivery mechanism for partially support blood circulation with minimal blood damage.

SUMMARY OF THE INVENTION

The present invention overcomes the drawbacks of previously-known partial-support assist devices and methods by providing an implantable pump system having an undulating membrane capable of producing a wide range of flow rates while applying low shear forces to the blood, thereby reducing hemolysis and platelet activation relative to previously-known systems.

In accordance with one aspect of the invention, the implantable blood pump system includes an implantable pump, a controller and a rechargeable battery, each electrically coupled to one another. The system further may comprise a programmer that communicates with the controller to set and change pumping parameters.

The implantable blood pump may be used in a partial-support assist device. The implantable pump may include a housing, a rectangular membrane disposed within the housing, a magnet assembly disposed within the housing including one or more magnets, and an electromagnetic assembly disposed within the housing. The housing has an inlet and an outlet and is configured to be implanted within a patient, preferably to be in fluidic communication with the heart. The electromagnetic assembly may generate, when electrically activated, a magnetic field applied to the one or more magnets to induce wave-like deformation of the rectangular membrane, thereby pumping blood from the inlet, along the rectangular membrane, and out the outlet.

The electromagnetic assembly may include a first electromagnet portion and a second electromagnet portion. The magnet assembly may be disposed between the first electromagnet portion and the second electromagnet portion. The first electromagnet portion and the second electromagnet portion may be electrically activated independently. The first electromagnet portion and the second electromagnet portion may generate the magnetic field having a polarity that is dependent on direction of current in each of the first electromagnet portion and the second electromagnet portion. The first electromagnet portion and the second electromagnet portion may exhibit the same polarity or different polarities when the current is applied in the same direction. Alternating current applied to the electromagnetic assembly may cause the magnet assembly to reciprocate thereby causing the rectangular membrane to reciprocate to induce the wave-like deformation.

The implantable blood pump constructed in accordance with the principles of the present invention may have a generally rectangular housing having rounded or beveled edges and an inlet and an outlet. The implantable blood pump has a membrane assembly including a rectangular membrane suspended in the rectangular housing by a moving magnet at one end and guide posts at the other. To propel blood from the inlet to the outlet, the moving magnet is attracted to an electromagnetic assembly also disposed within the housing. The electromagnetic assembly may include a first electromagnet portion and a second electromagnet portion, arranged such that the first electromagnet portion is positioned above the moving magnet and the second electromagnet portion is positioned below the moving magnet.

An electrical signal may be sent to the electromagnet portions from the controller and/or battery that causes the electromagnetic portions to generate a magnetic field and thus attract the moving magnet to either the first electromagnet portion or the electromagnetic portion. The moving magnet may move toward either the first electromagnet portion or the second electromagnet portion. The current applied to the electromagnetic assembly may then be reversed, attracting the moving magnet to the other electromagnetic portion. By alternating the current applied to the electromagnet portions, and thus causing the moving magnet to move toward either the first or second electromagnet portions, wavelike deformations may be induced in the rectangular membrane. When blood is delivered to rectangular membrane the wavelike deformations may transfer energy to the blood thereby propelling the blood along the top and bottom of rectangular membrane and ultimately out of outlet of the implantable pump. The blood may be directed through and outlet cannula to the right subclavian artery or other artery to deliver oxygenated blood to the rest of the body.

The electromagnetic assembly may include a first electromagnet portion and a second electromagnet portion that cause the magnet assembly to reciprocate between first electromagnet portion and the second electromagnet portion. The wave-like deformations in the rectangular membrane may propagate along the rectangular membrane from an end of the rectangular membrane coupled to the magnet assembly towards an opposing end of the rectangular membrane. The electromagnetic assembly may generate the magnetic field to pump the blood at a blood flow rate, and the electromagnetic assembly may generate an adjusted magnetic field by manipulating the current applied to the electromagnetic assembly to adjust the blood flow rate. The electromagnetic assembly may generate the magnetic field to pump the blood at the blood flow rate between 1 and 5 liters per minute.

The implantable pump may include a mounting structure disposed within the housing and secured to the housing. The magnet assembly may move within the housing along linear guides secured to the mounting structure. The mounting structure may be rectangular in shape and include a circular inlet through a surface of the mounting structure to permit blood flow through the mounting structure.

The implantable pump may have a membrane assembly disposed within the housing that includes a mounting structure secured to the housing and a membrane holder secured to the mounting structure at one end of the membrane holder and coupled to the rectangular membrane at an opposing end of the membrane holder. The membrane holder may include a portion configured to be affixed to the mounting structure and a flexible portion configured to be coupled to the rectangular membrane. The membrane holder may be electromagnetic and in electrical communication with the electromagnetic assembly. The membrane assembly may include a membrane clamp configured to couple the membrane to the membrane holder. The membrane clamp may be electromagnetic and in electrical communication with the electromagnetic assembly.

The implantable pump may include a funnel assembly disposed within the housing adjacent to the outlet. The funnel assembly may have a top funnel portion and a bottom funnel portion, the top funnel portion positioned over at least a portion of the rectangular membrane and the bottom portion positioned below at least a portion of the rectangular membrane. The top surface of the bottom funnel portion and the bottom surface of the top funnel portion may provide a flow channel that narrows as the flow channel nears the outlet of the housing. The implantable pump may include first and second guide posts each having a first end and a second end. The first and second guide posts may span a distance between the top and bottom funnel portions, the first end of the first and second guide posts coupled to the bottom funnel portion and the second end of the first and second guide posts coupled to the top funnel portion such that the first and second guide posts are positioned parallel to one another. First and second guide post receiving portions may be included such that the first guide post receiving portion accepts the first guide post and the second guide post receiving portion accepts the second guide post. The first and second guide posts may keep the rectangular membrane in tension and to guide and permit movement of an end of the rectangular membrane along the first and second guide posts.

The magnet assembly may include a first magnet portion positioned above the rectangular membrane and a second magnet portion positioned below the rectangular membrane. The first magnet portion may have a polarity different from the second magnet portion, and the electromagnetic assembly may move towards or away the first magnetic portion or second magnetic portion responsive to the magnetic field. Alternating current applied to the electromagnetic assembly may cause the electromagnetic assembly and the rectangular membrane to reciprocate between the first magnet portion and the second magnet portion. The electromagnetic assembly may generate the magnetic field to pump the blood at a blood flow rate and the electromagnetic assembly may generate an adjusted magnetic field by manipulating a distance over which the electromagnetic assembly reciprocates between the first magnet portion and the second magnet portion to adjust the blood flow rate. The electromagnetic assembly may generate the magnetic field to pump the blood at a blood flow rate and the electromagnetic assembly may generate an adjusted magnetic field by manipulating a frequency by which the electromagnetic assembly reciprocates between the first magnet portion and the second magnet portion to adjust the blood flow rate.

The implantable blood pump further may include an inlet cannula coupled between the inlet and the patient's heart and an outlet cannula coupled between the outlet and the patient's subclavian artery.

In accordance with one aspect, a system for energizing the implantable blood pump is provided. The system may include a rechargeable battery configured to energize the implantable blood pump and an extracorporeal controller operatively coupled in electrical communication with the implantable blood pump via a percutaneous cable. The extracorporeal controller may include a power connector operatively coupled in electrical communication with the rechargeable battery. The power connector of the extracorporeal controller may be operatively coupled in electrical communication with the rechargeable battery directly.

The system may include an extension cable having a first end to be operatively coupled in electrical communication with the power connector of the extracorporeal controller, and a second end configured to be operatively coupled in electrical communication with the rechargeable battery. The power connector of the extracorporeal controller may be operatively coupled in electrical communication with the rechargeable battery remotely via the extension cable. The system also may include a second extension cable having a first end configured to be operatively coupled in electrical communication with the power connector of the extracorporeal controller, and a second end configured to be operatively coupled in electrical communication with a second rechargeable battery.

The extracorporeal controller may have an internal battery configured to energize the implantable blood pump when the rechargeable battery is decoupled from the power connector of the extracorporeal controller. The extracorporeal controller may include a second power connector configured to be operatively coupled in electrical communication with a second rechargeable battery. The system may include a power supply configured to be operatively coupled in electrical communication with the power connector of the extracorporeal controller when the rechargeable battery is decoupled from the power connector of the extracorporeal controller.

A system for use with the implantable blood pump is also provided where the system includes a controller electrically coupled to the electromagnetic assembly. The controller electrically activates the electromagnetic assembly to cause generation of the magnetic field. The controller may be implanted subcutaneously.

In accordance with one aspect, the implantable blood pump has a membrane assembly including a rectangular membrane suspended in the rectangular housing by a membrane holder secured to the rectangular housing by a mounting structure. To propel blood from the inlet to the outlet, the rectangular membrane is connected to at least one electromagnetic winding which is cause to move toward the magnet assembly also disposed within the rectangular housing. The magnet assembly may include a first magnet portion and a second magnet portion, arranged such that the first magnet portion is positioned above a portion of the rectangular membrane and the electromagnetic winding and the second magnet portion positioned below a portion of the rectangular membrane and the electromagnetic winding.

An electrical signal may be sent to the electromagnetic winding from the controller and/or battery that causes the electromagnetic winding to generate a magnetic field and thus move toward either the first magnet portion or the second magnet portion. The electromagnetic winding may move toward either the first magnet portion or the second magnet portion, thereby moving the rectangular membrane connected to the electromagnetic winding toward either the first magnet portion or the second magnet portion. The current applied to the electromagnetic winding may then be reversed, attracting the electromagnetic winding and the rectangular membrane to the other magnet portion. By alternating the current applied to the electromagnetic winding, the electromagnet winding is caused to move thereby causing wavelike deformations may be induced in the rectangular membrane. When blood is delivered to rectangular membrane the wavelike deformations may transfer energy to the blood thereby propelling the blood along the top and bottom of rectangular membrane and ultimately out of outlet of the implantable pump. The blood may be directed through and outlet cannula to the right subclavian artery or other artery to deliver oxygenated blood to the rest of the body.

Methods of implanting and using the implantable pump are also provided herein.

BRIEF DESCRIPTION OF THE DRAWINGS

FIG. 3 depicts the endovascular implantation approach for the implantable pump.

FIGS. 4A-C are perspective views of the implantable pump of FIGS. 1-3.

FIGS. 18A-C are perspective views of an alternative implantable pump for use in the pump system of FIGS. 1-3.

FIGS. 22A and 22B are perspective views of the membrane holder of the pump assembly.

FIGS. 25A and 25B are cut-away cross sectional views of the pump assembly having an undulating membrane.

FIG. 26 is a perspective view of a single electromagnetic winding embodiment of the pump assembly.

FIG. 27 is a perspective view of a dual magnet electromagnetic actuator.

FIGS. 30A-H illustrates various configurations for coupling a battery to a controller of the present invention, and FIG. 30I illustrates a controller coupled to a power supply.

DETAILED DESCRIPTION

The implantable pump system of the present invention is particularly well-suited for use as a partial-support assist device and includes an undulating membrane pump particularly suitable for partial-support circulation in a patient having heart failure at a stage that does not warrant implantation of a left ventricle assist device (LVAD) or heart transplantation. The pump system may also be suitable for patients exhibiting heart failure with reduced ejection fraction (HFrEF) who in the later stage may benefit from an LVAD as well as patients that exhibit heart failure with preserved ejection fraction (HFpEF) who currently do not benefit from LVAD. An implantable pump system constructed in accordance with the principles of the present invention may include an implantable pump, a battery and controller as well as an extracorporeal programmer. The implantable pump preferably includes a housing having an inlet and an outlet, a flexible membrane, and an electromagnetic actuator having electromagnetic portions and a magnet portion. When configured as a partial-support assist device, an inlet cannula may be inserted into a patient's left atrium and an outlet cannula may be placed in fluid communication with the patient's subclavian artery. By activating the electromagnetic actuator within the implantable pump, the membrane is induced to undulate, thereby causing blood to be drawn into the pump through the inlet cannula and expelled through the outlet cannula into the subclavian artery. Flow rate and pulsatility may be manipulated by changing one or more of the frequency, amplitude and duty cycle of the electromagnetic actuator assembly.

The membrane pump described herein overcomes the shortcomings in the prior art by achieving desirable flow rates for partial circulatory support in a manner causing minimal blood damage, thereby avoiding the problems with thrombus formation that plagued earlier partial-support assist devices. The implantable pump described herein is an improvement over U.S. Pat. Nos. 6,361,284, 6,658,740, 7,323,961 and 9,080,564 to Drevet, the entire disclosures of each of which are incorporated herein by reference, which generally disclose vibrating membrane fluid circulators. More specifically, these patents disclose a deformable membrane disposed within a structure having an admission orifice and a delivery orifice. At the admission end, the membrane is attached to a member that provides an excitation force to the membrane, causing waves in the membrane to travel toward the delivery orifice, thereby transferring energy to fluid within the structure and ultimately directing the fluid out of the delivery orifice. The present invention incorporates the teachings of these patents into the implantable pump system described herein for use as a partial-support assist device.

Figure 1:
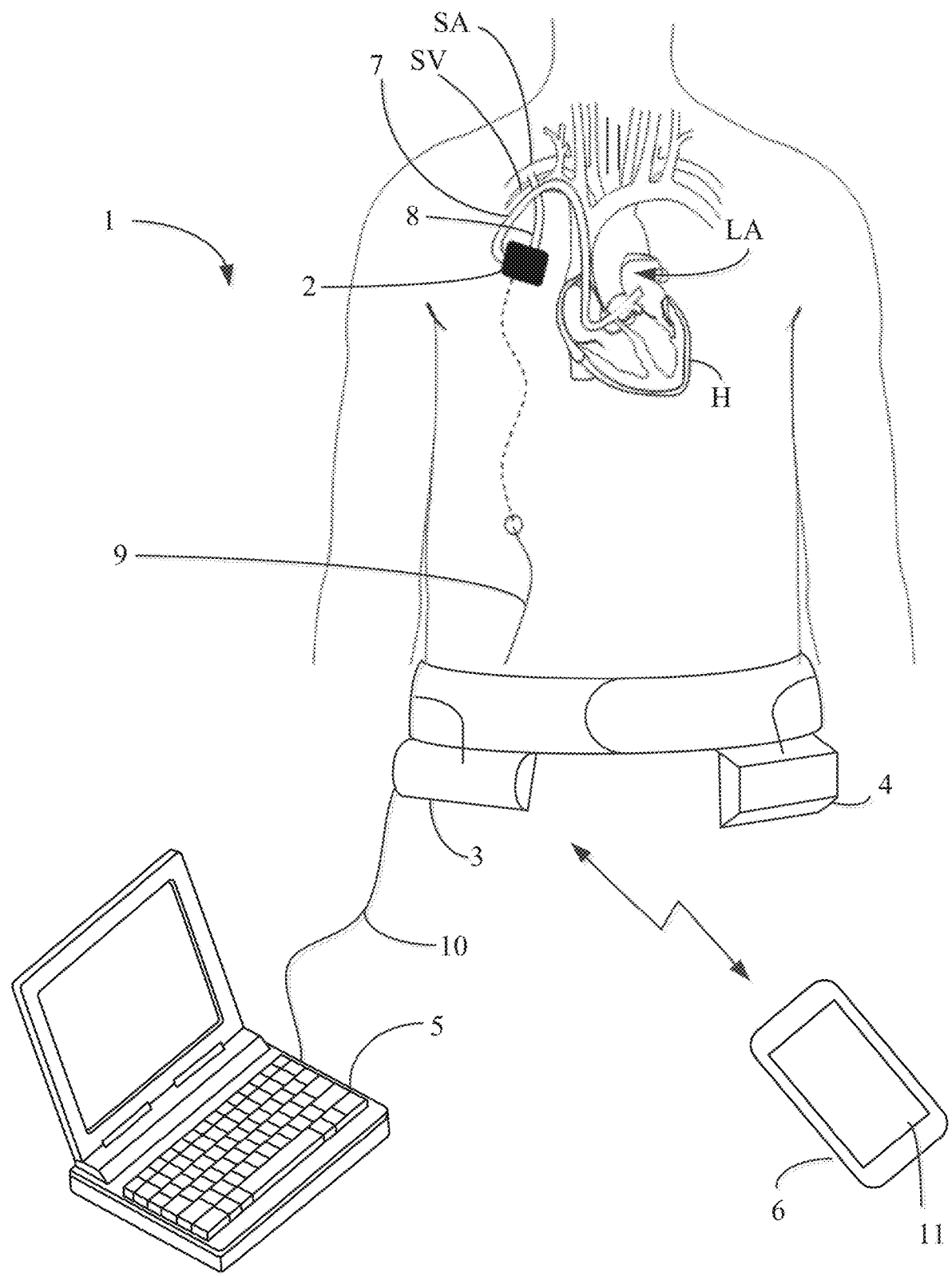
FIG. 1 depicts an exemplary embodiment of the pump system of the present invention comprising an implantable pump, controller, battery, programmer and mobile device.

Referring now to FIG. 1, pump system 1 constructed in accordance with the principles of the present invention is described. System 1 illustratively includes implantable pump 2, controller 3, battery 4, programmer 5 and optionally, a software module programmed to run on mobile device 6. Implantable pump 2 is configured to be implanted within the patient and may be positioned into a subcutaneous or intra-muscular pocket inferior to the subclavian artery and in front of the right pectoralis major muscle. Implantable pump 2 may be connected to inlet cannula 7 and outlet cannula 8. Inlet cannula 7 may connect implantable pump 2 to a first heart chamber or body lumen, e.g., the left atrium LA of heart H, and outlet cannula 8 may connect implantable pump to a second heart chamber or body lumen, e.g., the right subclavian artery SA. Outlet cannula 8, may be any kind of graft suitable for fluid communication between implantable pump 2 and subclavian artery SA. For example, outlet cannula 8 may be a ePTFE graft or other synthetic material.

Controller 3 and battery 4 may be extracorporeal and sized so as to be placed on a belt or garment worn by the patient, as illustrated in FIG. 1. Battery 4 may be electrically coupled to controller 3 via a cable that is integrated into the belt. Controller 3 and battery 4 may be two separate units or may be incorporated into the same unit. Where controller 3 and battery 4 are extracorporeal, cable 9 may be tunneled from the subcutaneous pocket to the right upper quadrant of the abdomen at which point cable 9 may exit the body. Accordingly, cable 9 may extend from the pump in the subcutaneous pocket, through the body of the patient to the abdomen and out the abdomen and to the extracorporeal controller 3 and/or battery 4 on the exterior of the body. In this manner, both controller 3 and battery 4 may be electrically coupled via cable 9 to implantable pump 2.

In an alternative embodiment, controller 3 and/or battery 4 may be enclosed within a biocompatible housing and sized to be implanted subcutaneously in the patient's abdomen or in any other suitable subcutaneous location. In this alternative embodiment, controller 3 and/or battery 4 may include a wireless transceiver for bi-directional communications with an extracorporeal programming device and/or charging device. Where battery 4 is implanted subcutaneously, a second extracorporeal battery may be worn by the patient near implanted battery 4 which may charge battery 4 transcutaneously. As will be understood, the foregoing alternative embodiment avoids the use of percutaneous cable 9, and thus eliminates a frequent source of infection.

Battery 4 preferably comprises a rechargeable battery capable of powering implantable pump 2 and controller 3 for a period of several hours or even days before needing to be recharged. Battery 4 may include a separate charging circuit, not shown, as is conventional for rechargeable batteries. Battery 4 preferably is disposed within a housing suitable for carrying on a belt or holster, so as not to interfere with the patient's daily activities. However, as explained above, battery may be implanted and thus battery may be disposed within a biocompatible housing.

Programmer 5 is programmed to execute programmed software routines on a computer (e.g., laptop computer, desktop computer, smartphone, tablet, smartwatch, etc.) for use by a clinician or medical professional, for configuring and providing operational parameters to controller 3. The configuration and operational parameter data is stored in a memory associated with controller 3 and used by the controller to control operation of implantable pump 2. As described in further detail below, controller 3 directs implantable pump 2 to operate at specific parameters determined by programmer 5. Programmer 5 may be coupled to controller 3 via cable 10. Using programmer 5, operational parameters of implantable pump 2 are set and periodically adjusted, e.g., when the patient visits the clinician.

In accordance with another aspect of the invention, mobile device 6, which may be a conventional laptop, smartphone, tablet, or smartwatch, may include an application program for bi-directionally and wirelessly communicating with controller 3, e.g., via WiFi or Bluetooth communications. Preferably, mobile device 6 is used by the patient or the patient's caretaker. The application program on mobile device 6 may be programmed to permit the patient to send instructions to controller 3 to modify or adjust a limited number of operational parameters of implantable pump 2 stored in controller 3. Alternatively or in addition, mobile device 6 may be programmed to receive from controller 3 and to display on screen 11 of mobile device 6, data relating to operation of implantable pump 2 or alert or status messages generated by controller 3.

Figure 2:
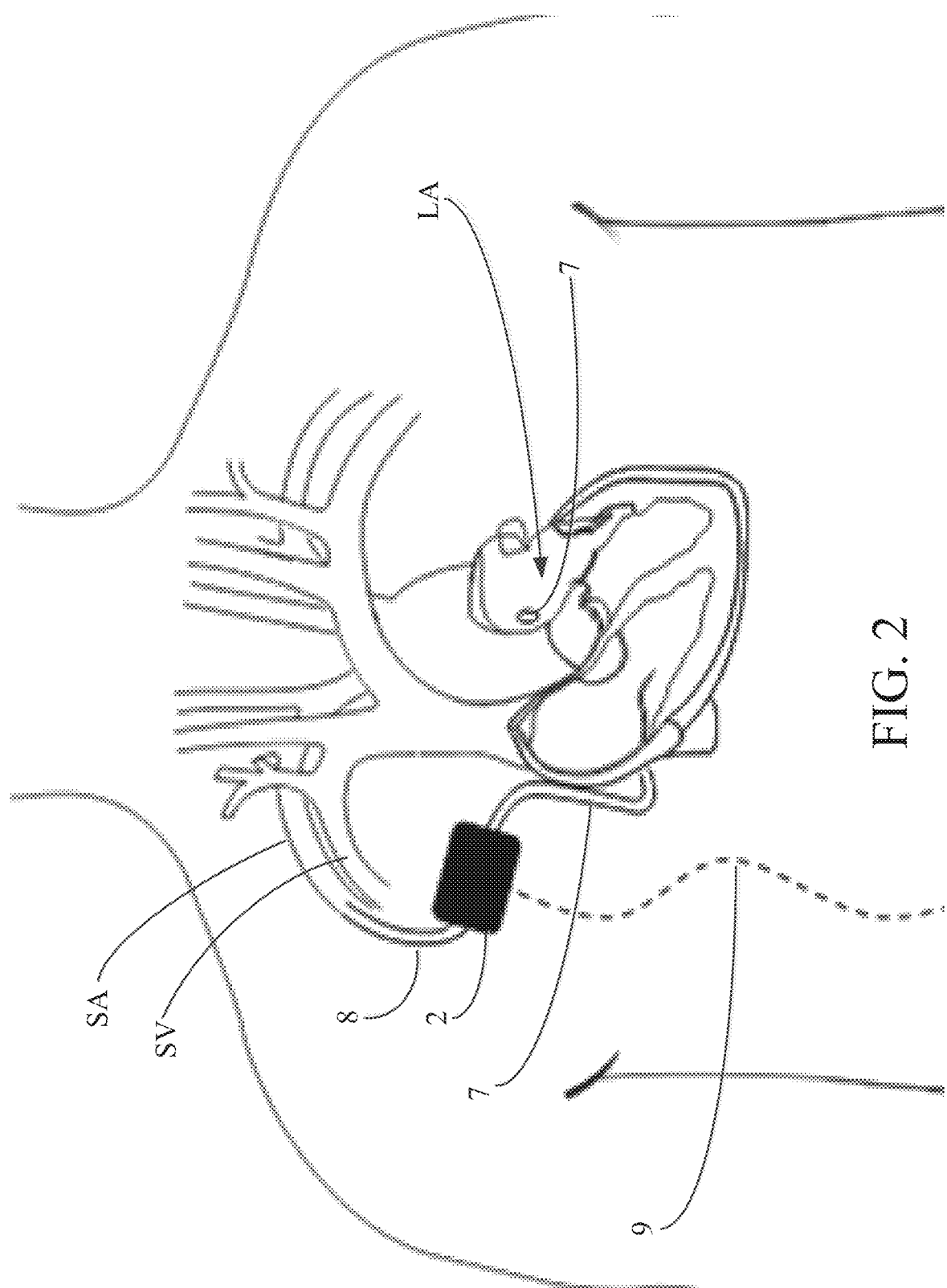
FIG. 2 depicts the surgical implantation approach for the implantable pump.

Referring now to FIG. 2, implantable pump 2 may be implanted using a surgical approach as is illustrated in FIG. 2. The surgical approach involves creating a subcutaneous pocket, e.g., at a position inferior to the subclavian artery and in front of the right pectoralis major muscle, in which implantable pump 2 is positioned. An incision is made in the right subclavian artery SA into which an end of outflow cannula 8 is positioned. Outflow cannula 8 may be anastomosed to the right subclavian artery SA. The opposing end of outflow cannula 8 is inserted into the subcutaneous pocket and coupled with implantable pump 2. To reach the heart, a mini-thoracotomy may be performed and pericardium is opened to insert an end of inflow cannula 7 into left atrium LA. Inflow cannula 7 may be secured to the left atrium using sutures. The opposing end of inflow cannula 7 may be tunneled through intercostal space and ultimately into the subcutaneous pocket to be coupled with implantable pump 2.

Alternatively, implantable pump 2 may be implanted using an endovascular approach, illustrated in FIG. 3. Like in the surgical approach, the endovascular approach involves creating a subcutaneous pocket, e.g., at a position inferior to the subclavian artery and in front of the right pectoralis major muscle, in which implantable pump 2 is positioned. The endovascular approach also involves an incision made in the right subclavian artery SA into which an end of outflow cannula 8 is positioned and anastomosed to the right subclavian artery SA. The opposing end of outflow cannula 8 may similarly be inserted into the subcutaneous pocket and coupled with implantable pump 2. However, unlike the surgical approach described above, to reach the right atrium, inflow cannula 7 is inserted through the right subclavian vein. In this approach, an incision is made in the right subclavian vein SV and a guidewire is inserted and advanced through the superior vena cava SVC to right atrium RA. Upon reaching right atrium RA, a transseptal puncture technique may be used to advance the guidewire into left atrium LA. Inflow cannula 7 may then be advanced to left atrium LA over the guidewire and may be anchored to the atrial septum.

Figure 4B:
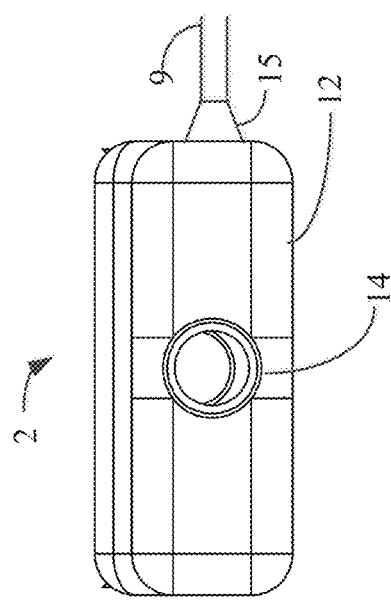
Figure 4C:
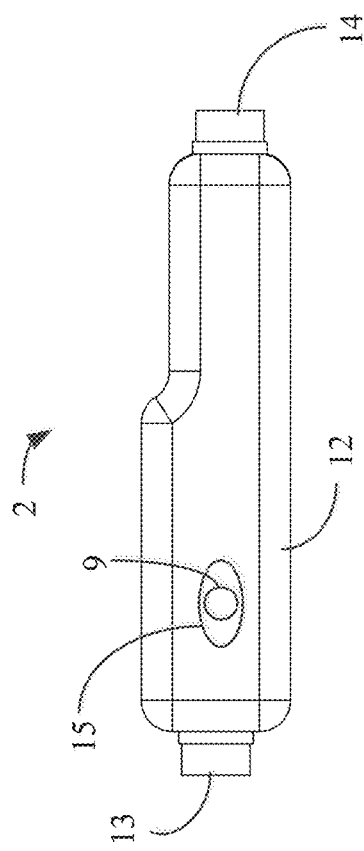

Referring now to FIG. 4A-4C, implantable pump 2 is illustrated in greater detail. Implantable pump 2 includes pump housing 12 which is made of a biocompatible material, such as titanium, and is sized to be implanted within a patient's chest as described above. Pump housing 12 may have a general rectangular shape or may narrow at one or both ends and may be two or more pieces that fit together by, for example, threads or welding, to form fluid tight pump housing 12. Pump housing 12 may have any size suitable for pump assembly 16 to be disposed within pump housing 12. Pump housing includes inlet 13 and outlet 14 through which blood may flow in and out, respectively. Pump housing 12 in FIG. 4C demonstrates a narrowing step-down feature to facilitate blood flow towards outlet 14. Pump also may include electrical port 15 to attach implantable pump 2 to cable 9. Electrical port 15 may permit cable 9 to transverse pump housing 12 and connect to pump assembly 16 in a fluid tight manner. Cable 9 may deliver electrical wires from controller 3 and battery 4 to pump assembly 16.

Figure 5A:
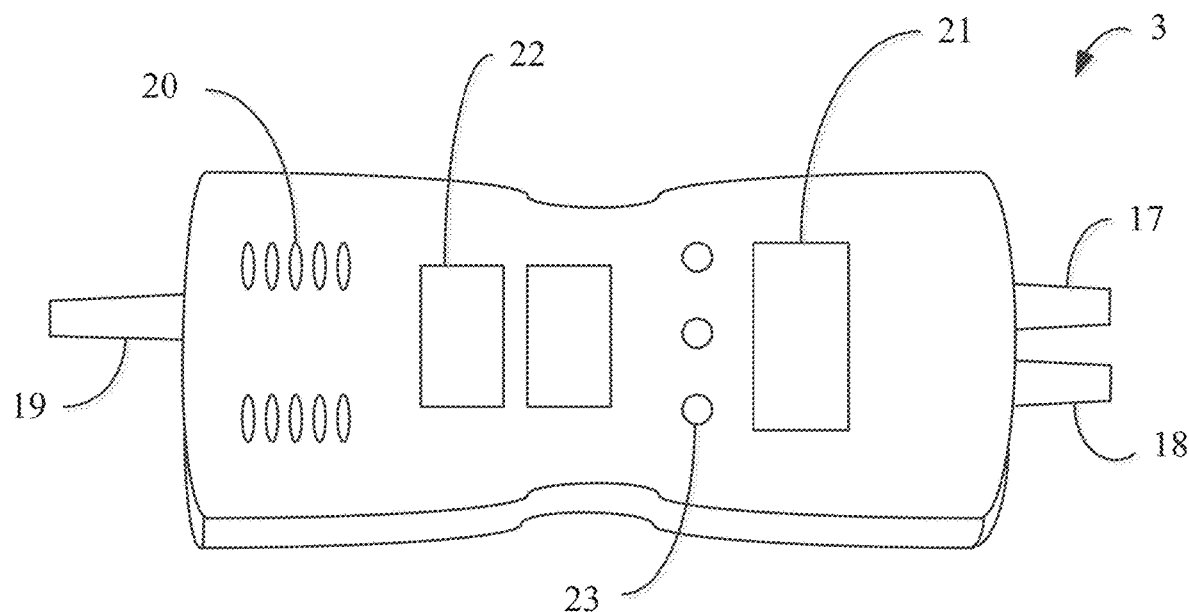
FIGS. 5A and 5B are, respectively, a perspective view and a schematic view of the electronic components of an exemplary embodiment of the controller.
Figure 5B:
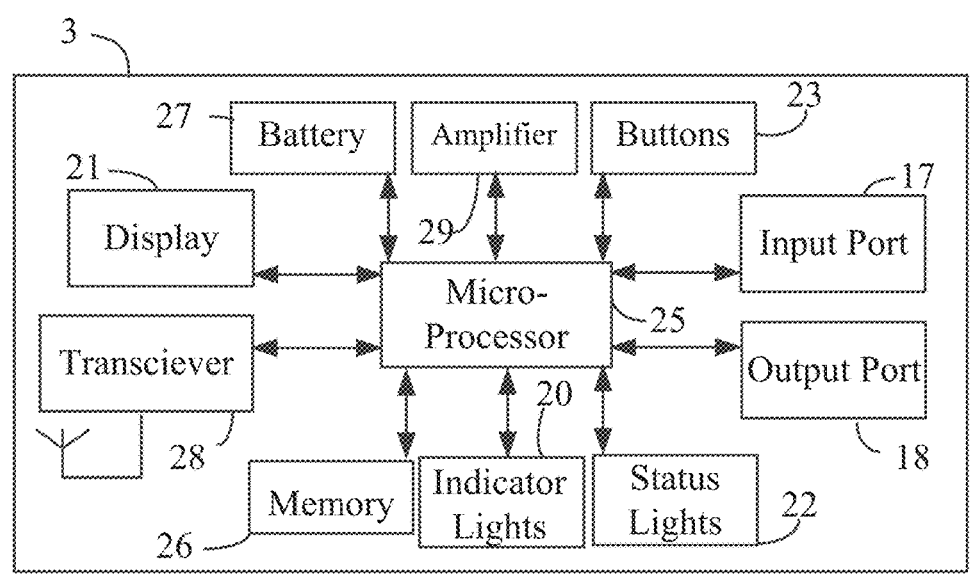

With respect to FIGS. 5A and 5B, controller 3 is illustrated in greater detail. As depicted in FIG. 1, controller 3 may be sized and configured to be worn on the exterior of the patient's body or may be sized and configured to be implanted subcutaneously. Controller 3 includes input port 17, output port 18, battery port 19, indicator lights 20, display 21, status lights 22 and buttons 23. Input port 17 is configured to periodically and removably accept cable 10 to establish an electrical connection between programmer 5 and controller 3, e.g., via a USB connection. In this manner, a clinician may couple to controller 3 to set or adjust operational parameters stored in controller 3 for controlling operation of implantable pump 2. In addition, when programmer 5 is coupled to controller 3, the clinician also may download from controller 3 data relating to operation of the implantable pump, such as actuation statistics, for processing and display on display 38 of programmer 5. Alternatively, or in addition, controller 3 may include a wireless transceiver for wirelessly communicating such information with programmer 5. In this alternative embodiment, wireless communications between controller 3 and programmer 5 may be encrypted with an encryption key associated with a unique identification number of the controller, such as a serial number.

Battery port 19 is configured to removably accept a cable connected to battery 4 which may be incorporated into the belt illustrated in FIG. 1. Battery 4 may be removed from the belt and disconnected from controller 3 to enable the patient to periodically replace the battery with a fully charged battery. It is expected that the patient will have available to him or her at least two batteries, so that while one battery is coupled to controller 3 to energize the controller and implantable pump 2, the other battery may be connected to a recharging station. Alternatively, or in addition, battery port 19 may be configured to accept a cable that is coupled directly to a power supply, such as a substantially larger battery/charger combination that permits the patient to remove battery 4 while lying supine in a bed, e.g., to sleep.

Output port 18 is electrically coupled to cable 9, which is coupled to implantable pump 2 through electrical port 15 of pump housing 12. Cable 9 provides energy to energize implantable pump 2 in accordance with the configuration settings and operational parameters stored in controller 3. Cable 9 also may permit controller 3 to receive data from sensors disposed in implantable pump 2. In one embodiment, cable 9 is designed to extend percutaneously and may be an electrical cable having a biocompatible coating. Cable 9 may be impregnated with pharmaceuticals to reduce the risk of infection, the transmission of potentially hazardous substances or to promote healing where it extends through the patient's skin.

As mentioned above, controller 3 may include indicator lights 20, display 21, status lights 22 and buttons 23. Indicator lights 20 may visually display information relevant to operation of the system, such as the remaining life of battery 4. Display 21 may be a digital liquid crystal display that displays real time pump performance data, physiological data of the patient, such as heart rate, and/or operational parameters of the implantable pump, such as the target pump pressure or flow rate, etc. When it is determined that certain parameter conditions exceed preprogrammed thresholds, an alarm may be sounded and an alert may be displayed on display 21. Status lights 22 may comprise light emitting diodes (LEDs) that are turned on or off to indicate whether certain functionality of the controller or implantable pump is active. Buttons 23 may be used to wake up display 21, to set or quiet alarms, etc.

With respect to FIG. 5B, the components of the illustrative embodiment of controller 3 of FIG. 5A are described. In addition to the components of controller 3 described in connection with FIG. 5A, controller 3 further includes microprocessor 25, memory 26, battery 27, optional transceiver 28 and amplifier circuitry 29. Microprocessor 25 may be a general purpose microprocessor, for which programming to control operation of implantable pump 2 is stored in memory 26. Memory 26 also may store configuration settings and operational parameters for implantable pump 2. Battery 27 supplies power to controller 3 to provide continuity of operation when battery 4 is periodically swapped out. Optional transceiver 28 facilitates wireless communication with programmer 5 and/or mobile device 6 via any of a number of well-known communications standards, including BLUETOOTH™, ZigBee, and/or any IEEE 802.11 wireless standard such as Wi-Fi or Wi-Fi Direct. Controller 3 may further include amplifier circuitry 29 for amplifying electrical signals transferred between controller 3 and implantable pump 2.

Figure 6:
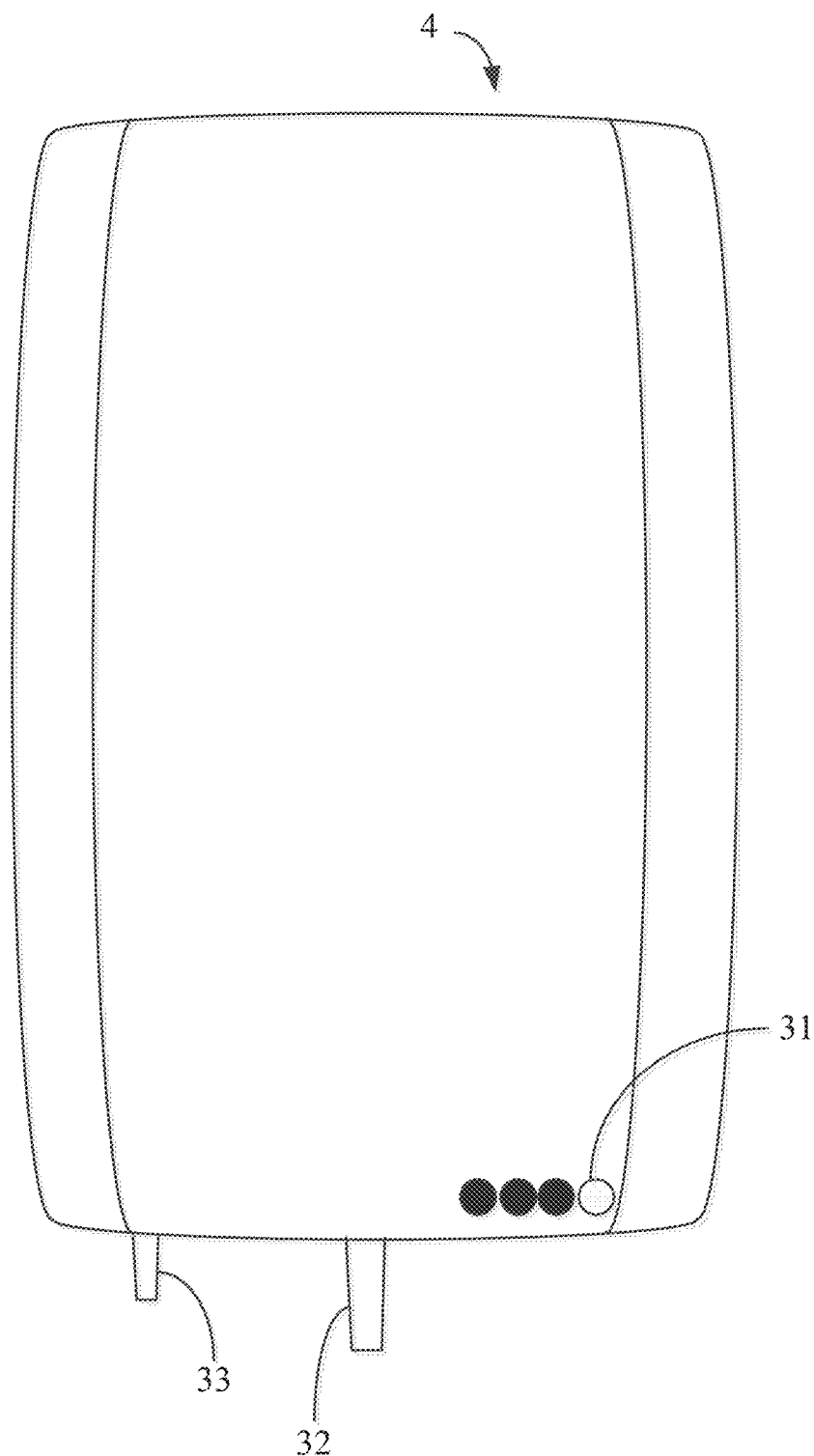
FIG. 6 is a plan view of an extracorporeal battery for use in the pump system.

Referring now to FIG. 6, battery 4 is described. Battery 4 provides power to implantable pump 2 and also may provide power to controller 3. As described above, battery 4 may be implanted subcutaneously or may be extracorporeal. Battery 4 may consist of a single battery or a plurality of batteries disposed within a housing, and when configured for extracorporeal use, is sized and configured to be worn on the exterior of the patient's body, such as on a belt. Alternatively, where battery 4 is implanted into a patient, battery 4 may be disposed in a biocompatible housing. Battery life indicator 31 may be provided on the exterior of battery 4 to indicate the remaining charge of the battery. Controller may be connected to battery 4 via a cable connecting battery port 19 of controller 3 to output port 32 of battery 4. In one embodiment, battery 4 may be rechargeable using a separate charging station, as is known in the art of rechargeable batteries. Alternatively, or in addition, battery 4 may include port 33 which may be removably coupled to a transformer and cable to permit the battery to be recharged using a conventional residential power outlet, e.g., 120/240V, 50/60 Hz AC power.

Figure 7A:
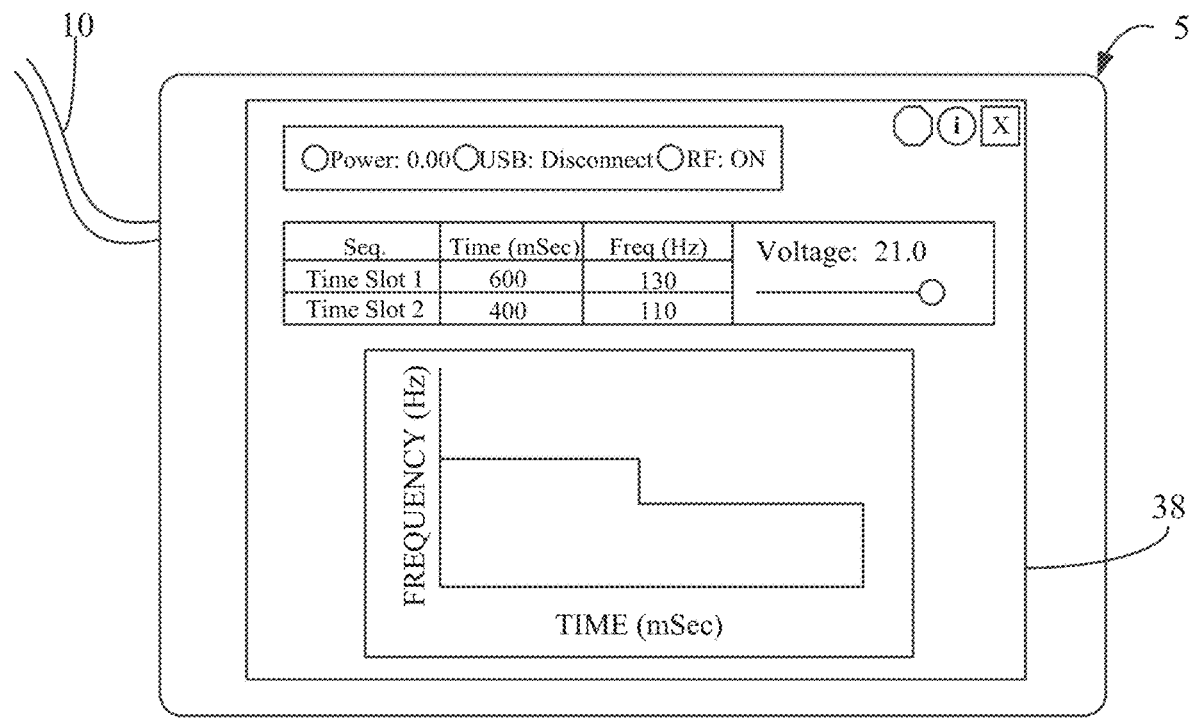
FIGS. 7A and 7B are, respectively, a perspective view and a schematic view of the electronic components of an exemplary embodiment of the programmer.
Figure 7B:
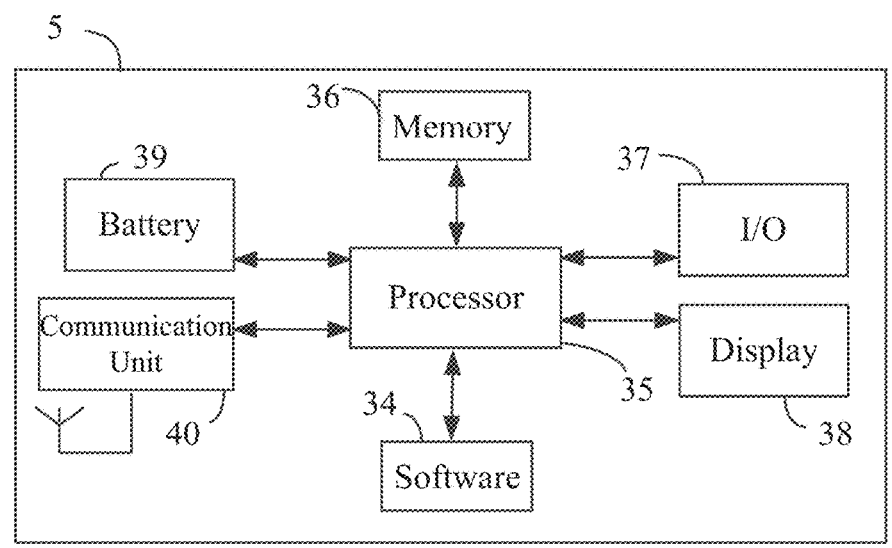

Referring now to FIGS. 7A-7B, programmer 5 is described. Programmer 5 may be a conventional laptop, desktop, tablet, smartphone, smartwatch loaded with programmed software routines 34 for configuring controller 3 and setting operational parameters that controller 3 uses to control operation of implantable pump 2. As discussed above, programmer 5 typically is located in a clinician's office or hospital, and is coupled to controller 3 via cable 10 or wirelessly to initially set up controller 3, and then periodically adjust controller 3 thereafter as required to adjust the operational parameters as may be needed. The operational parameters of controller 3 set using the programmed routines of programmer 5 may include but are not limited to applied voltage, pump frequency, pump amplitude, target flow rate, pulsatility, etc. When first implanted, the surgeon or clinician may use programmer 5 to communicate initial operating parameters to controller 3. Following implantation, the patient periodically may return to the clinician's office for adjustments to the operational parameters which may again be made using programmer 5.

Programmer 5 may be any type of conventional personal computer device having touch screen capability. As illustrated in FIG. 7B, programmer 5 preferably includes processor 35, memory 36, input/output device 37, display 38, battery 39 and communication unit 40. Memory 36 may be a non-transitory computer readable medium that stores the operating system for the programmer, as well as the programmed routines needed to communicate with controller 3. When executed by processor 35, instructions from the programmed routines stored on the non-transitory computer readable medium cause execution of the functionality described herein. Communication unit 40 may include any of a number of well-known communication protocols, such as BLUETOOTH™, ZigBee, and/or any IEEE 802.11 wireless standard such as Wi-Fi or Wi-Fi Direct. As illustrated in FIG. 7A, the programmed routines used to program and communicate with controller 3 also may provide data for display on the screen of programmer 5 identifying operational parameters with which controller 3 controls implantable pump 2. The programmed routines also may enable programmer 5 to download from controller 3 operational data or physiologic data communicated by the implantable pump and to display that information in real time while the programmer is coupled to the controller via a wired or wireless connection. The transferred data may then be processed and displayed on the screen of programmer 5.

Figure 8:
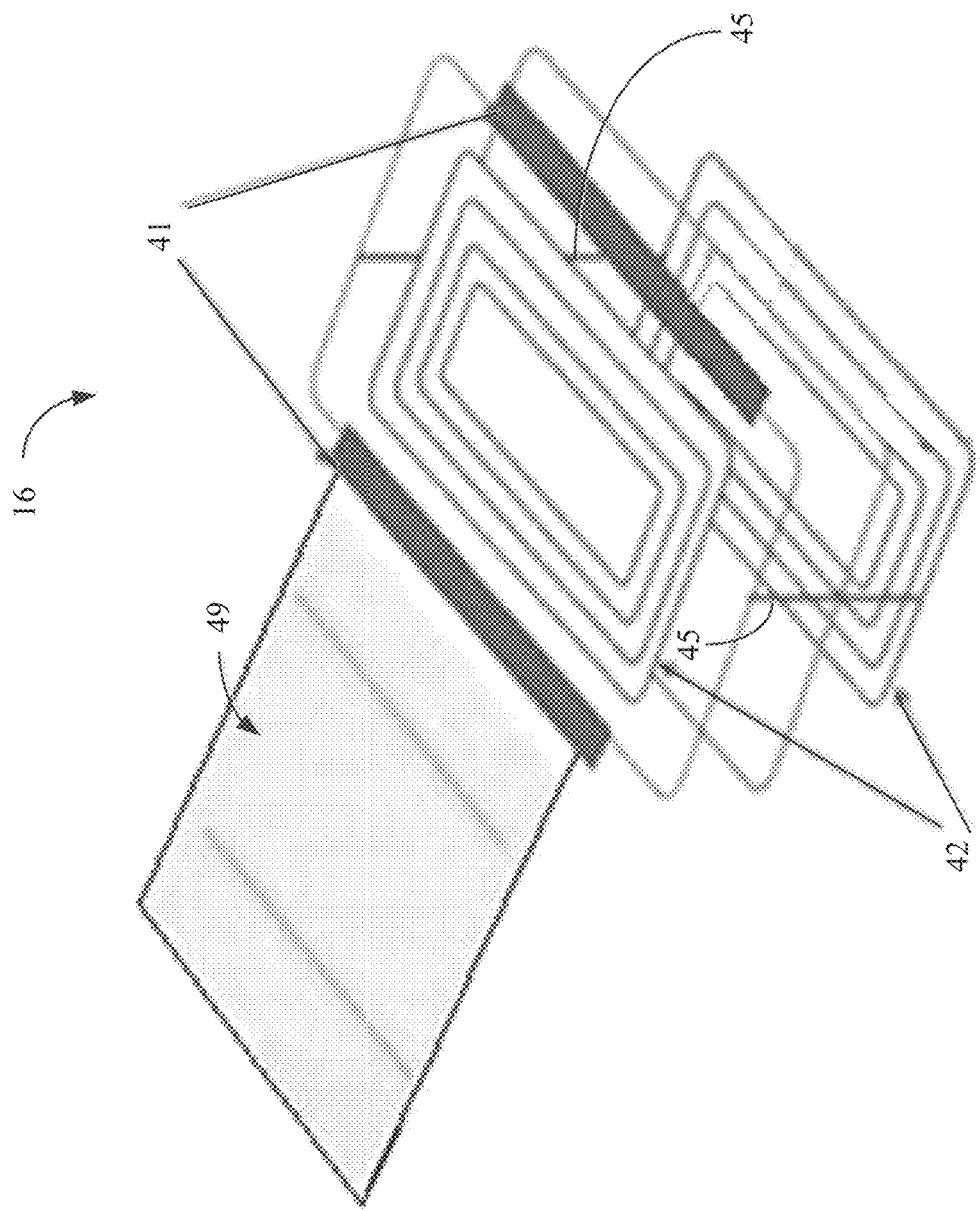
FIG. 8 is a perspective view of the pump assembly without the mounting structure.

Referring now to FIG. 8, pump assembly 16 is illustrated. Pump assembly 16 illustratively includes membrane assembly 49, magnet assembly 41, electromagnetic assembly 42, mounting structure 44 (not shown), linear guides 45 which may optionally include spring system 60. Linear guides 45 may permit magnet assembly 41 to move up and down linearly along linear guides 45. Spring system 60, discussed in greater detail below with reference to FIG. 11, may be configured to apply a spring force toward a neutral center position as magnet assembly 41 deviates from the natural position.

Figure 9A:
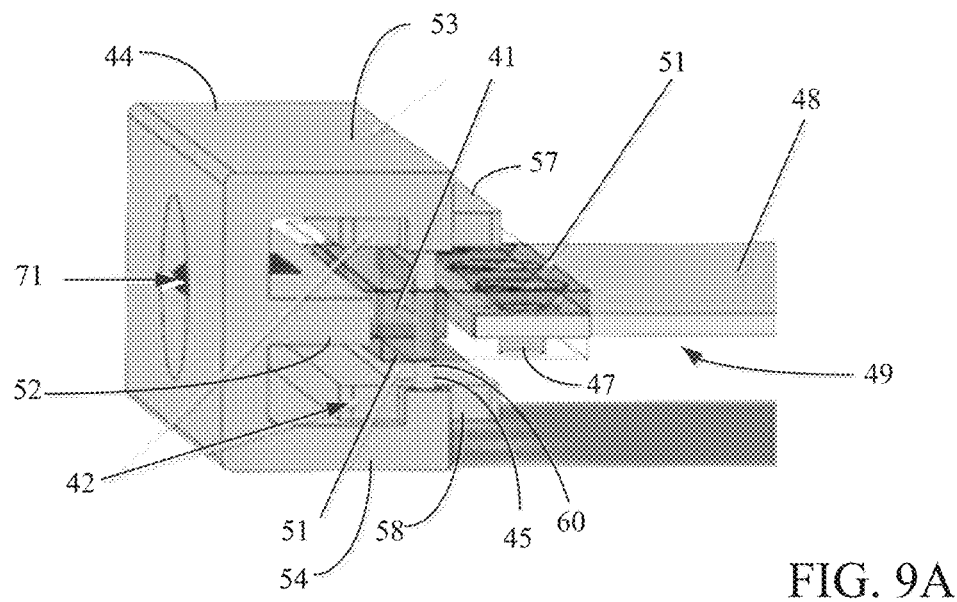
FIGS. 9A and 9B are perspective views of the pump assembly with the mounting structure.
Figure 9B:
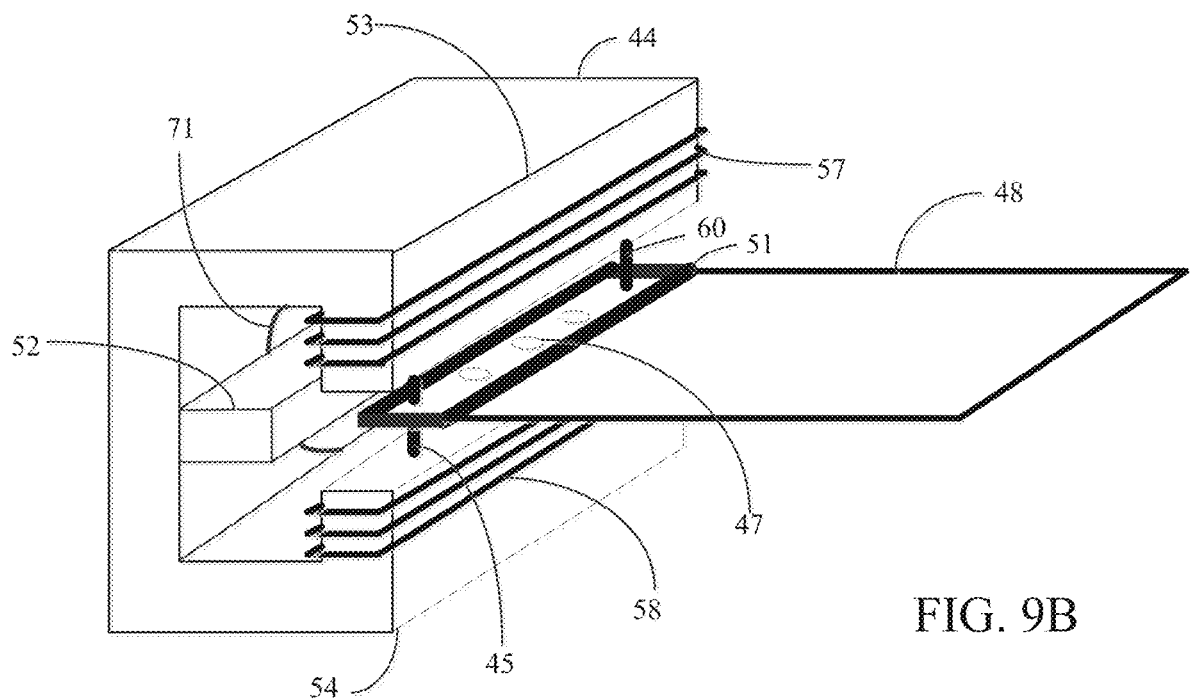

Referring now to FIGS. 9A and 9B, pump assembly 16 is illustrated showing mounting structure 44. Pump assembly 16 is sized and configured to fit within pump housing 12. Mounting structure 44, may be mounted to pump housing 12 using any well-known fixation technique. For example, mounting structure 44 may include threaded grooves that correspond to threaded grooves in pump housing 12 and may be coupled to pump housing 12 using plurality of screws. Alternatively, mounting structure 44 may be welded to pump housing 12.

Mounting structure 44 is sized and configured to be disposed within pump housing 12 adjacent to inlet 13. Mounting structure 44 may have a rectangular shape with a square cross-section. Mounting structure 44 may have inlet channel 71 which permits blood received at inlet 13 to flow through mounting structure 44. Mounting structure 44 may include inflow separator 52 which may permit blood that enters through inlet channel 71 to separate into upper flow channel 72 and lower flow channel 73.

Electromagnet assembly 42 and linear guides 45 may be coupled to or otherwise incorporated into mounting structure 44. Electromagnet assembly 42 may include first electromagnet 57 and second electromagnet 58 each having an electromagnetic winding that exhibits electromagnetic properties when an electrical current is applied. First electromagnet 57 may be coupled to upper flange portion 53 of mounting structure 44 as is illustrated in FIGS. 9A and 9B. Second electromagnet 58 may similarly be coupled to lower flange portion 54. In this configuration first electromagnet 57 may be positioned directly above second electromagnet 58 and a gap may exist between first electromagnet 57 and second electromagnet 58.

Linear guides 45 may be coupled at one end to upper flange portion 53 and another end to lower flanged portion 54 and may span the gap between first electromagnet 57 and second electromagnet 58. Linear guides 45 may be arranged parallel to one another and perpendicular to the direction of blood flow through inlet channel 71.

Magnet assembly 41 may include upper magnet 51 which is configured to move linearly along linear guides 45. Magnet 51 may be a permanent magnet and may either be a single magnet or may be may include multiple magnets coupled together to form magnet 51. Magnet 51 may be rectangular in shape and may have linear guide receiving portions that extend through magnet 51 through which linear guides 45 may be inserted and extend through. In this manner, magnet 51 may move up towards first electromagnet 57 and down towards second electromagnet 58.

Membrane assembly 49 may include membrane connector 47 and rectangular membrane 48. As discussed in greater detail below, rectangular membrane 48, may be generally rectangular in shape and may be connected to magnet 51 at by membrane connector 47. Magnet 51 may include a threaded receiving portion through which membrane connector 47 in the form of screws may be used to couple an end of rectangular membrane 48 to magnet 51.

Alternatively, membrane connector 47 may be a clamping device that clamps membrane 48 to magnet 51. It is understood that membrane connector 47 may be any well-known mechanism or techniques, e.g. epoxy, screws, etc.

Figure 11:
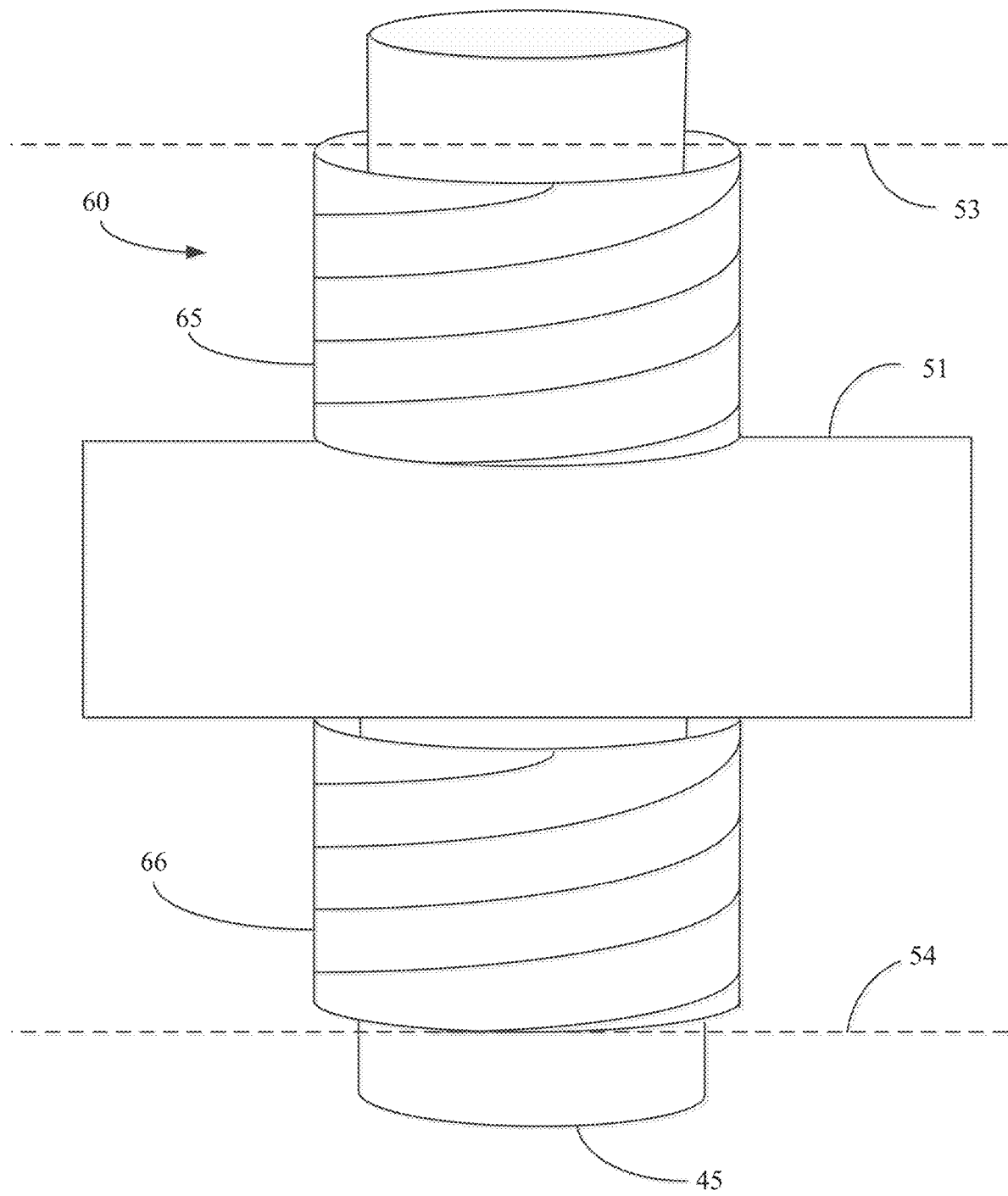
FIG. 11 is a perspective view of the spring system.

Membrane 48, coupled to magnet 51, as is illustrated in FIGS. 9A and 9B, may move up and down with magnet 51. Spring system 60 may optionally be coupled to linear guides 45 as illustrated in FIG. 11. Spring system may be designed to position magnet 51 in a neutral position. For example, the neutral position may be the same plane as inflow separator 52. As such, though magnet 51 may travel up and down along linear guides 45, magnet 51 may be designed to return to the neutral position.

First electromagnet 57 and second electromagnet 58 of electromagnetic assembly 42 may include one or more smaller metallic wires that may be wound into a coil, and may be in electrical communication with battery and/or controller via cable 9 connected via electrical port 15. First electromagnet 57 and second electromagnet 58 may be in electrical communication with one another and/or may be configured to operate independently and have separate wired connections to controller 3 and/or battery 4 via cable 9. Current flow applied to first electromagnet 57 and second electromagnet 58 could be reversed depending on the operating parameters applied. The wires of first electromagnet 57 and second electromagnet 58 may be insulated to prevent shorting to adjacent conductive material.

Implantable pump housing 12 may be comprised of titanium, stainless steel or any other rigid biocompatible material suitable for mounting pump assembly 16 to pump housing 12. Magnet assembly 41 may be comprised of one or more materials exhibiting magnetic properties such as iron, nickel, cobalt or various alloys. Where multiple magnets make up magnet assembly 41, the magnets may be linked by metallic parts made of a high saturation alloy, such as Vacoflux. Mounting structure too may be made from Vacoflux. The one or more smaller metallic wires wound into a coil in electromagnetic assembly 42 may be made of copper or any other metal having appropriate electromagnetic properties.

Figure 10A:
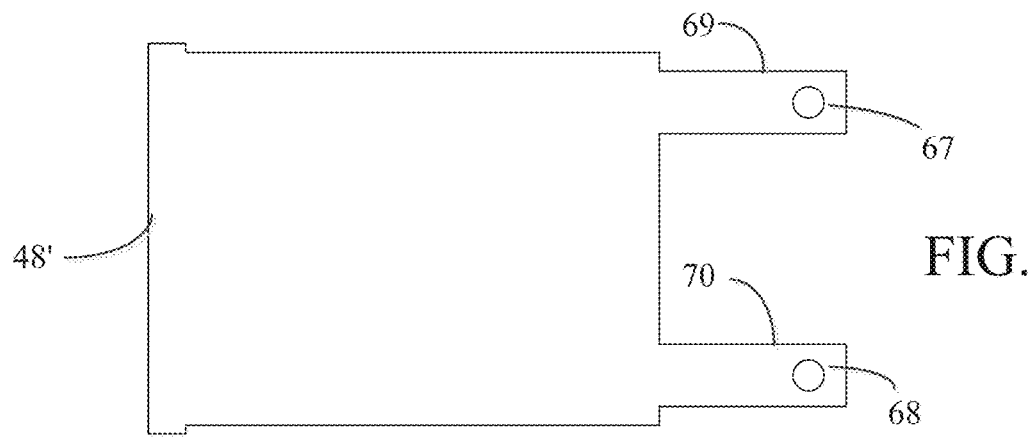
FIGS. 10A-10C are views of various rectangular membranes for use in the pump assembly.
Figure 10B:
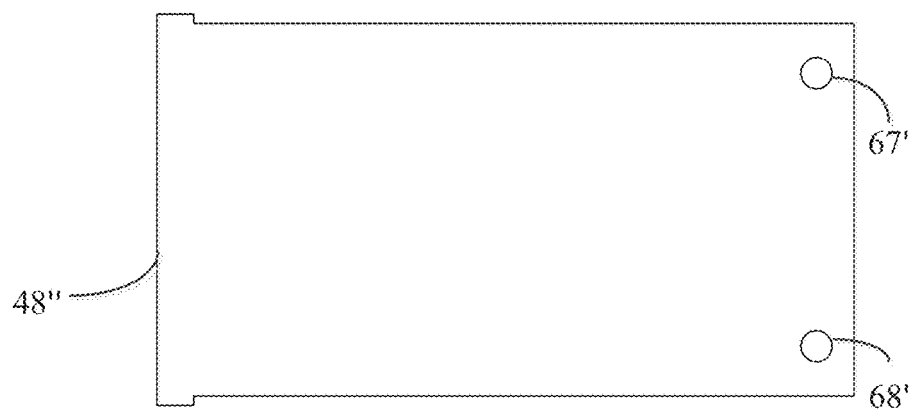
Figure 10C:
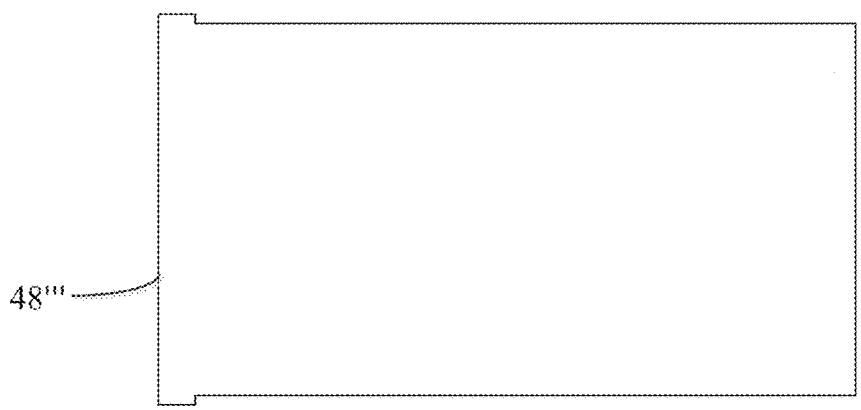

Referring now to FIGS. 10A-10C, various rectangular membranes are illustrated in greater detail. Rectangular membrane 48 may take a general thin rectangular shape. In a preferred embodiment, rectangular membrane 48 has a thin, planar shape and is made of an elastomer having elastic properties and good durability. For example, rectangular membrane 48 may be flexible through the entire length and cross-section of rectangular membrane 48 such that actuation of the implantable pump moves rectangular membrane to create wave-like deformation that pumps blood through the pump. Rectangular membrane 48 may have a uniform thickness from one end to the other. As yet a further alternative, rectangular membrane 48 may vary in thickness and exhibit more complex geometries, as described further herein. For example, rectangular membrane 48 may have a reduced thickness as the membrane extends from one end to the other and/or may have right-angled or beveled or rounded corners. Alternatively, or in addition to, rectangular membrane 48 may incorporate metallic elements such as a spring to enhance the spring force of the membrane in a direction normal to plane of the membrane. In yet another embodiment, rectangular membrane 48 may be pre-formed with an undulating shape.

Figure 12:
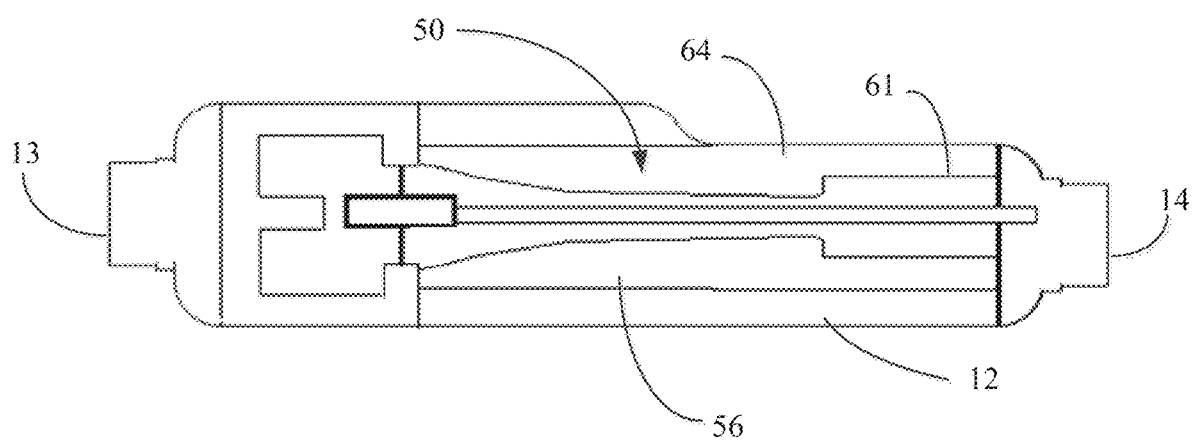
FIG. 12 is a cut-away cross sectional view of the pump assembly including funnel assembly.
Figure 13A:
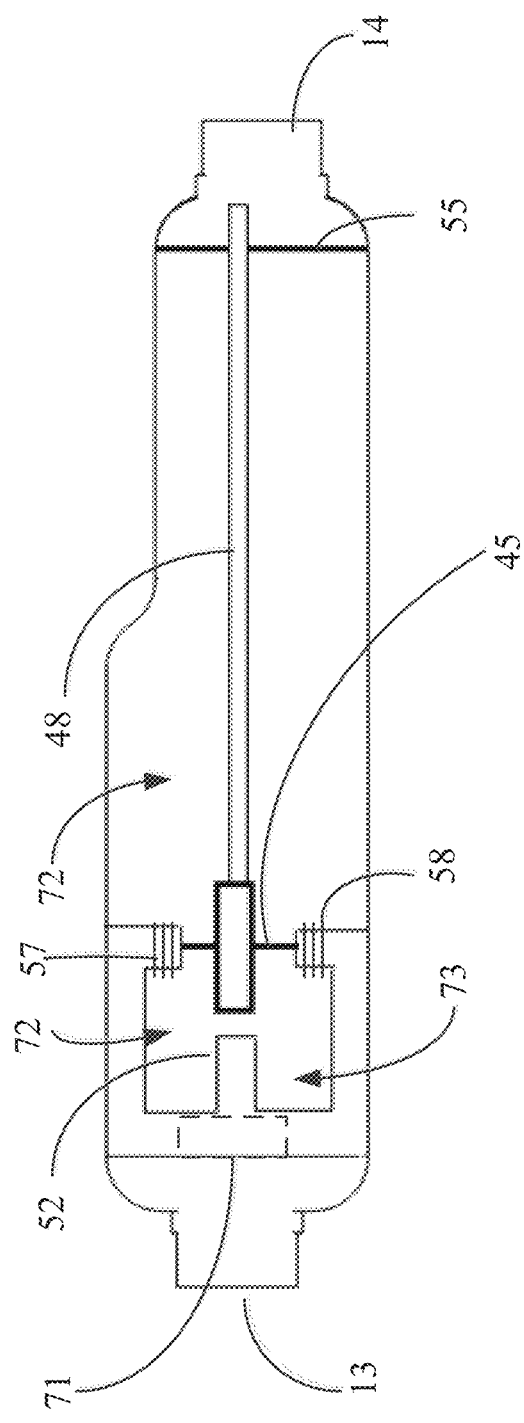
FIGS. 13A and 13B are cut-away cross sectional views of the pump assembly.
Figure 13B:
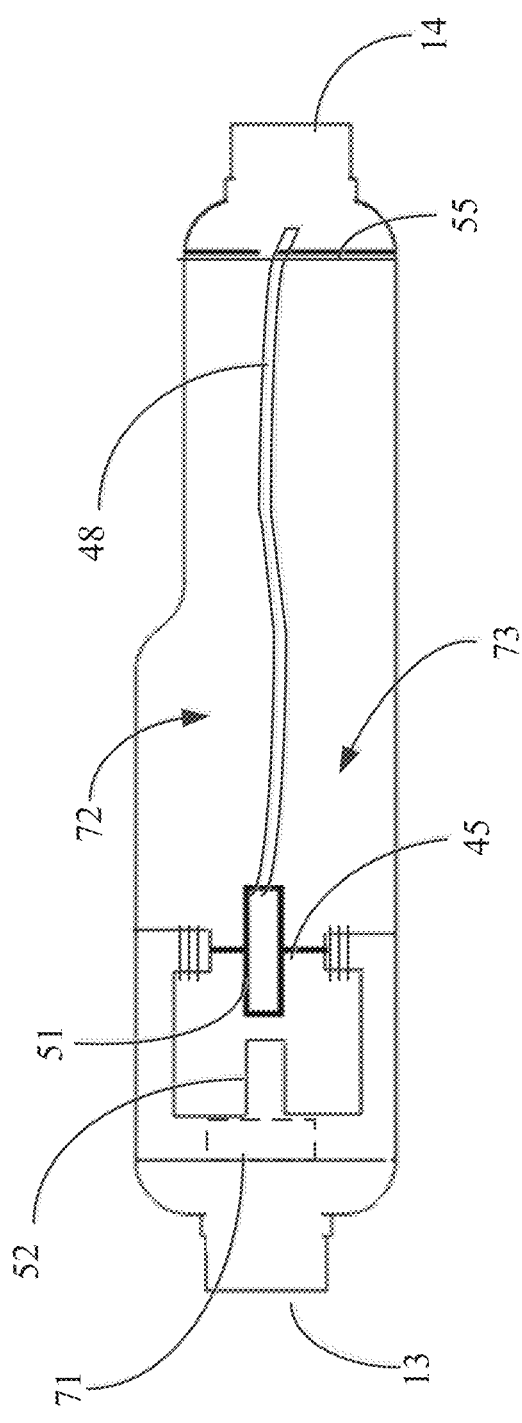

FIGS. 10A-10C illustrate various rectangular membranes that may be used in the implantable pumps described herein. As shown, each of the rectangular membranes have protrusions extending from the distal end of the rectangular membrane in a direction orthogonal to the blood flow path. As is illustrated in FIG. 10A, rectangular membrane 48' has two post receiving portions 67 and 68. Post receiving portions 67 and 68 may have a diameter slightly larger than that of posts 55 which may be parallel to linear guides 45 and extend from a top side of pump housing 12 to a bottom side as shown in FIGS. 13A-B. Alternatively, posts 55 may extend between upper funnel portion 64 and lower funnel portion 56 as is illustrated in FIG. 12. Also, as shown in FIG. 10A, rectangular membrane 48' has extended portions 69 and 70 that each protrude from the main body of rectangular membrane 48 in a direction parallel to the blood flow path to create a space between extended portions 69 and 70. Extended portions 69 and 70 have post receiving portions 67 and 68, respectively, therein and may permit fluid to more freely escape out of outlet 14 of implantable pump 2. Alternatively, in FIG. 10B, the main body of rectangular membrane 48" extends the entire length of the membrane without any extended portions. In FIG. 10B, the main body of rectangular membrane 48" has two post receiving portions 67' and 68'. In yet another alternative, as shown in FIG. 10C, rectangular membrane 48''' does not include the post receiving portions. This may permit the distal end of rectangular membrane 48''' nearest outlet 14 to move more freely.

Referring now to FIG. 11, one embodiment of spring system 60 is illustrated in greater detail. Spring system 60 may optionally be coupled or otherwise incorporated into linear guides 45. As mentioned above, spring system 60 may provide a spring force to magnet 51 when magnet 51 deviates from a neutral position. As illustrated in FIG. 11 the neutral position may be equidistant between upper flange portion 53 and lower flange portion 54. However, spring system 60 may be designed to set the neutral position at any position between upper flange portion 53 and lower flange portion 54. Spring system 60 may include upper spring portion 65 and lower spring portion 66. Upper spring portion 65 and lower spring portion 66 may collectively apply a spring force providing increased resistance as magnet 51 deviates from the neutral position.

Referring now to FIG. 12, funnel assembly 50 is illustrated. Funnel assembly 50 may optionally be disposed within pump housing 12 near outlet 14, as is illustrated in FIG. 12, to further narrow the blood flow through implantable pump 2 as blood travels from inlet 13 to outlet 14. Funnel assembly 50 may include upper funnel portion 64 and a lower funnel portion 56. As is illustrated in FIG. 12, the thickness of the funnel generally increases towards outlet 14. Additionally, the width of the flow channel may narrow as it moves inward toward outlet 14. Upper funnel portion 64 and lower funnel portion 56 may include threaded portions that extend the through upper funnel portion 64 and lower funnel portion 56 or at least partway through to permit the funnel portions to be secured to pump housing 12.

Referring now to FIGS. 13A and 13B, sectional views of implantable pump 2 are illustrated. In FIG. 13A, rectangular membrane 48 is seen suspended in tension between linear guides 45 and posts 55. In this configuration membrane 48 is suspended within pump housing 12. As explained above, blood may enter pump housing at inlet 13 and travel through mounting structure 44 via inlet channel 71. After traveling through inlet channel 71, blood must travel around inflow separator 52. Inflow separator 52 separates blood flow into upper flow channel 72 and lower flow channel 73. Upper flow channel 72 is defined by a top surface of magnet 51 and membrane 48, on one side, and an interior surface of pump housing 12 on the other side. Lower flow channel 73 is defined by a bottom surface of magnet 51 and membrane 48, on one side, and an interior surface of pump housing 12 on the other side. Upper flow channel 72 and lower flow channel 73 merge at outlet 14. In this manner, after exiting inlet channel 71, and traveling around inflow separator 52, blood travels along the top and bottom surface of membrane 48 until it reaches outlet 14.

Implantable pump may be activated to pump blood from inlet 13 to outlet 14 by moving magnet 51 up and down along linear guides 45. In this manner magnet 51 may move up towards first electromagnet 57 or down towards second electromagnet 58. To move magnet 51 up, current may be applied to first electromagnet 57 such that first electromagnet 57 generates a magnetic field that attracts magnet 51 and thus causes magnet 51 to move toward first electromagnet 57. At the same time, second electromagnet 58 may be induced with a current that causes second electromagnet 58 to generate a magnetic field having the opposite polarity of first electromagnet 57, thereby repelling magnet 51 from second electromagnet 58 while first electromagnet 57 attracts magnet 51. In this manner, first electromagnet 57 and second electromagnet 58 may work together to move magnet 51. Alternatively, second electromagnet 58 may not be energized while first electromagnet 57 is energized.

To move magnet 51 down, current may be applied to second electromagnet 58 such that second electromagnet 58 generates a magnetic field that attracts magnet 51 and thus causes magnet 51 to move toward second electromagnet 58. At the same time, first electromagnet 57 may be induced with a current that causes first electromagnet 57 to generate a magnetic field having the opposite polarity of second electromagnet 58, thereby repelling magnet 51 from first electromagnet 57 while second electromagnet 58 attracts magnet 51. Alternatively, first electromagnet 57 may not be energized while second electromagnet 58 is energized.

First electromagnet 57 and second electromagnet 58 may be designed to generate opposite polarities when current is applied in the same direction through first electromagnet 57 and second electromagnet 58. In this manner, the same electrical current may be applied simultaneously to first electromagnet 57 and second electromagnet 58 to achieve the desired effects. Alternatively, first electromagnet 57 and second electromagnet 58 may be designed to generate the same polarity when current is applied in the same direction. In this configuration the same current would not be applied simultaneously to first electromagnet 57 and second electromagnet 58.

As spring system 60 exhibits a spring force when magnet 51 deviates from the neutral position, when first electromagnet 57 and/or second electromagnet 58 cause magnet 51 to move up toward first electromagnet 57, spring system 60 may exert a downward spring force on magnet 51 toward the neutral position. Similarly, when first electromagnet 57 and/or second electromagnet 58 cause magnet 51 to move downward toward second electromagnet 58, spring system 60 may exert an upward spring force on magnet 51 toward the neutral position. The further magnet 51 deviates from the neutral position, the greater the spring force applied to magnet 51.

By manipulating the timing and intensity of the electrical signals applied to electromagnetic assembly 42, the frequency at which magnet 51 moves up and down may be altered. For example, by alternating the current induced in the electromagnetic assembly 42 more frequently, magnet 51 may be caused to cycle up and down more times in a given period. By increasing the voltage applied to electromagnetic assembly 42, magnet 51 may travel at a faster rate and caused to travel longer distances from the neutral position.

As magnet 51 is coupled to rectangular membrane 48 via membrane connector 47, movement of magnet 51 is applied to the end of rectangular membrane 48. FIG. 13B illustrates movement by magnet 51 being applied to rectangular membrane 48. As is shown in FIG. 13B, a current has been induced in first electromagnet 57 and/or second electromagnet 58 such that magnet 51 is attracted towards first electromagnet 57. The movement of magnet 51 has caused the end of membrane 48 coupled to magnet 51 to also move up and down thereby causing wave-like deformations in membrane 48. By inducing alternating current to first electromagnet 57 and second electromagnet 58, membrane 48 may be undulated between upper flow channel 72 and lower flow channel 73 to induce wavelike formations in rectangular membrane 48 that moves from the edge of rectangular membrane 48 coupled to magnet 51 towards outlet 14.

As rectangular membrane 48 is attached directly to magnet 51, when magnet 51 travels a certain distance upward or downward, the end of rectangular membrane 48 attached to magnet 51 also travels the same distance. For example, when magnet 51 travels 3 mm above the neutral position, the end of rectangular membrane 48 attached to magnet 51 also travels 3 mm in the same direction. Similarly, the frequency at which magnet 51 reciprocates up and down is the same frequency at which the end of rectangular membrane 48 that is coupled to magnet 51 travels the same distance. Preferably, the frequency is between 0 to 150 Hz, though other frequencies may be achieved using the system described herein.

Accordingly, when blood is delivered to inlet channel 71 and around inflow separator 52, it is propelled along both the top and bottom of rectangular membrane 48 and ultimately out of outlet 14. The waves formed in the undulating rectangular membrane may be manipulated by changing the speed at which magnet 51 moves up and down as well as the distance magnet 51 moves up and down. The transfer of energy from the membrane to the blood is directed along the length of membrane 48 towards outlet 14, and propels the blood along both sides of rectangular membrane 48.

In FIG. 13B magnet 51 is moving upward. As magnet 51 moves upwards, the entrance into lower flow channel 73 between a bottom surface of magnet 51 and mounting structure 44 begins to increase in size while the entrance to upper flow channel 72 between an upper surface of magnet 51 and mounting structure 44 begins to simultaneously decrease in size, causing blood to fill lower flow channel 73 nearest magnet 51. As magnet 51 is subsequently moved downward towards second electromagnet 58, lower flow channel 73 begins to narrow near magnet 51 and continues to narrow as a wave-like deformations in membrane 48 are propagated toward outlet 14. As the wave propagates across rectangular membrane 48, blood in the lower flow channel 73 is propelled towards outlet 14. Simultaneously, as magnet 51 moves down, the entrance to upper flow channel 72 begins to enlarge, allowing blood from inlet channel 71 to flow into this region. Subsequently, when magnet 51 is again thrust upwards, upper flow channel 72 begins to narrow near magnet 51, causing wave-like deformations to propagate across membrane 48, propelling blood towards outlet 14. Preferably, the speed of the wave propagation is 1 to 1.5 m/s, though other propagation speeds may be achieved using the system described herein.

By manipulating the waves formed in the undulating membrane by changing the frequency and amplitude at which magnet 51 moves up and down, the pressure gradient within upper flow channel 72 and lower flow channel 73 and ultimately the flow rate of the blood moving through implantable pump 2 may be adjusted. Appropriately controlling magnet 51 permits oxygen-rich blood to be effectively and safely pumped from the left atrium to the right subclavian artery and throughout the body as needed. While the pump described herein is described as pumping blood from the left atrium to the right subclavian artery, implantable pump 2 described herein could be used to pump blood from and to different areas, e.g. from the left ventricle to the aorta.

In addition to merely pumping blood from the left atrium to the subclavian artery, implantable pump 2 of the present invention may be operated to closely mimic physiologic pulsatility, without loss of pump efficiency. Pulsatility may be achieved nearly instantaneously by changing the frequency and amplitude at which magnet 51 moves, to create a desired flow output, or by ceasing movement of the magnet assembly 41 for a period time to create a period of low or no flow output. Unlike typical rotary pumps, which require a certain period of time to attain a set number of rotations per minute to achieve a desired fluid displacement and pulsatility, implantable pump 2 may achieve a desired flow output nearly instantaneously and similarly may cease output nearly instantaneously due to the very low inertia generated by the small moving mass of the moving components of the pump assembly. The ability to start and stop on-demand permits rapid changes in pressure and flow. Along with the frequency and amplitude, the duty cycle, defined by the percentage of time rectangular membrane 48 is excited over a set period of time, may be adjusted to achieve a desired flow output and pulsatility, without loss of pump efficiency. Even holding frequency and amplitude constant, flow rate may be altered by manipulating the duty cycle between 0 and 100%.

In accordance with another aspect of the invention, controller 3 may be programmed by programmer 5 to operate at selected frequencies, amplitudes and duty cycles to achieve a wide range of physiologic flow rates and with physiologic pulsatilities. For example, programmer 5 may direct controller 3 to operate implantable pump 2 at a given frequency, amplitude and/or duty cycle during a period of time when a patient is typically sleeping and may direct controller 3 to operate implantable pump 2 at a different frequency, amplitude and or duty cycle during time periods when the patient is typically awake. Controller 3 or implantable pump 2 also may include an accelerometer or position indicator to determine whether the patient is supine or ambulatory, the output of which may be used to move from one set of pump operating parameters to another. When the patient experiences certain discomfort or a physician determines that the parameters are not optimized, physician may alter one or more of at least frequency, amplitude and duty cycle to achieve the desired functionality. Alternatively, controller 3 or mobile device 6 may be configured to alter one or more of frequency, amplitude and duty cycle to suit the patient's needs.

Implantable pump 2 further may comprise one or more additional sensors for adjusting flow output and pulsatility according to the demand of the patient. Sensors may be incorporated into implantable pump 2 or alternatively or in addition to may be implanted elsewhere in or on the patient. The sensors preferably are in electrical communication with controller 3, and may monitor operational parameters that measure the performance of implantable pump 2 or physiological sensors that measure physiological parameters of the patients such as heart rate or blood pressure. By using one or more physiological sensors, pulsatile flow may be synchronized with a cardiac cycle of the patient by monitoring blood pressure or muscle contractions, for example, and synchronizing the duty cycle according to the sensed output.

Controller 3 may compare physiological sensor measurements to current implantable pump output. If it is determined by analyzing sensor measurements that demand exceeds current output, frequency, amplitude and/or duty cycle may be automatically adjusted to meet current demand. Similarly, the controller may determine that current output exceeds demand and thus alter output by changing frequency, amplitude and/or duty cycle. Alternatively, or in addition to, when it is determined that demand exceeds current output, an alarm may sound from controller 3. Similarly, operational measurements from operational sensors may be compared against predetermined thresholds and where measurements exceed predetermined thresholds or a malfunction is detected, an alarm may sound from controller 3.

Implantable pump 2 is sized and shaped to produce physiological flow rates, pressure gradients and pulsatility at an operating point at which maximum efficiency is achieved. Preferably, implantable pump 2 is sized and shaped to achieve flow rates ranging from 1 to 5 liters per minute at pressure gradients lower than a threshold value associated with hemolysis. However, implantable pump 2 described herein may be sized and configured to achieve various other flow rates at pressure gradients lower than a threshold value associated with hemolysis. Also, to mimic a typical physiological pulse of 60 beats per minute, implantable pump 2 may pulse about once per second. To achieve such pulsatility, a duty cycle of 50% may be utilized with an "on" period of 0.5 seconds and an "off" period of 0.5 seconds. For a given system, maximum efficiency at a specific operating frequency, amplitude and voltage may be achieved while producing a flow rate of 1 to 3 liters per minute at a duty cycle of 50% by manipulating one or more of the shape and size of blood flow channels and gaps, elastic properties of spring system, mass of the moving parts, membrane geometries, and elastic properties and friction properties of the membrane. In this manner, implantable pump 2 may be designed to produce desirable outputs to partially support physiological circulation while continuing to function at optimum operating parameters.

By adjusting the duty cycle, implantable pump 2 may be configured to generate a wide range of output flows at physiological pressure gradients. For example, pump system 1 may be configured to produce 1 to 3 liters per minute at a duty cycle of 50%, optimal operating frequency may be 120 Hz. For this system, flow output may be increased to 3 liters per minute or decreased to 1 liters per minute, for example, by changing only the duty cycle. As duty cycle and frequency operate independent of one another, duty cycle may be manipulated between 0 and 100% while leaving the frequency of 120 Hz unaffected.

The implantable pump system described herein may be tuned to achieve partial-support flow rates and physiological pressure gradients and pulsatility while avoiding hemolysis and platelet activation by applying low to moderate shear forces on the blood, similar to those exerted by a healthy heart. The moving components are rigidly affixed to one another and do not incorporate any parts that would induce friction, such as mechanical bearings or gears. Inlet channel 71 and upper flow channel 72 and lower flow channel 73 are sized and configured to also avoid friction by sizing the channels and gaps such that clearances of at least 0.5 mm are maintained between all moving components. Similarly, magnet 51 is sized and configured to be separated by at least 0.5 mm from non-moving components such as mounting structure 44 to avoid friction.

Figure 14:
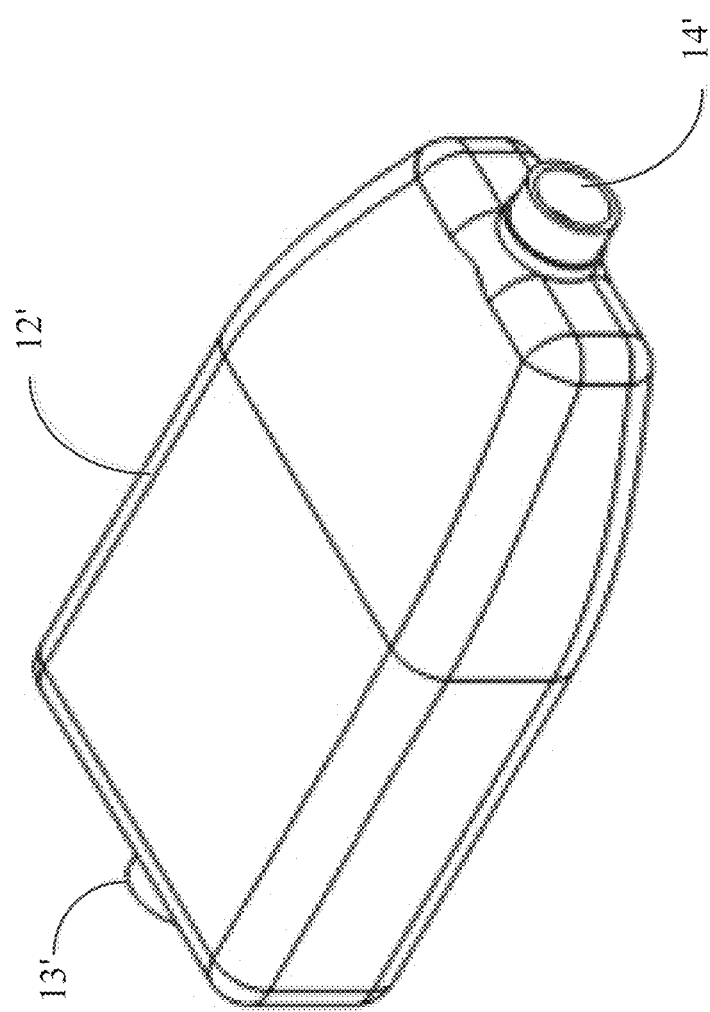
FIG. 14 is a perspective view of an alternative embodiment of the implantable housing.

Other embodiments of pump system 1 may include fewer or additional components or components having different shapes or sizes. For example, FIG. 14 illustrates an implantable housing 12' that narrows from inlet 13' toward outlet 14'. In this configuration, the rectangular membrane may be disposed therein and similarly narrow as it nears outlet 14'. In this embodiment, the narrowing of implantable housing 12' may help direct the blood flow out of outlet 14'.

Figure 15:
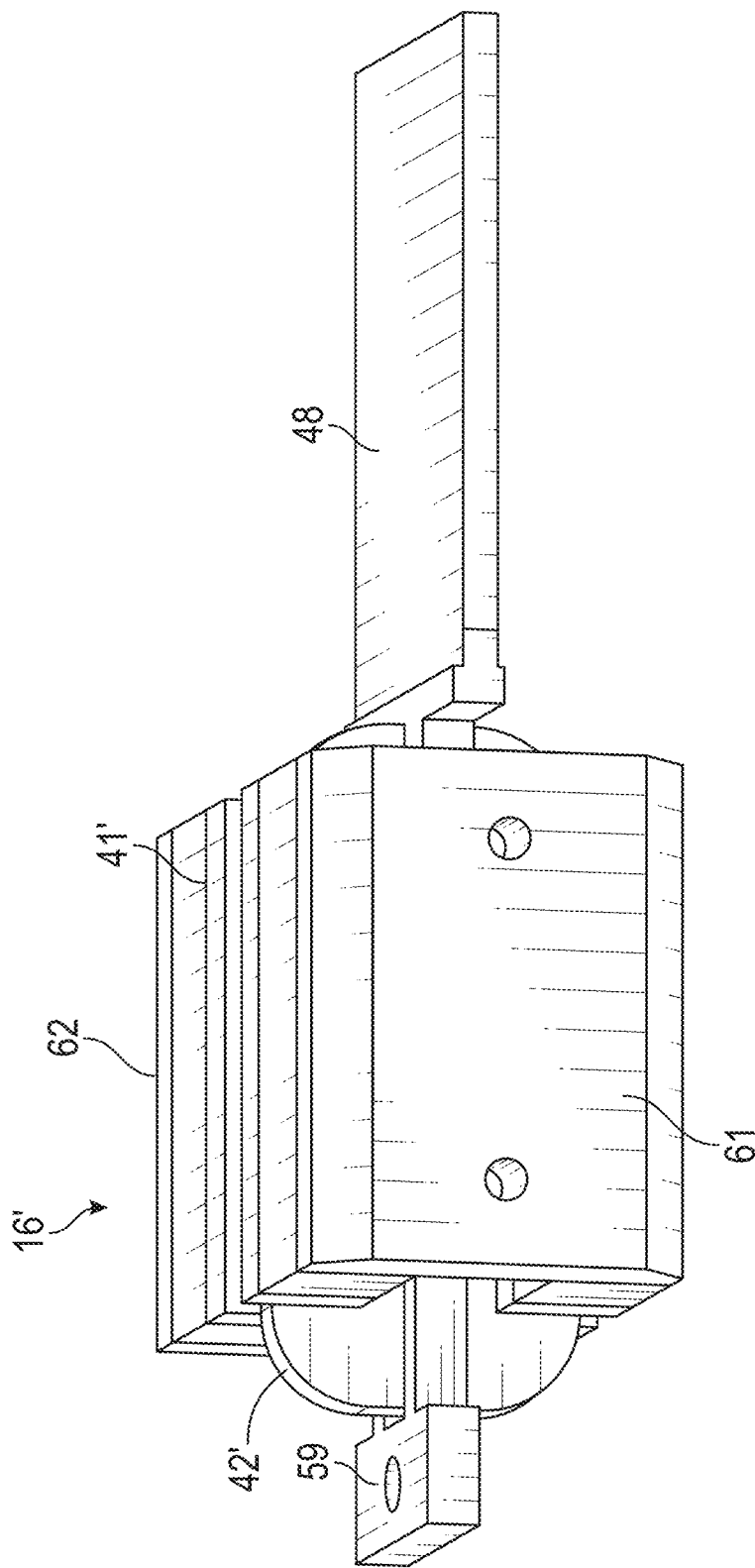
FIG. 15 is a perspective view of an alternative electromagnetic actuator having a moving electromagnetic assembly.

Other embodiments may employ an electromagnetic actuator having magnets and electromagnetic portions different than those described in FIGS. 4-13. For example, FIG. 15 illustrates an alternative embodiment of the pump assembly. Pump assembly 16', shown in FIG. 15, includes electromagnetic assembly 42', magnet assembly 41', first support structure 61, second support structure 62, membrane holder 59 and rectangular membrane 48. Membrane holder 59 is configured to be disposed within and mounted to implantable housing 12 using screws, welding or any other well-known technique appropriate for rigidly coupling membrane holder 59 to implantable housing 12. Membrane holder 59 is configured to support electromagnetic assembly 42' and rectangular membrane 48.

First support structure 61 and second support structure 62 are also configured to be disposed within and mounted to implantable housing using any well-known technique such as screws or welding. First support structure 61 and second support structure 62 each may support a portion of magnet assembly 41' having one or more positive permanent magnets and negative permanent magnets. Magnet assembly 41' may be mounted to first support structure 61 and second support structure 62 such that a magnetic field is generated at a top end of first support structure 61 and second support structure 62 and a magnetic field having an opposite polarity is generated near a bottom end of first support structure 61 and second support structure 62. First support structure 61 and second support structure 62 may be mounted to implantable housing 12 such that a gap exists between the two that is sufficiently large enough for electromagnetic assembly 42' to fit between and move in a plane parallel to the gap.

Membrane holder 59 may be flexible and may permit electromagnetic assembly 42' to move up toward the first magnetic field and down toward the second magnetic field. As electromagnetic assembly 42' moves up and down, an end of membrane 48 coupled to electromagnetic assembly 42' is also caused to move up and down. Also, as electromagnetic assembly 42' moves up and down, membrane holder 59 is elastically deformed and applies a spring force is to electromagnetic assembly 42' to return electromagnetic assembly 42' to the neutral position where membrane holder 59 is not deformed.

As the end of rectangular membrane 48 moves up and down, wavelike deformations are propagated along membrane 48 toward outlet 14, as described above. In this embodiment, current applied to electromagnetic assembly 42' causes electromagnetic assembly 42' to move up and down while magnet assembly 41' stays stationary. Unlike the embodiment where magnet 51 moves, in the embodiment illustrated in FIG. 15, electromagnetic assembly 42' may be attracted to and thus move toward one magnetic field by inducing current in one direction, and conversely, may be attracted to and thus move in the other direction towards the other magnetic field, having an opposite polarity, by inducing current in the opposite direction.

Figure 16:
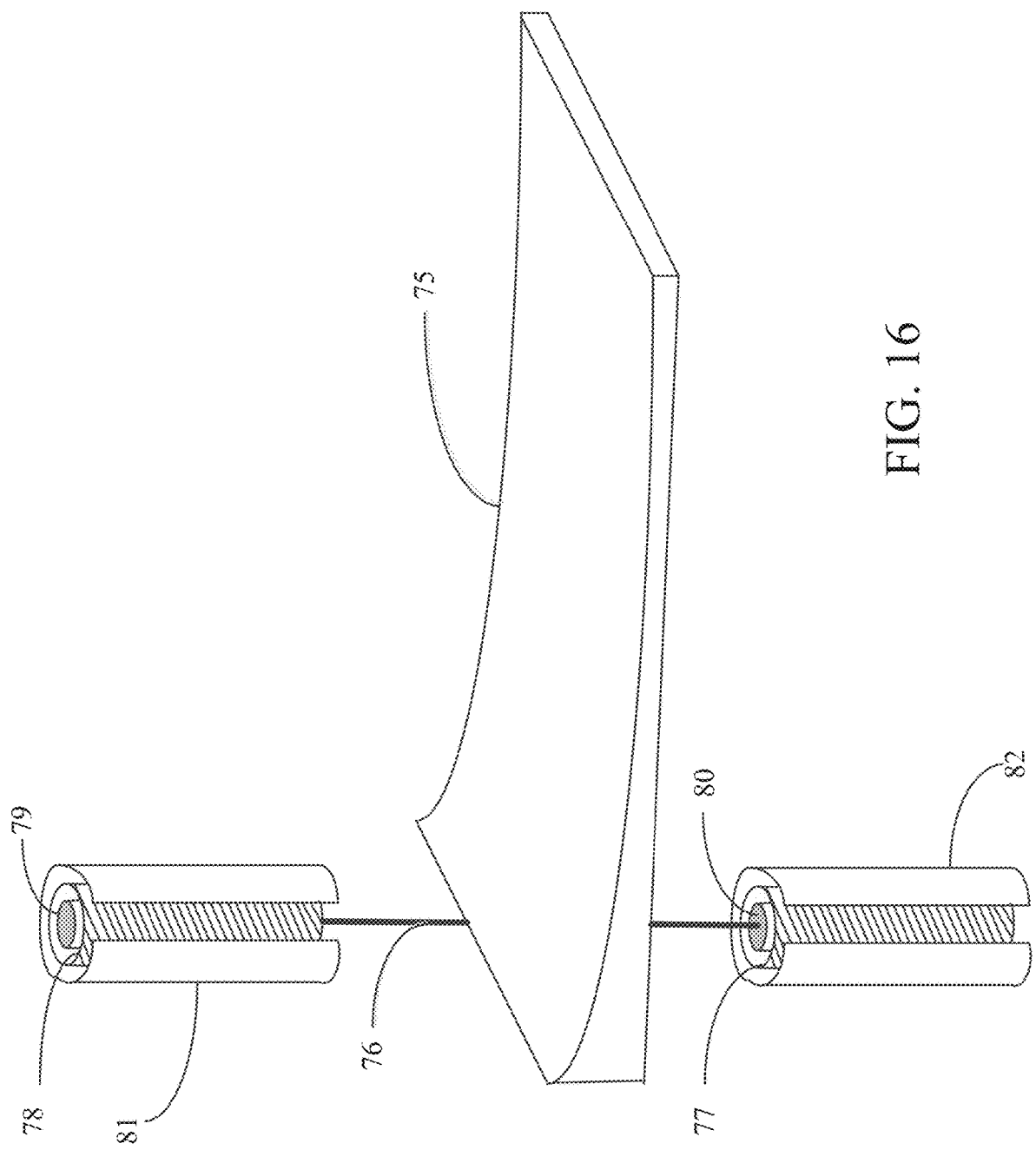
FIG. 16 is a perspective view of an alternative electromagnetic actuator having a dual coil electromagnetic actuator.

Another embodiment of the electromagnetic actuator is illustrated in FIG. 16. In FIG. 16, an alternative system for propagating waves in the membrane is described. As is shown in FIG. 16, this alternative system may include rectangular membrane 75, first magnet 79, first coil 78, and first ferromagnetic casing 81 as well as second magnet 80, second coil 77, and second ferromagnetic casing 82. First magnet 79 and second magnet 80 are connected by rod 76 which is also coupled to membrane 75. First coil 78 and second coil 77 may be connected to controller 3 and/or battery 4. Controller may induce, and alternate, current in first coil 78 and second coil 77 which causes first magnet 79 and second magnet 80 to move up and down in tandem. As first magnet 79 and second magnet 80 move up and down, rod 76 may be moved up and down causing the portion of membrane 75 connected to rod 76 to move up and down. In this manner, membrane 75 may be caused to undulate. Membrane 75 may vary in thickness as it moves from one end to another. The alternative electromagnetic actuator shown in FIG. 16 may be designed and configured to fit within pump housing 12 and function as a blood pump in the manner described herein.

Figure 17:
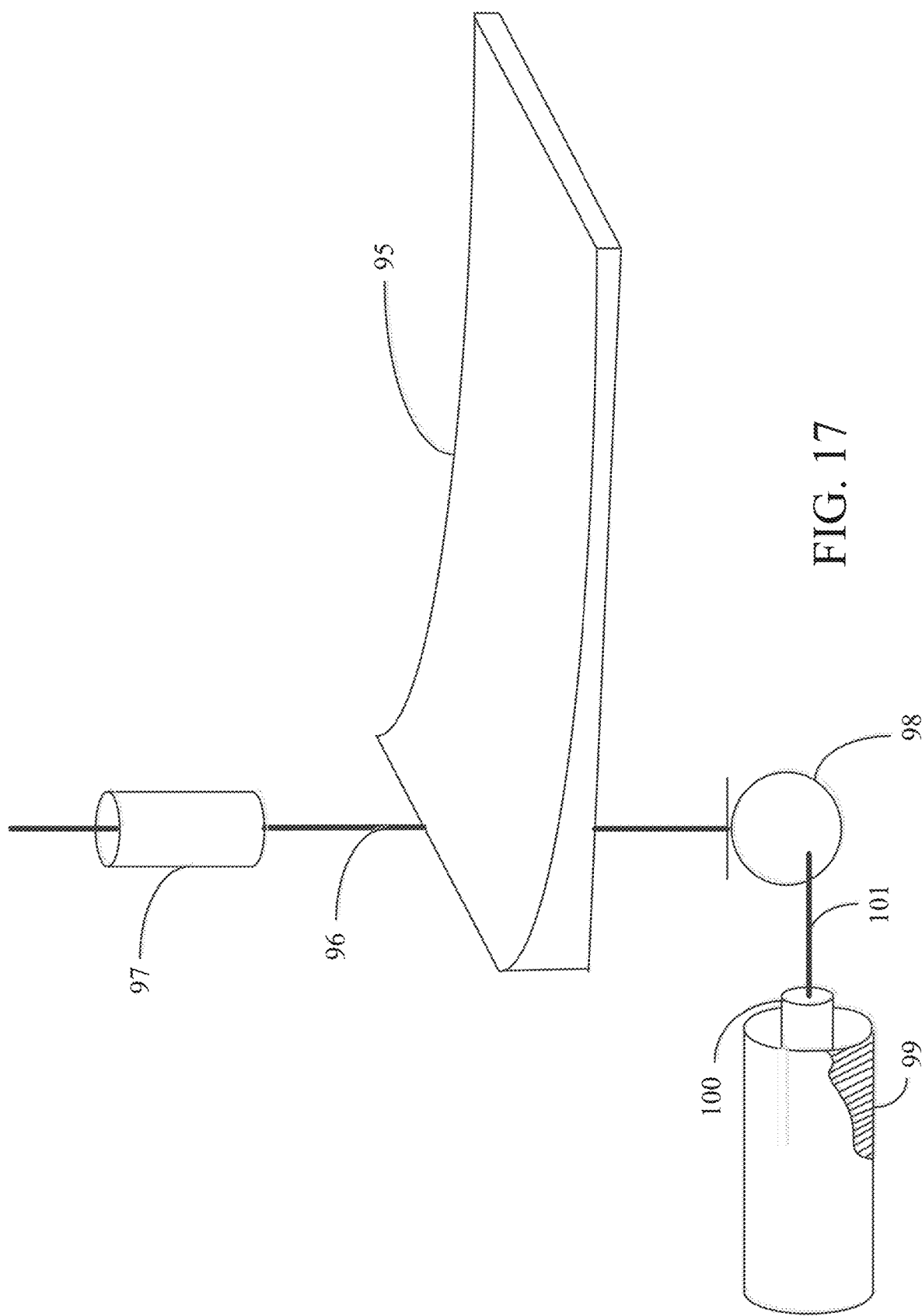
FIG. 17 is a perspective view of an alternative mechanical actuator having a mechanical actuator with a cam.

Referring now to FIG. 17, an electromechanical actuator embodiment is illustrated. The system shown in FIG. 17 includes rectangular membrane 95, rod 96, guide 97, cam 98, an assembly of coil 99, rotating magnet 100, the combination of 99 and 100 forming an asynchronous motor, and connector 101. Coil 99 may be in electrical communication with controller 3 and/or battery 4 and may be energized to move in rotation magnet 100 on the same axis as coil 99. Rotating magnet 100 may be connected to connector 101 which is connected to cam 98 at the other end. Membrane 95 is connected at one end to rod 96. Rod 96 is connected to cam 98 at one end and is guided by guide 97 so that rod 96 is only free to move along its longitudinal axis. As rotating magnet 100 is caused by the magnetic field generated by coil assembly 99, the movement of rotation of magnet 100 is transmitted by cam 98 via connector 101 to rod 96 which moves up and down its longitudinal axis. As rod 96 moves up and down its longitudinal axis, the end of membrane 95 that is connected to rod 96 moves up and down causing wave-like deformations to propagate along membrane 95. The alternative electromechanical actuator shown in FIG. 17 may be designed and configured to fit within pump housing 12 and function as a blood pump in the manner described herein.

Referring now to FIG. 18A-18C, implantable pump 102, which may be used in system 1 in place of implantable pump 2, is illustrated in greater detail. Implantable pump 102 includes pump housing 112 which is made of a biocompatible material, such as titanium, and is sized to be implanted within a patient's chest as described above. Pump housing 112 may be two or more pieces that fit together by, for example, threads or welding, to form fluid tight pump housing 112. In one embodiment, pump housing 112 is sized and configured to have a length between 60-80 mm, a width between 30-60 mm and a height between 7-15 mm. However, pump housing 112 may have any other size suitable for pump assembly 116 to be disposed within pump housing 112. Pump housing includes inlet 113 and outlet 114 through which blood may flow in and out, respectively. Pump also may include electrical port 115 to attach implantable pump 102 to cable 109. Electrical port 115 may permit cable 109 to transverse pump housing 112 and connect to pump assembly 116 in a fluid tight manner. Cable 109 may deliver electrical wires from controller 3 and battery 4 to pump assembly 116.

Figures 19A, 19B:
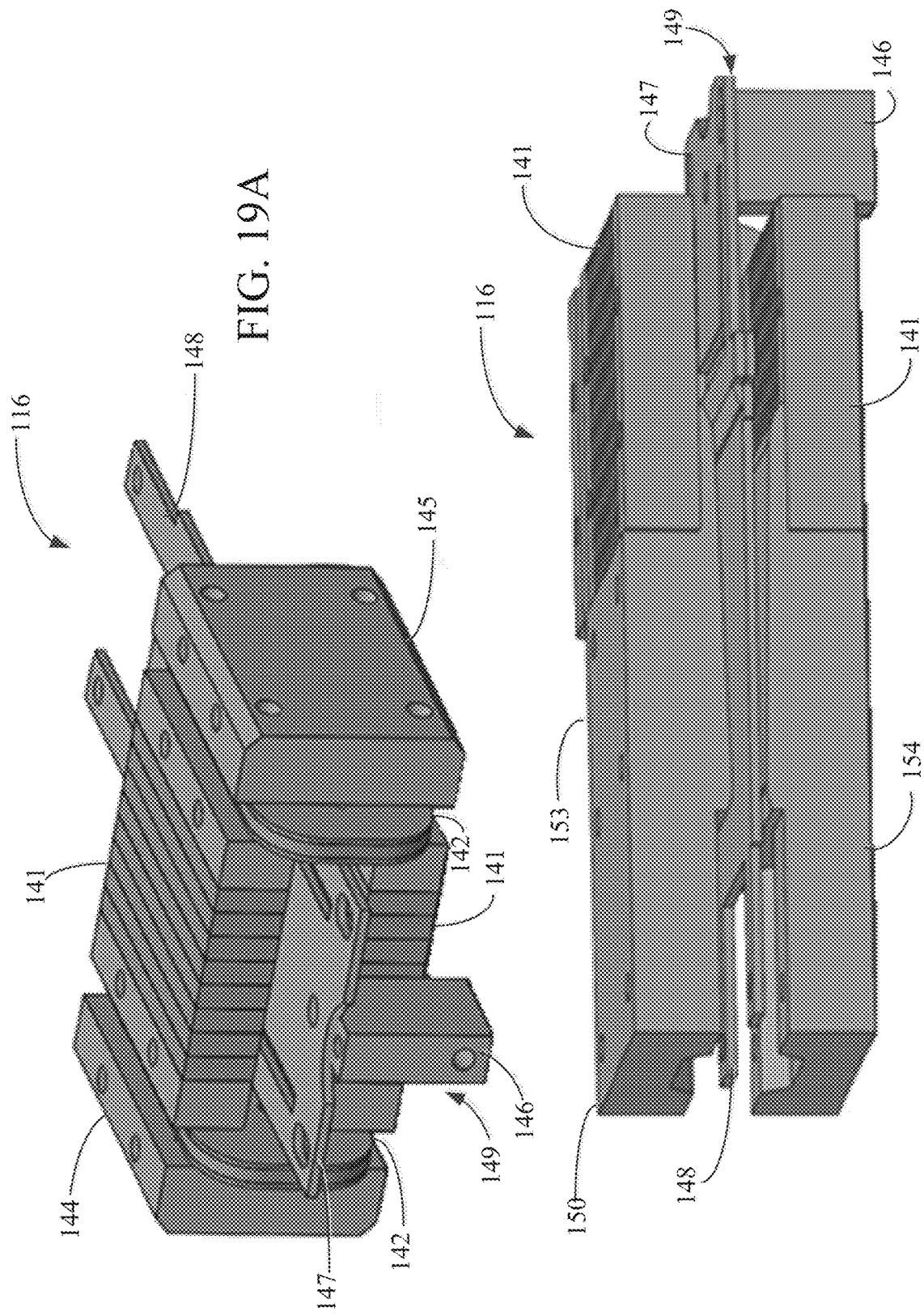
FIGS. 19A and 19B are perspective views of the pump assembly.

Referring to FIGS. 19A and 19B, pump assembly 116 is illustrated in greater detail. Pump assembly 116 may include membrane assembly 149, magnet assembly 141, electromagnetic assembly 142, fixation elements 144 and 145, and funnel assembly 150. Membrane assembly 149 may include mounting structure 146, membrane holder 147 and rectangular membrane 148. Electromagnetic assembly 142 may include first coil 157 and second coil 158 each having an electromagnetic winding. Magnet assembly 141 may include upper magnet unit 151 and a lower magnet unit 152.

Pump assembly 116 is sized and configured to fit within pump housing 112. Fixation elements 144 and 145, mounting structure 146 and funnel assembly 150 may be mounted to pump housing 112 using any well-known fixation technique. For example, fixation elements 144 and 145, mounting structure 146, funnel assembly 150 may include threaded grooves that correspond to threaded grooves in pump housing 112 and may be coupled to pump-housing 112 using plurality of screws. Alternatively, fixation elements 144 and 145, mounting structure 146, funnel assembly 150 may be welded to pump housing 112.

Figure 20:
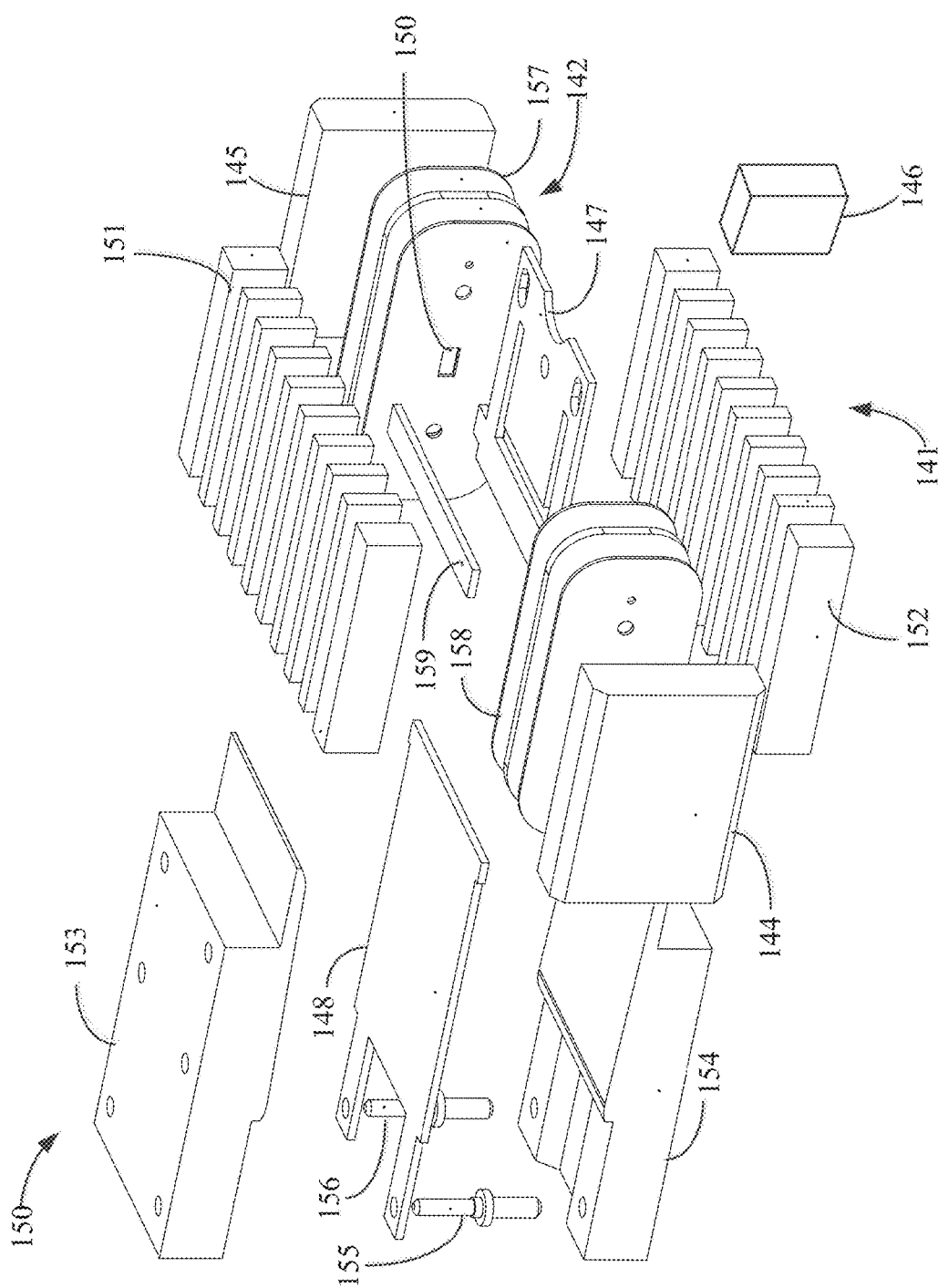
FIG. 20 is an exploded view of the pump assembly.

Referring now to FIG. 20, an exploded view of pump assembly 116 is illustrated. As is shown in FIG. 20, upper magnet unit 151 and lower magnet unit 152 may include a number of smaller magnets, or alternatively may include only a single magnet. As is also shown in FIG. 20, both upper magnet unit 151 and lower magnet unit 152 may be rectangular in shape and may be sized and configured to be supported by funnel assembly 150. Upper magnet unit 151 and lower magnet unit 152 also may be secured to pump housing 112 and may include a securing portion designed to secure upper magnet unit 151 and lower magnet unit 152 to pump housing 112.

Funnel assembly 150 may include upper funnel 153 and lower funnel 154, as is illustrated in FIG. 20. Upper funnel 153 and lower funnel 154 may include a flanged portion for supporting upper magnet unit 151 and lower magnet unit 152, respectively. Upper funnel 153 may have an upper surface secured to pump housing 112 and lower funnel 154 may have a lower surface secured to pump housing 112. When lower funnel 154 and upper funnel 153 are secured to the pump housing, a gap exists between lower funnel 154 and upper funnel 153, as is illustrated in FIG. 19A.

Between lower funnel 154 and upper funnel 153 rectangular membrane 148 is suspended and may extend the length of upper funnel 153 and lower funnel 154. Posts 155 and 156 extend between upper funnel 153 and lower funnel 154 near a distal end of upper funnel 153 and lower funnel 154 adjacent to outlet 114 of pump housing 112. Posts 155 and 156 are positioned in a parallel fashion and are separated a sufficient distance to permit fluid flow between them. Rectangular membrane 148 is connected to posts 155 and 156 at a distal end of rectangular membrane 148. Rectangular membrane 148 may have two holes in the distal end of rectangular membrane 148 that are sized and configured to receive posts 155 and 156. Posts 155 and 156 may further include connection elements that move freely along posts 155 and 156 and serve to anchor rectangular membrane 148 to posts 155 and 156.

As is shown in FIG. 20 as well as FIGS. 19A and 19B, membrane holder 147 is positioned at the distal end of rectangular membrane 148. As is illustrated in FIG. 20, membrane holder 147 is also positioned between upper magnet unit 151 and lower magnet unit 152. Additionally, membrane holder 147 is positioned between first coil 157 and second coil 158. Membrane holder 147 may be designed to couple to membrane clamp 159. To secure rectangular membrane 148 to membrane holder 147, a proximal end of rectangular membrane 148 may be placed over an end of membrane holder 147 designed to received rectangular membrane 148. Subsequently, membrane clamp 159 may be placed over the portion of rectangular membrane 148 that is covering membrane holder 147 and clamped or otherwise secured to membrane holder 147. Membrane clamp 159 may be designed to snap into membrane holder 147 or otherwise screw into membrane holder 147. In this manner, rectangular membrane 148 may be secured to membrane holder 147. Alternatively, rectangular membrane 148 may secured to membrane holder 147 without the use of membrane clamp 159 using a number of well-known securing techniques, e.g. epoxy, screws, etc. At a proximal end of membrane holder 147, membrane holder 147 is secured to mounting structure 146. As explained above, mounting structure 146 is secured to pump housing 112.

First coil 157 and second coil 158 of electromagnetic assembly 142 may include one or more smaller metallic wires that may be wound into a coil, and may be in electrical communication with battery and/or controller via cable 9 connected via electrical port 115. First coil 157 and second coil 158 may be in electrical communication with one another and/or may be configured to operate independently and have separate wired connections to controller 3 and/or battery 4 via cable 9. Current flow applied to first coil 157 and second coil 158 could be reversed depending on the operating parameters applied. The wires of first coil 157 and second coil 158 may be insulated to prevent shorting to adjacent conductive material.

First coil 157 and second coil 158 may include membrane holder receiving portions 150 for securing a portion of the distal end of membrane holder 147 to first coil 157 on one side and second coil 158 on the other side. In this manner, first coil 157 and second coil 158 are supported only by membrane holder 147 which is mounted on mounting structure 146. The connection between first coil 157 and second coil 158 and membrane holder 147 may further include a spring system to reduce resonance effects. First coil 157 and second coil 158 are positioned relative to membrane holder 147 such that upper magnet unit 151 and lower magnet unit 152 are positioned between first coil 157 and second coil 158 but do touch coil 157 and second coil 158. First coil 157 and second coil 158 may be sized such that upper funnel 153 and lower funnel 154 are positioned between first coil 157 and second coil 158 without touching first coil 157 and second coil 158.

Fixation elements 144 and 145 may be secured to pump housing 112 such that first coil 157 and second coil 158 are positioned between fixation elements 144 and 145 without touching fixation elements 144 and 145. Fixation elements 144 and 145 may have magnetic properties and thus may loop the magnet field created by magnet assembly 141 and otherwise contribute to the magnetic force generated. In this manner, first coil 157 is positioned between fixation element 145 on one side and on the other side magnet assembly 141, membrane holder 147, rectangular membrane 148 and funnel assembly 150. Similarly, second coil 158 is positioned between fixation element 144 on one side and on the other side magnet assembly 141, membrane holder 147, rectangular membrane 148 and funnel assembly 150 on the other side. Also, in this configuration, rectangular membrane 148 is suspended within funnel assembly 150, membrane holder 147 is suspended within magnet assembly 141 rectangular membrane 148 and membrane holder 147 are surrounded on either side by first coil 157 and second coil 158.

Implantable pump housing 112, fixation elements 144 and 145, mounting structure 146, and funnel assembly 150 may be comprised of titanium, stainless steel or any other rigid biocompatible material suitable for mounting pump assembly 116 to pump housing 112. These components may be insulated and/or made of non-conductive material to reduce unwanted transmission of the electrical signal. Magnet assembly 141 may be comprised of one or more materials exhibiting magnetic properties such as iron, nickel, cobalt or various alloys. Where multiple magnets make up magnet assembly 141, the magnets may be linked by metallic parts made of a high saturation alloy, such as Vacoflux. Mounting structure too may be made from Vacoflux. The one or more smaller metallic wires wound into a coil in electromagnetic assembly 142 may be made of copper or any other metal having appropriate electromagnetic properties.

Figure 21A:
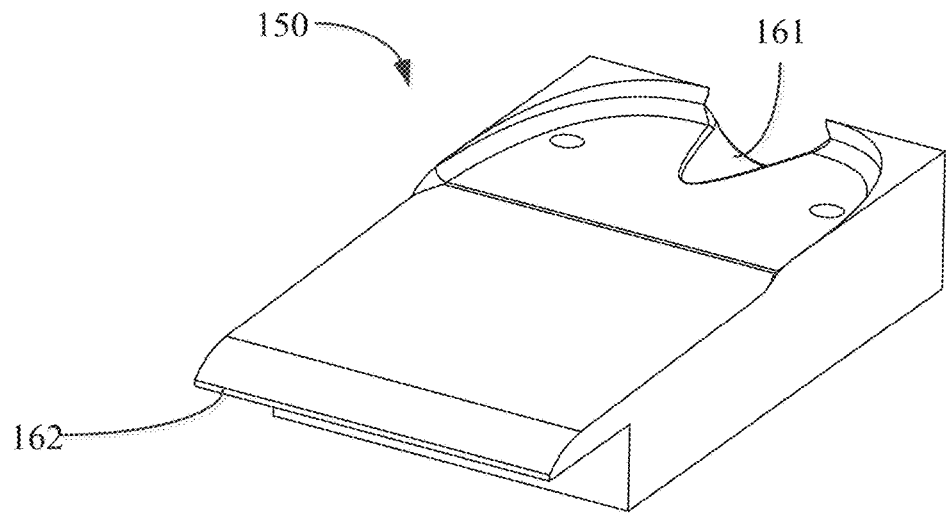
FIGS. 21A and 21B, are, respectively, a perspective view and a plan view of the funnel portion of the pump assembly.
Figure 21B:
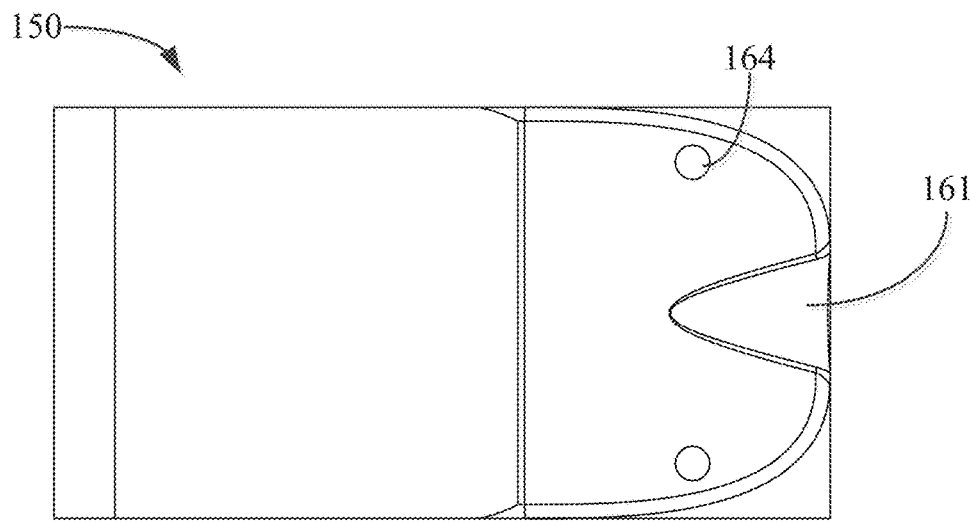

Referring now to FIGS. 21A and 21B, a portion of funnel assembly 150 is illustrated. The funnel portion illustrated may be either upper funnel 153 and lower funnel 154 as these units may be interchangeable. As is illustrated in FIGS. 21A and 21B, the thickness of the funnel portion increases as it moves towards narrows funnel outlet 161. As is also illustrated in FIGS. 21A and 21B, the width of the flow channel creased by the flow channel narrows as it moves towards funnel outlet 161. The funnel may include flanged portion 162 designed to support at least a portion of magnetic assembly 141 and secure at least a portion of magnetic assembly 141 to pump housing 112. Upper funnel 153 and lower funnel 154 also may include threaded portions 164 that extend the through upper funnel 153 and lower funnel 154 or at least partway through and permit upper funnel 153 and lower funnel 154 to be secured to pump housing 112.

Referring now to FIGS. 22A and 22B, membrane holder 147 is illustrated. As is shown in these figures, membrane holder 147 may be generally rectangular having mounting portion 165 and membrane securing portion 166. Mounting portion 165 is designed to be secured to mounting structure 146. As is shown in FIG. 22B, at least membrane securing portion 166 is designed to be flexible. As such, membrane securing portion 166 may flex up and down relative to mounting portion 165. Membrane holder 147, including at least membrane securing portion 166, may have elastic properties which exhibits a spring force when membrane securing portion 166 is deflected relative to mounting portion 165. While, membrane securing portion 166 may flex when deformed up and down relative mounting portion 165, membrane securing portion 166 may rigidly resist movement along any other axis, e.g., tilt or twist movements. Membrane holder 147 may be made from any metal or material having the properties just described.

In one embodiment, membrane holder 147 and/or membrane clamp 159 may exhibit electromagnetic properties. For example, membrane holder 147 and/or membrane clamp 159 may be in electrical communication with electromagnetic assembly 142. As such when electromagnetic assembly 142 is electrically activated, membrane holder 147 and/or membrane clamp 159 may too become electrically activated and thus generate a magnetic field due to their electromagnetic properties. In generating an electromagnetic field, membrane holder 147 and/or membrane clamp 159 may become attracted to either upper magnet unit 151 or lower magnet unit 152.

Figure 23A:
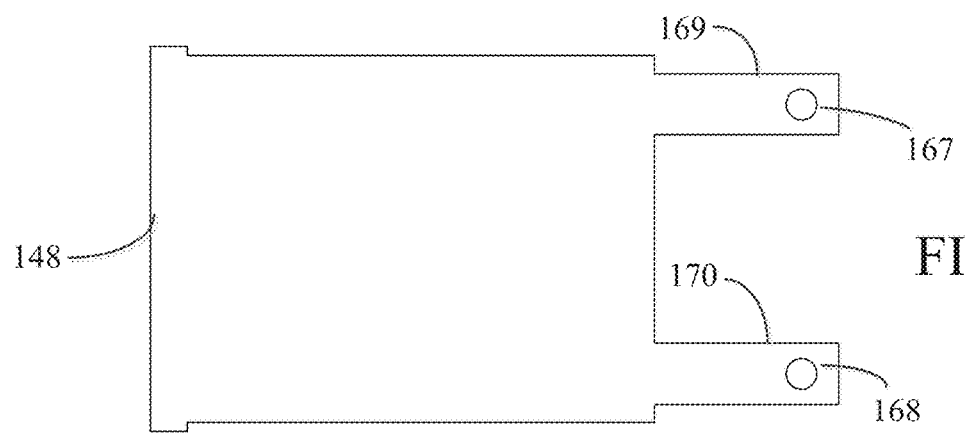
FIGS. 23A-C are views of various rectangular membranes for use in the pump assembly.
Figure 23B:
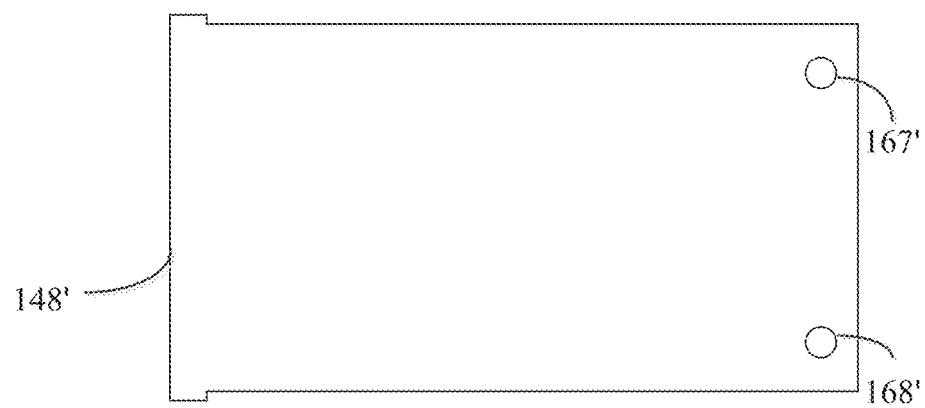
Figure 23C:
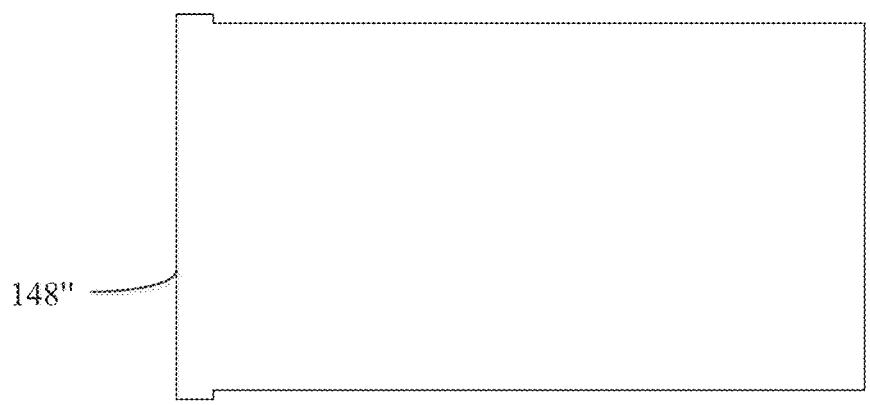

Referring now to FIGS. 23A-23C, rectangular membranes similar to those described above in FIGS. 10A-10C are illustrated. Thus, the description of the rectangular membranes in FIGS. 23A-23C can be referred to above. In general, rectangular membrane 148 may take a general thin rectangular shape. In a preferred embodiment, rectangular membrane 148 has a thin, planar shape and is made of an elastomer having elastic properties and good durability. Rectangular membrane 148 may have a uniform thickness from one end to the other. As yet a further alternative, rectangular membrane 148 may vary in thickness and exhibit more complex geometries. For example, rectangular membrane 148 may have a reduced thickness as the membrane extends from one end to the other. Alternatively, or in addition to, rectangular membrane 148 may incorporate metallic elements such as a spring to enhance the spring force of the membrane in a direction normal to plane of the membrane. In yet another embodiment, rectangular membrane 148 may be pre-formed with an undulating shape.

As is illustrated in FIG. 23A, rectangular membrane 148 may have two post receiving portions 167 and 168. Post receiving portions 167 and 168 may have a diameter slightly larger than that of posts 155 and 156. Also, as shown in FIG. 23A, rectangular membrane 148 may have extended portions 169 and 170. Extended portions 169 and 170 may permit fluid to more freely escape out of outlet 114 of implantable pump 102. Alternatively, in FIG. 23B, rectangular membrane 148' having two post receiving portions 167' and 168' may extend the entire length of the membrane without any extended portions. In yet another alternative, as shown in FIG. 23C, rectangular membrane 148" may not include the post receiving portions. This may permit the distal end of rectangular membrane 148" nearest outlet 114 to move more freely.

Figure 24A:
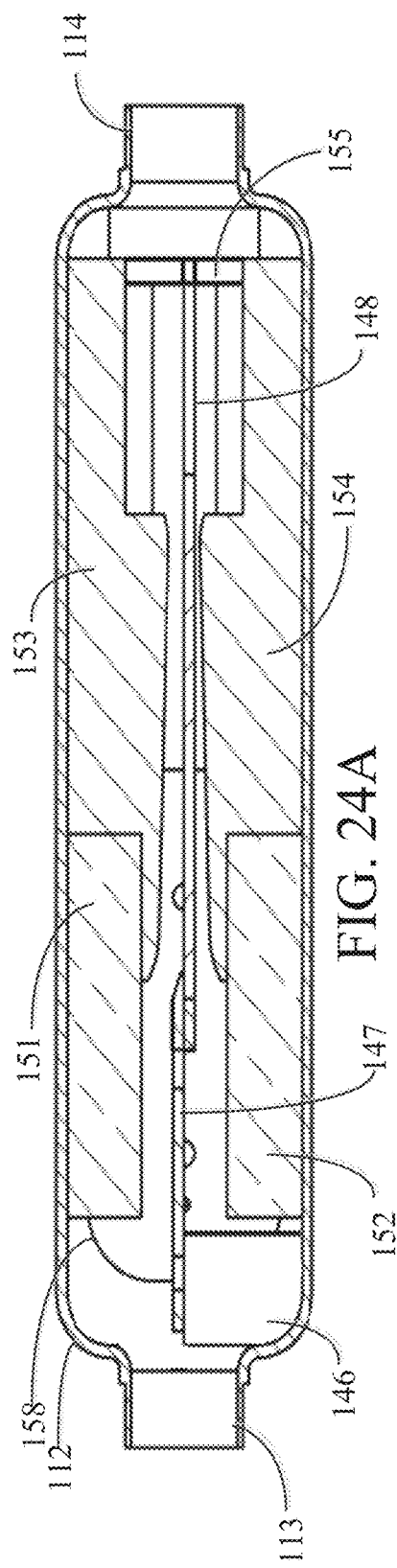
FIGS. 24A and 24B are cut-away cross sectional views of the pump assembly.
Figure 24B:
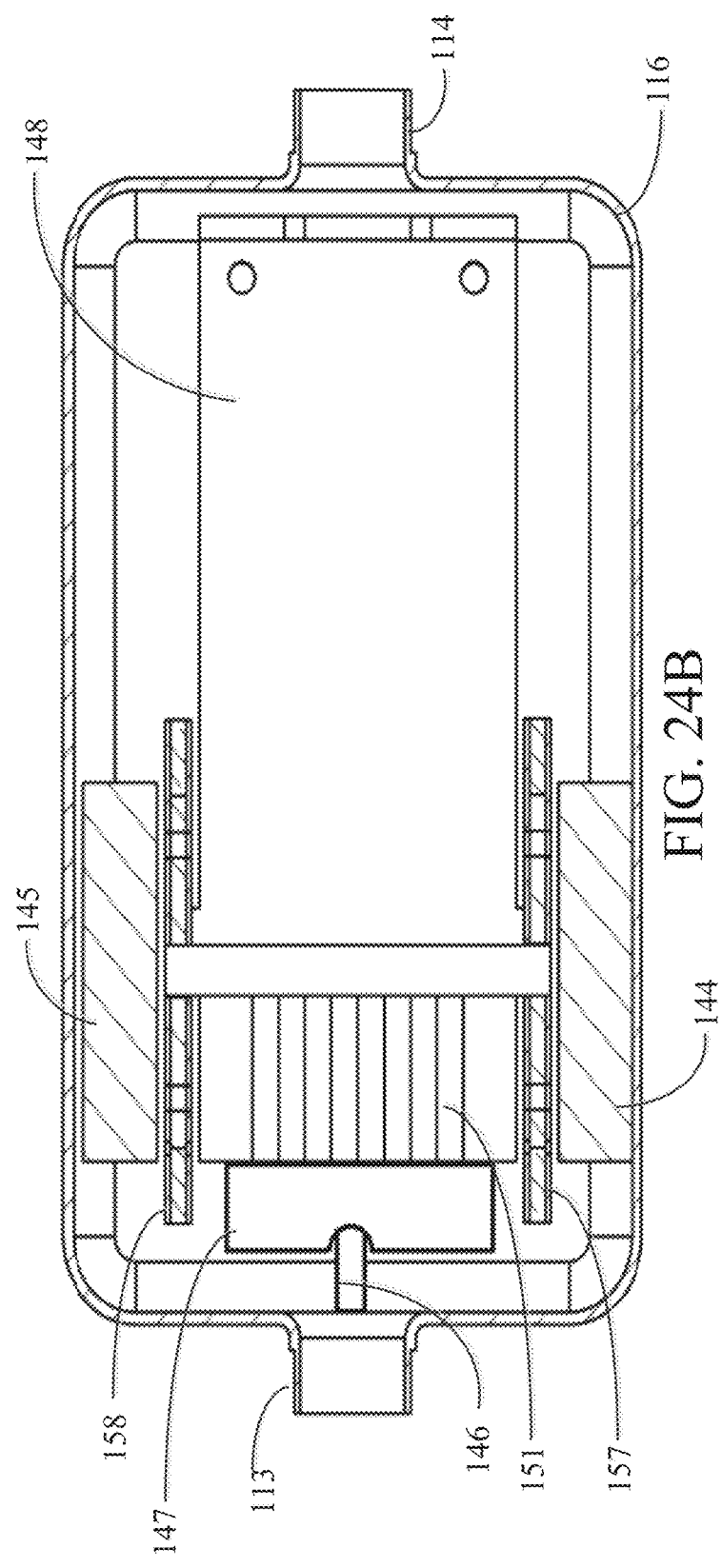

Referring now to FIGS. 24A and 24B, sectional views of implantable pump 102 are illustrated. In FIG. 24A, rectangular membrane 148 and membrane holder 147 are seen suspended between upper funnel 153 and upper magnet unit 151 above, and lower funnel 154 and lower magnet unit 152 below. Rectangular membrane 148 is shown being held in tension between membrane holder 147 and posts 155 and 156. As is also shown in FIG. 24A, second coil 158 is suspended within implantable pump housing 112 by membrane holder 147 which is secured in a cantilevered configuration by mounting structure 146.

From FIG. 24A it is clear that a flow channel exists between inlet 113 and outlet 114. Specifically, blood may flow through inlet 113, over and around mounting structure 146, and then flow toward outlet 114 between upper magnet unit 151 and a top surface of membrane holder 147 and membrane 148 as well as between lower magnet unit 152 and a bottom surface of membrane holder 147 and membrane 148. As the blood nears the outlet, blood may then flow between a bottom surface of upper funnel 153 and a top surface of membrane 148 as well as between a top surface of lower funnel 154 and a bottom surface of membrane 148. As blood flows through funnel assembly 150, the flow channel begins to narrow.

Referring now to FIG. 24B, a sectional view along an orthogonal plane from that shown in FIG. 24A is provided. As just described, blood may enter from inlet 113 and travel along membrane holder 147 and rectangular membrane 148. As is shown in FIG. 24B, blood may flow in the space between first coil 157 and second coil 158 and may even flow between first coil 157 and second coil 158 and fixation elements 145 and 144, respectively. As will be described in greater detail below, first coil 157 and second coil 158 and fixation elements, membrane holder 147 and rectangular membrane 148 all may move relative to pump housing 112. Conversely, mounting structure 146, magnet assembly 141, fixation elements 144 and 145, and funnel assembly 150 remain stationary relative to pump housing 112. Thus, in accordance with one aspect of the present invention, the implantable pump described herein avoids thrombus formation by placing all moving parts directly within the primary flow path, thereby reducing the risk of flow stagnation. Flow stagnation is further avoided by configuring all gaps in the flow path to be no less than 0.5 mm and also by eliminating secondary flow paths that may experience significantly slower flow rates.

Referring now to FIGS. 25A and 25B, implantable pump may be activated to pump blood from inlet 113 to outlet 114 by moving first coil 157 and second coil 158 up and down relative to pump housing 112. Constrained by only membrane holder 147, first coil 157 and second coil 158 may move up and down between membrane holder 147, rectangular membrane 148, magnet assembly 141 and funnel assembly 150 on one side and fixation elements 144 and 145 on the other. To move first coil 157 and second coil 158 up, current may be applied to first coil 157 and second coil 158 such that first coil 157 and second coil 158 generate a magnetic field that causes first coil 157 and second coil 158 to move toward upper magnet unit 151. Conversely, to move first coil 157 and second coil 158 down, current may be applied to first coil 157 and second coil 158 such that first coil 157 and second coil 158 generate an electric field that causes first coil 157 and second coil 158 to move toward lower magnet unit 152.

Upper magnet unit 151 and lower magnet unit 152 may have opposite polarities such that when current is applied in one direction through first coil 157 and second coil 158, first coil 157 and second coil 158 are attracted to upper magnet unit 151, but when current is applied to first coil 157 and second coil 158 in the reverse direction, first coil 157 and second coil 158 are attracted to lower magnet unit 152.

In FIG. 25A, current is flowing in first coil 157 and second coil 158 such that first coil 157 and second coil 158 are attracted to upper magnet unit 151. First coil 157 and second coil 158 may be activated by controller 3 by applying an electrical signal from battery 4 to first coil 157 and second coil 158, thus inducing current in the first coil 157 and second coil 158 and generating a magnetic field surrounding first coil 157 and second coil 158. As membrane holder 147 includes a flexible portion to which first coil 157 and second coil 158 are secured to and suspended by, first coil 157 and second coil 158 are free to move up toward upper magnet unit 151. Similarly, should the direction of current be reversed in first coil 157 and second coil 158, first coil 157 and second coil 158 would be attracted to lower magnet unit 152 and thus move down toward lower magnet unit 152.

As membrane holder 147 exhibits a spring force when elastically deformed in a direction normal to a longitudinal plane of membrane holder 147, when first coil 157 and second coil 158 move up toward upper magnet unit 151, membrane holder 147 exerts a downward spring force on first coil 157 and second coil 158 toward the neutral position. Similarly, when first coil 157 and second coil 158 move downward toward lower magnet unit 152, membrane holder 147 exerts an upward spring force on first coil 157 and second coil 158 toward the neutral position. The further first coil 157 and second coil 158 move from the undeflected neutral position, the greater the spring force applied to first coil 157 and second coil 158.

By manipulating the timing and intensity of the electrical signals applied to electromagnetic assembly 142, the frequency at which electromagnetic assembly 142 moves up and down may be altered. For example, by alternating the current induced in the electromagnetic assembly 142 more frequently, electromagnetic assembly 142 may be caused to cycle up and down more times in a given period. By increasing the voltage applied, the electromagnetic assembly 142 may be deflected at a faster rate and caused to travel longer distances.

As first coil 157 and second coil 158 are rigidly coupled to an end of membrane holder 147 and rectangular membrane 148 is also coupled at the same end of membrane holder 147, movement of first coil 157 and second coil 158 is applied to the end of rectangular membrane 148. FIGS. 25A and 125B illustrate movement by first coil 157 and second coil 158 being applied to rectangular membrane 148. As is shown in FIG. 25A, a current has been induced in first coil 157 and second coil 158 such that first coil 157 and second coil 158 are attracted to upper magnet unit 151. The movement of first coil 157 and second coil 158 has caused membrane securing portion 166 to move upward with first coil 157 and second coil 158. In FIG. 25A, the deformation in membrane holder 147 can clearly be seen. As can also be seen, rectangular membrane 148 has traveled upward with membrane securing portion 166.

As rectangular membrane 148 is attached to the same portion of membrane holder 147 as first coil 157 and second coil 158, when first coil 157 and second coil 158 travel a certain distance upward or downward, the end of rectangular membrane 148 attached to membrane holder 147 also travels the same distance. For example, when first coil 157 and second coil 158 travel 4 mm above the neutral position of membrane holder 147, the end of rectangular membrane 148 attached to membrane holder 147 also travels 4 mm in the same direction. Similarly, the frequency at which first coil 157 and second coil 158 reciprocates up and down is the same frequency at which rectangular membrane 148 travels the same distance. Preferably, the frequency is between 0 to 150 Hz, though other frequencies may be achieved using the system described herein.

Referring now to FIG. 25B, and as is illustrated in FIGS. 2 and 3 and described above, blood enters implantable pump 102 from inlet cannula 7 extending into the left atrium and flows into inlet 113 directly into delivery channel 171. As the blood moves toward outlet 114 it is directed through gap 172 between upper magnet unit 151 and lower magnet unit 152 and then into gap 173 between upper funnel 153 and lower funnel 154. By directing blood from delivery channel 171 to gap 172 blood is delivered to rectangular membrane 148. By inducing alternating current to first coil 157 and second coil 158, membrane 148 may be undulated between gaps 172 and 173 to induce wavelike formations in rectangular membrane 148 that moves from the edge of rectangular membrane 148 coupled to membrane holder 147 towards outlet 114. Accordingly, when blood is delivered to rectangular membrane 148 from delivery channel 171, it is propelled along both the top and bottom of rectangular membrane 148 and ultimately out of outlet 114. The waves formed in the undulating rectangular membrane may be manipulated by changing the speed at which first coil 157 and second coil 158 move up and down as well as the distance first coil 157 and second coil 158 move up and down. The transfer of energy from the membrane to the blood is directed along the length of the membrane towards outlet 114, and propels the blood along both sides of rectangular membrane 148.

FIG. 25B shows that when membrane securing portion 166 moves upward, the lower portion of gap 172 below membrane holder 147 and rectangular membrane 148 expands, causing blood to fill the lower portion of gap 172. As membrane securing portion 166 moves downward, the lower portion of gap 172 begins to narrow toward outlet 114, causing wave-like deformations to translate across the membrane. As the wave propagates across rectangular membrane 148, blood in the lower portion of gap 172 is propelled towards gap 173 and ultimately out of implantable pump 102. As blood moves toward outlet 14 within gap 173, gap 173 narrows accelerating the blood towards the outlet. Simultaneously, as membrane securing portion 166 moves downwards, the upper portion of gap 172 above the top surface of rectangular membrane 148 and membrane holder 147, begins to enlarge, allowing blood from delivery channel 171 to flow into this region. Subsequently, when membrane securing portion 166 is again thrust upwards, the upper portion of gap 172 begins to narrow, causing wave-like deformations to propagate across the membrane, propelling blood towards outlet 114. Preferably, the speed of the wave propagation is 1 to 1.5 m/s, though other propagation speeds may be achieved using the system described herein.

By manipulating the waves formed in the undulating membrane by changing the frequency and amplitude at which membrane securing portion 166 moves up and down, the pressure gradient within gap 172 and gap 173 and ultimately the flow rate of the blood moving through implantable pump 102 may be adjusted. Appropriately controlling the membrane securing portion 166 permits oxygen-rich blood to be effectively and safely pumped from the left atrium to the right subclavian artery and throughout the body as needed. While the pump described herein is described as pumping blood from the left atrium to the right subclavian artery, the implantable pump described herein could be used to pump blood from and to different areas, e.g. from the left ventricle to the aorta.

In addition to merely pumping blood from the left atrium to the subclavian artery, implantable pump 102 of the present invention may be operated to closely mimic physiologic pulsatility, without loss of pump efficiency. Pulsatility may be achieved nearly instantaneously by changing the frequency and amplitude at which membrane securing portion 166 moves, to create a desired flow output, or by ceasing movement of the electromagnetic assembly 142 for a period time to create a period of low or no flow output. Unlike typical rotary pumps, which require a certain period of time to attain a set number of rotations per minute to achieve a desired fluid displacement and pulsatility, implantable pump 102 may achieve a desired flow output nearly instantaneously and similarly may cease output nearly instantaneously due to the very low inertia generated by the small moving mass of the moving components of the pump assembly. The ability to start and stop on-demand permits rapid changes in pressure and flow. Along with the frequency and amplitude, the duty cycle, defined by the percentage of time rectangular membrane 148 is excited over a set period of time, may be adjusted to achieve a desired flow output and pulsatility, without loss of pump efficiency. Even holding frequency and amplitude constant, flow rate may be altered by manipulating the duty cycle between 0 and 100%.

In accordance with another aspect of the invention, controller 3 may be programmed by programmer 5 to operate at selected frequencies, amplitudes and duty cycles to achieve a wide range of physiologic flow rates and with physiologic pulsatilities. For example, programmer 5 may direct controller 3 to operate implantable pump 102 at a given frequency, amplitude and/or duty cycle during a period of time when a patient is typically sleeping and may direct controller 3 to operate implantable pump 102 at a different frequency, amplitude and or duty cycle during time periods when the patient is typically awake. Controller 3 or implantable pump 102 also may include an accelerometer or position indicator to determine whether the patient is supine or ambulatory, the output of which may be used to move from one set of pump operating parameters to another. When the patient experiences certain discomfort or a physician determines that the parameters are not optimized, physician may alter one or more of at least frequency, amplitude and duty cycle to achieve the desired functionality. Alternatively, controller 3 or mobile device 6 may be configured to alter one or more of frequency, amplitude and duty cycle to suit the patient's needs.

Implantable pump 102 further may comprise one or more additional sensors for adjusting flow output and pulsatility according to the demand of the patient. Sensors may be incorporated into implantable pump 102 or alternatively or in addition to may be implanted elsewhere in or on the patient. The sensors preferably are in electrical communication with controller 3, and may monitor operational parameters that measure the performance of implantable pump 102 or physiological sensors that measure physiological parameters of the patients such as heart rate or blood pressure. By using one or more physiological sensors, pulsatile flow may be synchronized with a cardiac cycle of the patient by monitoring blood pressure or muscle contractions, for example, and synchronizing the duty cycle according to the sensed output.

Controller 3 may compare physiological sensor measurements to current implantable pump output. If it is determined by analyzing sensor measurements that demand exceeds current output, frequency, amplitude and/or duty cycle may be automatically adjusted to meet current demand. Similarly, the controller may determine that current output exceeds demand and thus alter output by changing frequency, amplitude and/or duty cycle. Alternatively, or in addition to, when it is determined that demand exceeds current output, an alarm may sound from controller 3. Similarly, operational measurements from operational sensors may be compared against predetermined thresholds and where measurements exceed predetermined thresholds or a malfunction is detected, an alarm may sound from controller 3.

Implantable pump 102 is sized and shaped to produce physiological flow rates, pressure gradients and pulsatility at an operating point at which maximum efficiency is achieved. Preferably, implantable pump 102 is sized and shaped to achieve flow rates ranging from 1 to 3 liters per minute at pressure gradients lower than a threshold value associated with hemolysis. However, implantable pump 102 described herein may be sized and configured to achieve various other flow rates at pressure gradients lower than a threshold value associated with hemolysis. Also, to mimic a typical physiological pulse of 60 beats per minute, implantable pump 102 may pulse about once per second. To achieve such pulsatility, a duty cycle of 50% may be utilized with an "on" period of 0.5 seconds and an "off" period of 0.5 seconds. For a given system, maximum efficiency at a specific operating frequency, amplitude and voltage may be achieved while producing a flow rate of 1 to 3 liters per minute at a duty cycle of 50% by manipulating one or more of the shape and size of blood flow channels and gaps, elastic properties of the membrane holder, mass of the moving parts, membrane geometries, and elastic properties and friction properties of the membrane. In this manner, implantable pump 102 may be designed to produce desirable outputs to partially support physiological circulation while continuing to function at optimum operating parameters.

By adjusting the duty cycle, implantable pump 102 may be configured to generate a wide range of output flows at physiological pressure gradients. For example, pump system 1 may be configured to produce 1 to 3 liters per minute at a duty cycle of 50%, optimal operating frequency may be 120 Hz. For this system, flow output may be increased to 3 liters per minute or decreased to 1 liters per minute, for example, by changing only the duty cycle. As duty cycle and frequency operate independent of one another, duty cycle may be manipulated between 0 and 100% while leaving the frequency of 120 Hz unaffected.

The implantable pump system described herein may be tuned to achieve partial-support flow rates and physiological pressure gradients and pulsatility while avoiding hemolysis and platelet activation by applying low to moderate shear forces on the blood, similar to those exerted by a healthy heart. The moving components are rigidly affixed to one another and do not incorporate any parts that would induce friction, such as mechanical bearings or gears. Delivery channel 171 and gaps 172 and 173 are sized and configured to also avoid friction by sizing the channels and gaps such that clearances of at least 0.5 mm are maintained between all moving components. Similarly, first electromagnet 157 and second electromagnet 158 and membrane holder 147 are sized and configured to be separated by at least 0.5 mm from non-moving components to avoid friction.

Other embodiments of pump system 1 may include fewer or additional components. For example, FIG. 26 illustrates an alternative embodiment wherein pump assembly 116' includes electromagnetic assembly 142' having only one electromagnet positioned between magnet assembly 141'. Magnet assembly 141' has an upper magnet unit with a gap in the middle and a lower magnet unit with a gap in the middle. Pump assembly 116' also includes modified membrane holder 147' which is coupled to mounting structure 146 at a proximal end, coupled to the electromagnetic assembly 142' at a mid-section and coupled to rectangular membrane 148 at a distal end. As electromagnetic assembly 142' is electrically activated and attracted to lower magnet unit and upper magnet unit of magnet assembly 141', electromagnetic assembly 142' moves up and down through the gaps in magnet assembly 141'. Like in the embodiment described above, as modified membrane holder 147' moves up and down with electromagnetic assembly 142', the end of rectangular membrane 148 coupled to modified membrane holder 147' also travels up and down, thereby deforming rectangular membrane 148 and propagating wavelike deformations toward outlet 114. In this embodiment, though the displacement of rectangular membrane 148 is proportional to the displacement of electromagnetic assembly 142', the displacement may not be the same depending on the design of modified membrane holder 147'.

Other embodiments may employ an electromagnetic actuator having magnets and electromagnetic portions different than those described in FIGS. 18A-26. For example, in FIG. 27 an alternative system for propagating waves in the membrane is described. As is shown in FIG. 27, this alternative system may include membrane 175, first magnet 179, first coil 178, and first ferromagnetic casing 181 as well as second magnet 180, second coil 177, and second ferromagnetic casing 182. First magnet 179 and second magnet 180 are connected by rod 176 which is also coupled to membrane 175. First coil 178 and second coil 177 may be connected to controller 3 and/or battery 4. Controller may induce, and alternate, current in first coil 178 and second coil 177 which causes first magnet 179 and second magnet 180 to move up and down in tandem. As first magnet 179 and second magnet 180 move up and down, rod 176 may be moved up and down causing the portion of membrane 175 connected to rod 176 to move up and down. In this manner, membrane 175 may be caused to undulate. Membrane 175 may vary in thickness as it moves from one end to another. The alternative electromagnetic actuator shown in FIG. 27 may be designed and configured to fit within pump housing 112 and function as a blood pump in the manner described herein.

Figure 28:
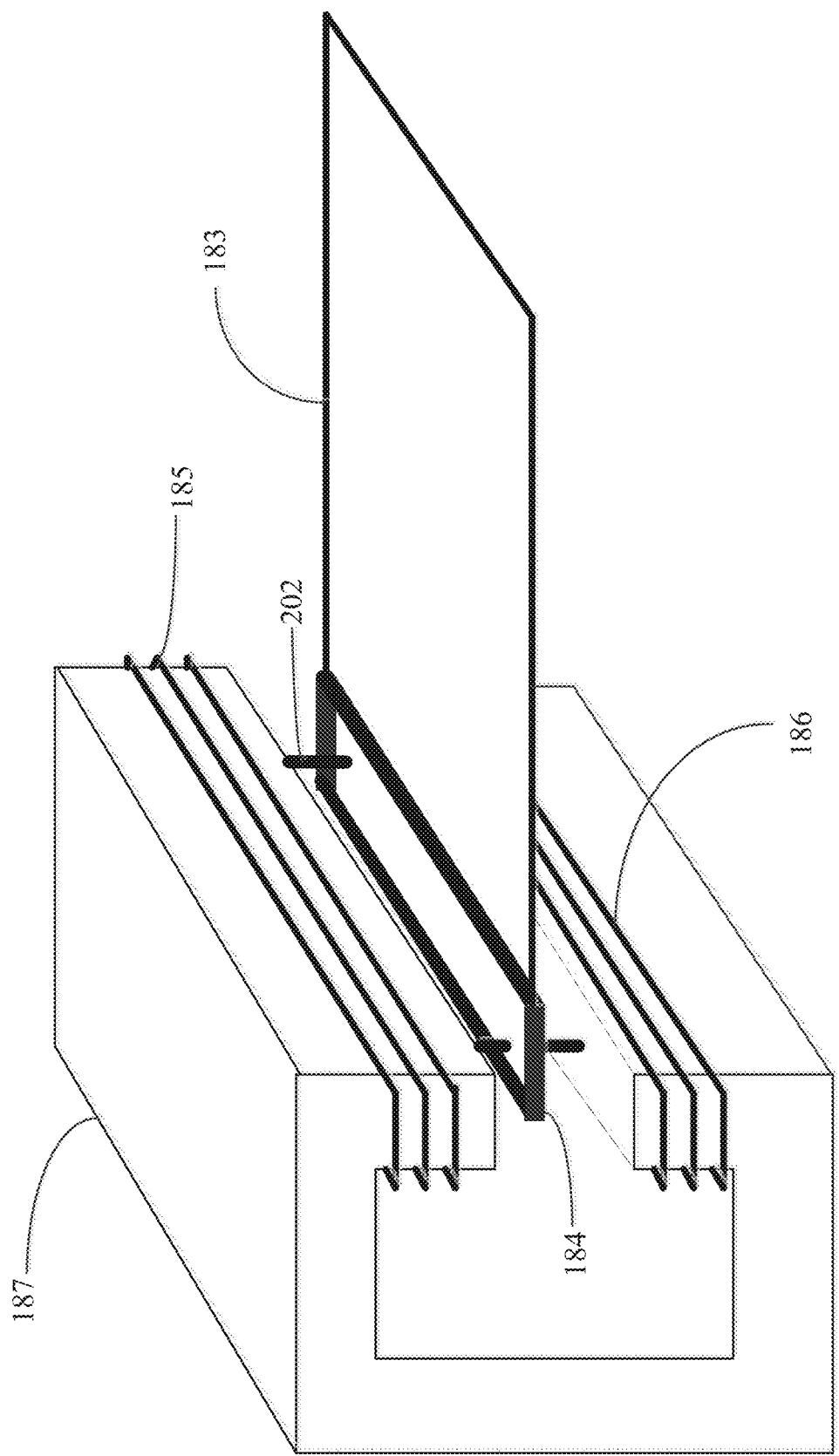
FIG. 28 is a perspective view of a dual coil electromagnetic actuator.

Referring now to FIG. 28, another electromagnetic actuator embodiment is illustrated. The system shown in FIG. 28 includes membrane 183, bar magnet 184, first coil 185, second coil 186, posts 202 and ferromagnetic housing 187. In this embodiment, first coil 185 and second coil 186 may be in communication with controller 3 and/or battery 4. First coil 185 and second coil 186 may be designed to receive an electrical signal that attracts bar magnet 184. First coil 185 and second coil 186 also may be designed to repel bar magnet 184. For example, first coil 185 may receive an electrical signal that causes first coil 185 to attract bar magnet 184 while at the same time, second coil 186 may receive an electrical signal that causes second coil 186 to repel bar magnet 184. By alternating the current applied to first coil 185 and second coil 186, bar magnet 184 is caused to move up and down along posts 202 towards and away from first coil 185 and second coil 186. Bar magnet 184 may be coupled to membrane 183 along the perimeter of one end of membrane 183. As bar magnet 184 moves up and down posts 202, the end of membrane 183 coupled to bar magnet 184 may move up and down causing wave-like deformations that propagate along membrane 183. The alternative electromagnetic actuator shown in FIG. 28 may be designed and configured to fit within pump housing 112 and function as a blood pump in the manner described herein.

Figure 29:
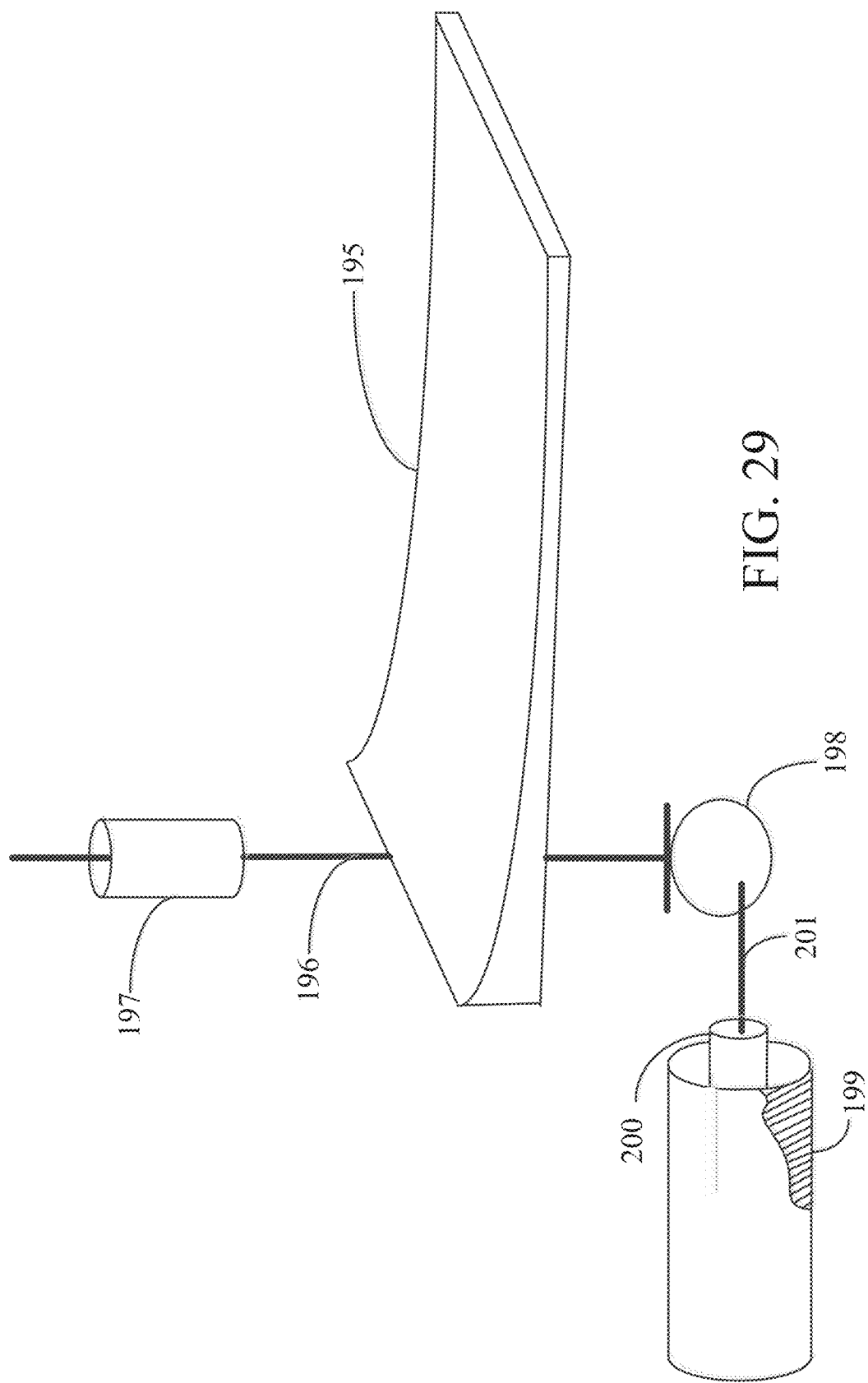
FIG. 29 is a perspective view of a mechanical actuator with a cam.

Referring now to FIG. 29, another electromechanical actuator embodiment is illustrated. The system shown in FIG. 29 includes membrane 195, rod 196, guide 197, cam 198, an assembly of coil 199, rotating magnet 200, the combination of 199 and 200 forming an asynchronous motor, and connector 201. Coil 199 may be in electrical communication with controller 3 and/or battery 4 and may be energized to move in rotation magnet 200 on the same axis as coil 199. Rotating magnet 200 may be connected to connector 201 which is connected to cam 198 at the other end. Membrane 195 is connected at one end to rod 196. Rod 196 is connected to cam 198 at one end and is guided by guide 197 so that rod 196 is only free to move along its longitudinal axis. As rotating magnet 200 is caused to rotate by the magnetic field generated by coil assembly 199, the movement of rotating magnet 200 is transmitted by cam 198 via connector 201 to rod 196 which moves up and down its longitudinal axis. As rod 196 moves up and down its longitudinal axis, the end of membrane 195 that is connected to rod 196 moves up and down causing wave-like deformations to propagate along membrane 195. The alternative electromechanical actuator shown in FIG. 29 may be designed and configured to fit within pump housing 112 and function as a blood pump in the manner described herein.

Referring now to FIGS. 30A-30H, various configurations for energizing implantable pump 2 or 102 described above are provided. As shown in FIG. 30A, controller 3 includes output port 18 which is electrically coupled to cable 9 as described above, which in turn is coupled to implantable pump 2 or 102. Controller 3 also includes power connector 203, which may be electrically coupled to a battery, an extension port electrically coupled to a battery, or an AC/DC power supply. For example, power connector 203 may be male, while the connector of the corresponding battery or extension port is female.

In one embodiment, as shown in FIG. 30B, controller 3 includes two power connectors, e.g., first power connector 203 and second power connector 204. As described above, first power connector 203 may be electrically coupled to a first battery, a first extension port electrically coupled to a first battery, or a first AC/DC power supply, and second power connector 203 may be electrically coupled to a second battery, a second extension port electrically coupled to a second battery, or a second AC/DC power supply. In this embodiment, first power connector 203 and second power connector 204 may both be male. In addition, controller 3 includes circuitry for switching between power sources such that energy is selectively transmitted to controller 3 from at least one of the first or second battery/power supply. For example, the circuitry may switch between a first and second battery intermittently, or after the remaining power level of one of the batteries reaches a predetermined threshold.

Referring now to FIGS. 30C-E, configurations are illustrated wherein controller 3 is directly electrically coupled to battery 4, such that controller 3 and battery 4 may be worn by the patient together, e.g., via a purse, shoulder bag, or holster. As shown in FIG. 30C, controller 3 of FIG. 30A may be electrically coupled to battery 4 via power connector 203, wherein power connector 203 is male and battery 4 has a corresponding female connector. For example, FIG. 30D illustrates controller 3 electrically coupled to battery 4, wherein battery 4 has a smaller size, and therefore lower capacity, and FIG. 30E illustrates controller 3 electrically coupled to battery 4, wherein battery 4 has a larger size, and therefore higher capacity. As will be understood by a person of ordinary skill in the art, battery 4 may have various sizes depending on the need of the patient.

Referring now to FIGS. 30F-H, configurations are illustrated wherein controller 3 is remotely electrically coupled to battery 4, such that the weight and volume of controller 3 and battery 4 are distributed and may be worn by the patient separately, e.g., via a belt or a vest. As shown in FIG. 30F, cable 214, which electrically couples controller 3 to battery 4, is electrically coupled to first power connector port 205 via strain relief 206, which is a hardwired junction between cable 214 and first power connector port 205. Power connector port 205 includes power connector 207, which may be electrically coupled to a battery. For example, power connector 207 may be male, while the connector of the corresponding battery is female.

As shown in FIG. 30G, controller 3 may be remotely electrically coupled to battery 4 via cable 214. Cable 214 is electrically coupled at one end to controller 3 via second power connector port 208 and strain relief 215, which is a hardwired junction between cable 214 and second power connector port 208, and electrically coupled at another end to battery 4 via first connector port 205 and strain relief 206. For example, power connector 203 of controller 3 may be male while the connector of corresponding second power connector port 208 is female, and power connector 207 of first power connector port 205 may be male while the connector of corresponding battery 4 is female.

In one embodiment, as shown in FIG. 30H, controller 3 may be remotely electrically coupled to multiple batteries, e.g., battery 4A and battery 4B, via a single second power connector port 208. As shown in FIG. 30H, second power connector port 208 includes first strain relief 215A and second strain relief 215B, such that controller 3 is remotely electrically coupled to battery 4A via cable 214A and remotely electrically coupled to battery 4B via cable 214B. Specifically, cable 214A is electrically coupled at one end to controller 3 via second power connector port 208 and first strain relief 215A, and electrically coupled at another end to battery 4A via first connector port 205A and strain relief 206A, and cable 214B is electrically coupled at one end to controller 3 via second power connector port 208 and second strain relief 215B, and electrically coupled at another end to battery 4B via first connector port 205B and strain relief 206B. In this embodiment, controller 3 may include circuitry for switching between battery 4A and battery 4B such that energy is selectively transmitted to controller 3 from at least one of battery 4A and battery 4B. For example, the circuitry may switch between battery 4A and battery 4B intermittently, or after the remaining power level of one of the batteries reaches a predetermined threshold. Alternatively, controller 3 may receive energy from battery 4A and battery 4B simultaneously.

In another embodiment, as shown in FIG. 30I, controller 3 is electrically coupled to AC/DC power supply 209, which may be plugged into an electrical outlet via AC plug 213, e.g., when the patient is resting bedside. Specifically, AC/DC power supply 209 is electrically coupled to controller 3 via cable 214, such that cable 214 is electrically coupled at one end to controller 3 via second power connector port 208 and strain relief 215, and electrically coupled at another end to AC/DC power supply 209 via first power supply port 210. In addition, AC/DC power supply 209 is electrically coupled to plug 213 via cable 212 and second power supply port 211.

Controller 3 may include an internal battery, such that the internal battery powers controller 3 and implantable pump 2 or 102 during the time required for battery 4 to be replaced and/or recharged. Accordingly, controller 3 may include circuitry for switching between power sources such that energy is transmitted to controller 3 from the internal battery while battery 4 is disconnected from controller 3, and from battery 4 when battery 4 is electrically coupled to controller 3. In addition, the circuitry may allow battery 4 to charge the internal battery while also energizing implantable pump 2 or 102 until the internal battery is recharged to a desired amount, at which point the circuitry allows battery 4 to solely energize implantable pump 2 or 102. Similarly, when controller 4 is electrically coupled to AC/DC power supply 209, the circuitry may allow AC/DC power supply 209 to charge the internal battery while also energizing implantable pump 2 or 102 until the internal battery is recharged to a desired amount, at which point the circuitry allows AC/DC power supply 209 to solely energize implantable pump 2 or 102.

While various illustrative embodiments of the invention are described above, it will be apparent to one skilled in the art that various changes and modifications may be made therein without departing from the invention. For example, pump system 1 may be ordered differently and may include additional or fewer components of various sizes and composition. The appended claims are intended to cover all such changes and modifications that fall within the true spirit and scope of the invention.

What is claimed is:

1. A method for pumping blood comprising:
   activating a first electromagnetic coil and a second electromagnetic coil disposed within a pump housing to simultaneously induce a first current in the first electromagnetic coil and a second current in the second electromagnetic coil, the first electromagnetic coil and the second electromagnetic coil oriented with respect to a magnetic assembly disposed in the pump housing such that the magnet assembly is disposed between the first electromagnetic coil and the second electromagnetic coil;
   wherein, the first current and the second current interact with a magnetic field generated by the magnetic assembly to excite a rectangular membrane coupled to the magnetic assembly thereby inducing a wave-like deformation in the rectangular membrane to pump blood from an inlet of the pump housing, along the rectangular membrane, and out an outlet of the pump housing.

2. The method of claim 1, wherein the first current and the second current are oriented in a direction to cause an attraction between the magnetic assembly and at least the first electromagnetic coil.

3. The method of claim 1, wherein the first current and the second current cause the magnetic assembly coupled to the rectangular membrane to move from a first position to a second position to induce the wave-like deformation in the rectangular membrane.

4. The method of claim 3, further comprising, after activating the first electromagnetic coil and the second electromagnetic coil to simultaneously induce the first current in the first electromagnetic coil and the second current in the second electromagnetic coil, activating the first electromagnetic coil and the second electromagnetic coil to simultaneously induce a third current in the first electromagnetic coil and a fourth current in the second electromagnetic coil, the third current opposite the first current and the fourth current opposite the second current.

5. The method of claim 4, wherein the third current and the fourth current cause the magnetic assembly coupled to the rectangular membrane to move from the second position back to the first position.

6. The method of claim 1, further comprising ceasing activation of the first electromagnetic coil and the second electromagnetic coil to cause the magnetic assembly to return to a neutral position.

7. The method of claim 1, wherein, the first current and the second current interact with the magnetic field generated by the magnetic assembly to excite the rectangular membrane by causing the magnetic assembly to move from a neutral position to a displaced position, and wherein a resisting force acts on the magnetic assembly when the magnetic assembly is in the displaced position.

8. The method of claim 1, wherein the first current and the second current interact with the magnetic field generated by the magnetic assembly to excite the rectangular membrane, causing the magnetic assembly to move from a neutral position to a displaced position, and wherein the magnetic assembly is guided linearly by a guide post disposed within the housing.

9. The method of claim 1, further comprising alternating the first current in the first electromagnetic coil and the second current in the second electromagnetic to change a speed at which the magnetic assembly moves.

10. The method of claim 1, further comprising alternating the first current in the first electromagnetic coil and the second current in the second electromagnetic to change a distance which the magnetic assembly moves.

11. A non-transitory computer-readable memory medium configured to store instructions thereon that, when executed by a processor, cause the processor to:
cause a first electromagnetic coil and a second electromagnetic coil disposed within a pump housing to activate simultaneously induce a first current in the first electromagnetic coil and a second current in the second electromagnetic coil, the first electromagnetic coil and the second electromagnetic coil oriented with respect to a magnetic assembly disposed in the pump housing such that the magnet assembly is disposed between the first electromagnetic coil and the second electromagnetic coil;
wherein, the first current and the second current interact with a magnetic field generated by the magnetic assembly to excite a rectangular membrane coupled to the magnetic assembly thereby inducing a wave-like deformation in the rectangular membrane to pump blood from an inlet of the pump housing, along the rectangular membrane, and out an outlet of the pump housing.

12. The non-transitory computer-readable memory medium of claim 11, wherein the first current and the second current are oriented in a direction to cause an attraction between the magnetic assembly and at least the first electromagnetic coil.

13. The non-transitory computer-readable memory medium of claim 11, wherein the first current and the second current cause the magnetic assembly coupled to the rectangular membrane to move from a first position to a second position to induce the wave-like deformation in the rectangular membrane.

14. The non-transitory computer-readable memory medium of claim 13, wherein the instructions, when executed, after causing the first electromagnetic coil and the second electromagnetic coil to simultaneously activate to induce the first current in the first electromagnetic coil and the second current in the second electromagnetic coil, cause the first electromagnetic coil and the second electromagnetic coil to simultaneously activate to induce a third current in the first electromagnetic coil and a fourth current in the second electromagnetic coil, the third current opposite the first current and the fourth current opposite the second current.

15. The non-transitory computer-readable memory medium of claim 14, wherein the third current and the fourth current cause the magnetic assembly coupled to the rectangular membrane to move from the second position back to the first position.

16. The non-transitory computer-readable memory medium of claim 11, wherein the instructions, when executed, further cause the first electromagnetic coil and the second electromagnetic coil to cease activation to cause the magnetic assembly to return to a neutral position.

17. The non-transitory computer-readable memory medium of claim 11, wherein, the first current and the second current interact with the magnetic field generated by the magnetic assembly to excite the rectangular membrane by causing the magnetic assembly to move from a neutral position to a displaced position, and wherein a resisting force acts on the magnetic assembly when the magnetic assembly is in the displaced position.

18. The non-transitory computer-readable memory medium of claim 11, wherein the first current and the second current interact with the magnetic field generated by the magnetic assembly to excite the rectangular membrane, causing the magnetic assembly to move from a neutral position to a displaced position, and wherein the magnetic assembly is guided linearly by a guide post disposed within the housing.

19. The non-transitory computer-readable memory medium of claim 11, wherein the instructions, when executed, further cause the first current in the first electromagnetic coil and the second current in the second electromagnetic to alternate to change a speed at which magnetic assembly moves.

20. The non-transitory computer-readable memory medium of claim 11, wherein the instructions, when executed, further cause the first current in the first electromagnetic coil and the second current in the second electromagnetic to alternate to change a distance which magnetic assembly moves.

* * * * *